US008124846B2

(12) United States Patent
Zink et al.

(10) Patent No.: US 8,124,846 B2
(45) Date of Patent: Feb. 28, 2012

(54) HERBICIDE-TOLERANT PLANTS THROUGH BYPASSING METABOLIC PATHWAY

(75) Inventors: Olivier Zink, Clermont-Ferrand (FR); Eric Paget, Caluire (FR); Anne Rolland, Lyons (FR); Alain Sailland, Saint Didier Au mont d'&or (FR); Georges Freyssinet, Saint-Cyr-Au-Mont-d'or (FR)

(73) Assignee: Bayer CropScience S.A.S., Lyons (FR)

( * ) Notice: Subject to any disclaimer, the term of this patent is extended or adjusted under 35 U.S.C. 154(b) by 1046 days.

(21) Appl. No.: 11/982,955

(22) Filed: Nov. 6, 2007

(65) Prior Publication Data

US 2008/0163392 A1 Jul. 3, 2008

Related U.S. Application Data

(62) Division of application No. 10/415,302, filed as application No. PCT/FR01/03364 on Oct. 30, 2001, now Pat. No. 7,304,209.

(30) Foreign Application Priority Data

Oct. 30, 2000 (FR) ..................................... 00 13942

(51) Int. Cl.
*C12N 15/82* (2006.01)
*C12N 15/52* (2006.01)

(52) U.S. Cl. ..................... 800/300; 435/419; 435/320.1; 536/23.2; 800/288

(58) Field of Classification Search ........................ None
See application file for complete search history.

(56) References Cited

U.S. PATENT DOCUMENTS

| | | | |
|---|---|---|---|
| 5,347,076 | A | 9/1994 | Pohlenz et al. |
| 6,313,282 | B1 | 11/2001 | Atanassova et al. |
| 6,812,010 | B1 | 11/2004 | Derose et al. |

FOREIGN PATENT DOCUMENTS

| | | |
|---|---|---|
| EP | 0 343 100 | 11/1989 |
| EP | 0 633 317 | 1/1995 |
| WO | WO-98/21348 | 5/1998 |
| WO | WO-99/34008 | 7/1999 |

OTHER PUBLICATIONS

Prieto et al 1996, Journal of Bacteriology 178(1): 111-120.*
Bernard Grausem et al.; "Functional Expression of *Saccharomyces cerevisiae* CYP51A1 encoding lanosterol-14-demethylase in tobacco results in bypass of endogenous sterol biosynthetic pathway and resistance to an obtusifoliol-14-demethylase herbicide inhibitor"; The Plant Journal; vol. 7, No. 5, pp. 761-770, 1995.
M.A. Prieto et al.,; "Molecular characterization of the 4-hydrophenylacetate catabolic pathway of *Escherichia coli* W: Engineering a mobile aromatic degradative cluster"; Journal of Bacteriology; vol. 178; No. 1; pp. 111-120; 1996.

* cited by examiner

*Primary Examiner* — David H Kruse
(74) *Attorney, Agent, or Firm* — Connolly Bove Lodge & Hutz LLP

(57) ABSTRACT

The invention concerns a novel method for making herbicide-tolerant plants, in particular to HPPD inhibiting herbicides, the nucleic acid sequences coding for enzymes capable of being used in said method, expression cassettes containing them and transgenic plants comprising at least one of said expression cassettes.

19 Claims, 7 Drawing Sheets

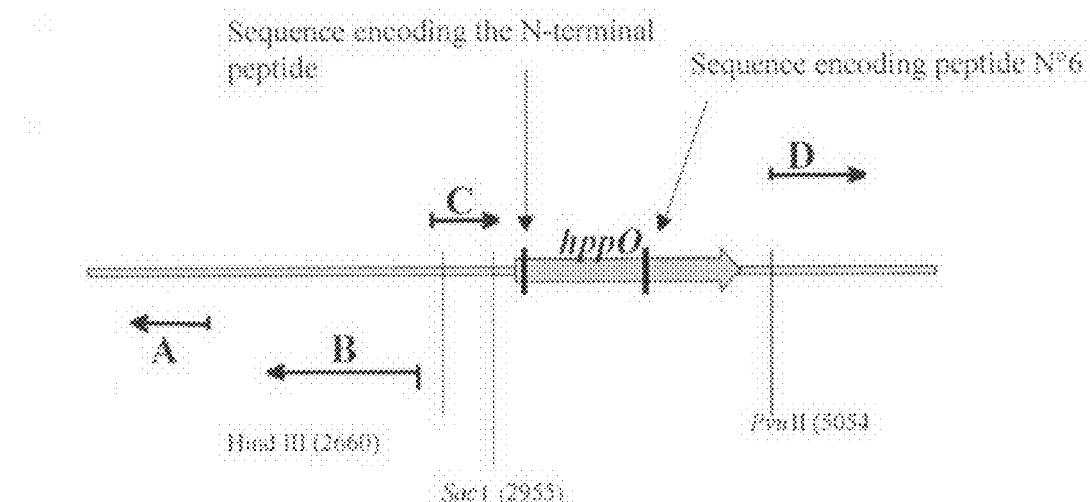

Figure 3

```
                                                        SacI

2901  TTTGGAAATC GACGGGATCC AGCGGACCAG CACTGCCATC TCCGTCGTGG
      AAACCTTTAG CTGCCCTAGG TCGCCTGGTC GTGACGGTAG AGGCAGCACC

      SacI
      ~~~~~~
2951  AGCTCATGCC GCCCCGCTAT GACGGCCTGC TGGCCCGGCT GTCCCAGCAG
      TCGAGTACGG CGGGGCGATA CTGCCGGACG ACCGGGCCGA CAGGGTCGTC

3001  GAGAGCCGCC ATCCCAGCTA GGGCATAGGT GATCCGCACC ACCTTTGAGC
      CTCTCGGCGG TAGGGTCGAT CCCGTATCCA CTAGGCGTGG TGGAAACTCG

3051  ATATTTGCAG TAGCTACTGT GATAAACTGC CAAAAATACC AGCTCATGTC
      TATAAACGTC ATCGATGACA CTATTTGACG GTTTTTATGG TCGAGTACAG

  +2
3101  TGTTCACTTG CCAATCGCTG ATCCAGATCC GACGGATTCC GCATGACTTC
      ACAAGTGAAC GGTTAGCGAC TAGGTCTAGG CTGCCTAAGG CGTACTGAAG

  +2
3151  ACTTACAGTG TCCGGCGCGG TGGCGCAGGT CCTCAGCAGC TATGTCAGCG
      TGAATGTCAC AGGCCGCGCC ACCGCGTCCA GGAGTCGTCG ATACAGTCGC

                 . . . . . . . . . . . . .
                 . . . . . . . . . . . . .
                 . . . . . . . . . . . . .

  +2
4301  GCCGAAGCAG GCGGTGGCGG GCTAGGGCCG GCCTCGTCGA AATGCCGCCC
      CGGCTTCGTC CGCCACCGCC CGATCCCGGC CGGAGCAGCT TTACGGCGGG

4351  TCCAACCCAA CTCAGTACCA GCTCAGGGCG TTCTCAGGGC TGGGAACGCC
      AGGTTGGGTT GAGTCATGGT CGAGTCCCGC AAGAGTCCCG ACCCTTGCGG
```

Figure 4

```
                   51                                              100
HPPoxydase  (40)  ~G KFTAV  GA IAA DAYY AS  LAAGTT Y  YTNA TA AE V
D47069      (48)  ~S RILPV   ANRAFM AAVG I   AGVALV S  CSNL TG AT N
G69464      (38)  ~G RHITT   QGATHA DGYA AS  VGVAFA S  ATNT TG AT Y
YCEC1L      (51)  ~Q RHILA   QCACFI QGMA TD  PAVCMACS  ATNL TA AD R
P37603      (49)  DS HYIQV   EVGAMA AADA LI  IGVCFGSA  GTHL NG YD R
T34668      (42)  ~G EWVRV   ETAAFA GAEAQI   LTACAGSC  NLBL NG YD H

                   451                                             500
HPPoxydase (426)  RAVDDGN LVLAA  GFLMGLS LE L GAASSAVV  ~~Y DAAYGAEI
D47069     (434)  LVNPQRK ~YSVS  GFLQSSN LE AVRLHANILH WVD GYN~MVAI
G69464     (419)  VAFPEKI ~IDIA  SFFMNFQ LA CVKYEIPVKV ~LN GYLG~MVR
YCEC1L     (431)  LANPDRK ~LCFS  SLMMNLQ MA ASENQLDVKI ~MN EALG~LVH
P37603     (434)  LNYPERQ ~FNLA  GASMTMQ LA CYQYHLPVIN ~FT CQYGFIKD
T34668     (424)  FTDRRRQ ~YSMS  GFTMLMG FL LVQHDLPVKI ~FN SSLG~MVE
```

Figure 5

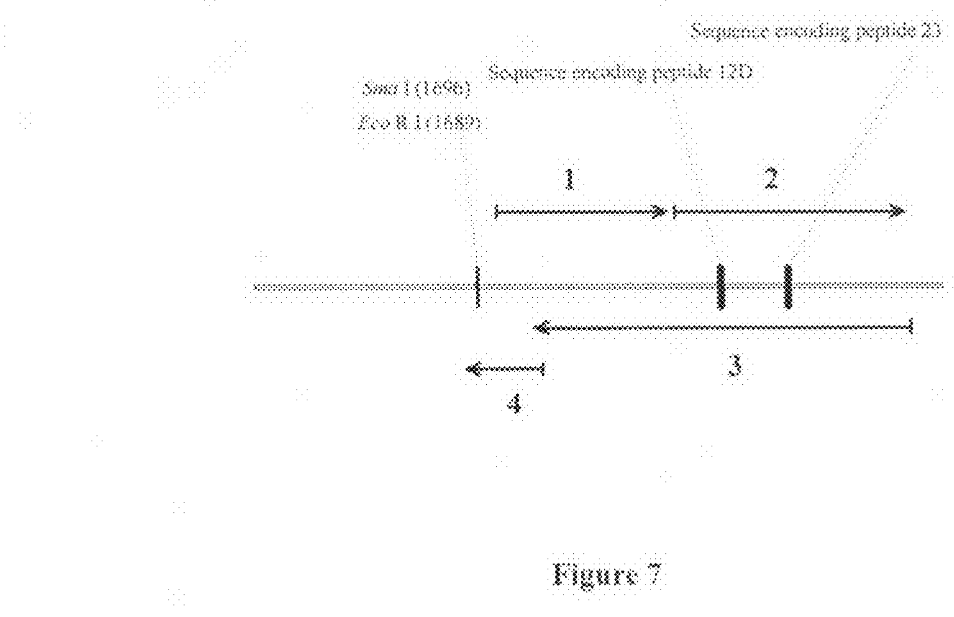

| | | |
|---|---|---|
| HPAH | (19) | [illegible] |
| hydroxylase - Q53657 | (1) | [illegible] |
| monooxygenase - Q9ZAM4 | (51) | [illegible] |
| putativ oxygenase - Q54171 | (1) | [illegible] |
| MHPA_ECOLI | (1) | [illegible] |
| Oxygenase - O86481 | (1) | [illegible] |
| Consensus | (51) | [illegible] |

B

| | | 301 … 350 |
|---|---|---|
| HPAH | (152) | [illegible] |
| hydroxylase - Q53657 | (107) | [illegible] |
| monooxygenase - Q9ZAM4 | (201) | [illegible] |
| putativ oxygenase - Q54171 | (107) | [illegible] |
| MHPA_ECOLI | (117) | [illegible] |
| Oxygenase - O86481 | (117) | [illegible] |
| Consensus | (201) | [illegible] |

C

| | | 351 … 400 |
|---|---|---|
| HPAH | (288) | [illegible] |
| hydroxylase - Q53657 | (230) | [illegible] |
| monooxygenase - Q9ZAM4 | (348) | [illegible] |
| putativ oxygenase - Q54171 | (244) | [illegible] |
| MHPA_ECOLI | (262) | [illegible] |
| Oxygenase - O86481 | (253) | [illegible] |
| Consensus | (351) | [illegible] |

D

| | | 401 … 450 |
|---|---|---|
| HPAH | (338) | [illegible] |
| hydroxylase - Q53657 | (278) | [illegible] |
| monooxygenase - Q9ZAM4 | (397) | [illegible] |
| putativ oxygenase - Q54171 | (292) | [illegible] |
| MHPA_ECOLI | (310) | [illegible] |
| Oxygenase - O86481 | (300) | [illegible] |
| Consensus | (401) | [illegible] |

Figure 8

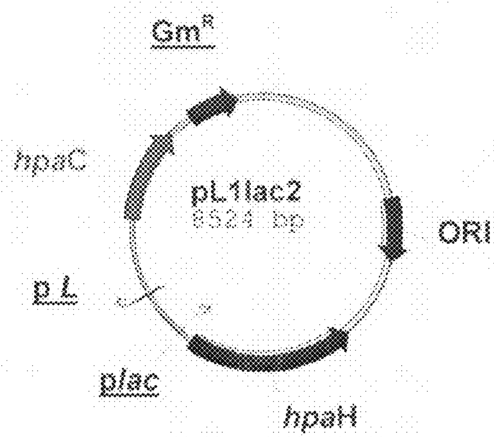

Figure 9

SEQUENCE LISTING

```
<160> NUMBER OF SEQ ID NOS: 101

<210> SEQ ID NO 1
<211> LENGTH: 1683
<212> TYPE: DNA
<213> ORGANISM: Arthrobacter globiformis
<220> FEATURE:
<221> NAME/KEY: CDS
<222> LOCATION: (1)..(1683)

<400> SEQUENCE: 1

atg act tca ctt aca gtg tcc ggc cgg gtg gcg cag gtc ctc agc agc       48
Met Thr Ser Leu Thr Val Ser Gly Arg Val Ala Gln Val Leu Ser Ser
1               5                   10                  15

tat gtc agc gat gtg ttc ggt gtg atg ggc aac gga aac gtc tac ttc       96
Tyr Val Ser Asp Val Phe Gly Val Met Gly Asn Gly Asn Val Tyr Phe
            20                  25                  30

ctg gac gcc gcc gag aag gag ggc ctc cgc ttc acg gcc gta cgc cat      144
Leu Asp Ala Ala Glu Lys Glu Gly Leu Arg Phe Thr Ala Val Arg His
        35                  40                  45

gaa ggt gcc gcc atc gcg gcg gcg gac gcc tac tat cgg gca tcc ggg      192
Glu Gly Ala Ala Ile Ala Ala Ala Asp Ala Tyr Tyr Arg Ala Ser Gly
    50                  55                  60

cgc ctg gcg gcg ggg acc acc acc tac ggc ccc ggt tac acc aac gcc      240
Arg Leu Ala Ala Gly Thr Thr Thr Tyr Gly Pro Gly Tyr Thr Asn Ala
65                  70                  75                  80

ctg acg gcc ctc gcc gag gcg gtc cag gcg cag atc ccc gtg gtg ctc      288
Leu Thr Ala Leu Ala Glu Ala Val Gln Ala Gln Ile Pro Val Val Leu
```

```
                85                  90                  95

gtc acc ggg gac gcc ccg agc agc ggc gcc cgg cct tgg gac gtg gac      336
Val Thr Gly Asp Ala Pro Ser Ser Gly Ala Arg Pro Trp Asp Val Asp
            100                 105                 110

cag gcc gcg atc gcc gcc ggg ctg ggg gcg gcg acc ttc acg gtc acc      384
Gln Ala Ala Ile Ala Ala Gly Leu Gly Ala Ala Thr Phe Thr Val Thr
        115                 120                 125

cgt gaa gcc gca ggc tcc atc acg cag gaa gcg gtg gag tac gca ctt      432
Arg Glu Ala Ala Gly Ser Ile Thr Gln Glu Ala Val Glu Tyr Ala Leu
    130                 135                 140

gcc cgg cgg acc gcc gtc gtg atc gcc gtt cca tac gac ctg tcg gcc      480
Ala Arg Arg Thr Ala Val Val Ile Ala Val Pro Tyr Asp Leu Ser Ala
145                 150                 155                 160

ctt gag gcg gcg gag gaa gat ctt ccc gtg ccg ccg gcg gcc tcg gtt      528
Leu Glu Ala Ala Glu Glu Asp Leu Pro Val Pro Pro Ala Ala Ser Val
                165                 170                 175

ccg gac gcc atc ggc ggc gga ctc gga cgg gcg gcc gaa gtg cgg gcg      576
Pro Asp Ala Ile Gly Gly Gly Leu Gly Arg Ala Ala Glu Val Arg Ala
            180                 185                 190

gcc gaa ttg ctg gcg ggc gcg aag cgg ccg ctc atc ctt gcc ggc cgc      624
Ala Glu Leu Leu Ala Gly Ala Lys Arg Pro Leu Ile Leu Ala Gly Arg
        195                 200                 205

ggt gcg cac ctc gca gga gcc ggc ccc gaa ctc cgg gaa ctc gcc gac      672
Gly Ala His Leu Ala Gly Ala Gly Pro Glu Leu Arg Glu Leu Ala Asp
    210                 215                 220

cgc ctc ggc gcg ctc acg gcc ggc acc gca ctg gcg ctg aac ctg ctg      720
Arg Leu Gly Ala Leu Thr Ala Gly Thr Ala Leu Ala Leu Asn Leu Leu
225                 230                 235                 240

cag ggc gag ggg tac ctc ggc gtc gcg ggc ggc ttc ggc acg gat acc      768
Gln Gly Glu Gly Tyr Leu Gly Val Ala Gly Gly Phe Gly Thr Asp Thr
                245                 250                 255

gcc gcc ggg ctc atg ggc gag gcg gac gtg gtg ctc gtg gcg gga gcc      816
Ala Ala Gly Leu Met Gly Glu Ala Asp Val Val Leu Val Ala Gly Ala
            260                 265                 270

agc ctg acc ccc ttc acc atg cgc ttc ggc cac ctg atc ggc ccg gac      864
Ser Leu Thr Pro Phe Thr Met Arg Phe Gly His Leu Ile Gly Pro Asp
        275                 280                 285

gcc acc gtg atc cag atc gac acc gcc atg gag ccg acg gac ccg cgg      912
Ala Thr Val Ile Gln Ile Asp Thr Ala Met Glu Pro Thr Asp Pro Arg
    290                 295                 300

gtg gac ctg ttt gtc agt gcg gac gcg aag gcc gct gcc ggc cgg atc      960
Val Asp Leu Phe Val Ser Ala Asp Ala Lys Ala Ala Ala Gly Arg Ile
305                 310                 315                 320

ctc cgg ctg ctg gat gac gcc gcc ggg gcc aat gcg tcg aag gcc tgg     1008
Leu Arg Leu Leu Asp Asp Ala Ala Gly Ala Asn Ala Ser Lys Ala Trp
                325                 330                 335

cgc gcg gaa gca ctc aag cgt ctg gcc gaa gga ccc tgc cac cac ccc     1056
Arg Ala Glu Ala Leu Lys Arg Leu Ala Glu Gly Pro Cys His His Pro
            340                 345                 350

ggc acc gca gag acc acg gac ggc cgc ctt gac ccc cgg gcg ctt gct     1104
Gly Thr Ala Glu Thr Thr Asp Gly Arg Leu Asp Pro Arg Ala Leu Ala
        355                 360                 365

tcg gca ctg gat gcc gtc ctg ccg gaa cgc cgc acc gtg gtc cag gac     1152
Ser Ala Leu Asp Ala Val Leu Pro Glu Arg Arg Thr Val Val Gln Asp
    370                 375                 380

ggc ggg cac ttc ctg ggc tgg gca ccc atg tac tgg cgc atc ccc cgt     1200
Gly Gly His Phe Leu Gly Trp Ala Pro Met Tyr Trp Arg Ile Pro Arg
385                 390                 395                 400

cct cag gac ctg gtc atg gtg ggg acc gcg tac cag tcg atc ggg ctt     1248
Pro Gln Asp Leu Val Met Val Gly Thr Ala Tyr Gln Ser Ile Gly Leu
```

```
                405                 410                 415

ggc ctg gcc agc gcc gtg ggg gcg tcc cgg gcc gtg gac gac ggc aat      1296
Gly Leu Ala Ser Ala Val Gly Ala Ser Arg Ala Val Asp Asp Gly Asn
            420                 425                 430

atc ctg gtg ctg gcg gcg ggc gac ggc gga ttc ctg atg ggc ctg tcc      1344
Ile Leu Val Leu Ala Ala Gly Asp Gly Gly Phe Leu Met Gly Leu Ser
        435                 440                 445

gac ctg gaa tcg ctc gtg ggc gcg gcg agc agc gcc gtc gtg gtg atc      1392
Asp Leu Glu Ser Leu Val Gly Ala Ala Ser Ser Ala Val Val Val Ile
    450                 455                 460

tac aac gac gcc gcc tac ggg gcc gag atc cat cag tac ggc tca cgg      1440
Tyr Asn Asp Ala Ala Tyr Gly Ala Glu Ile His Gln Tyr Gly Ser Arg
465                 470                 475                 480

ggg ctc acc gaa aag ccc atg ctg atc ccc gaa gtg gac ttc agc ggg      1488
Gly Leu Thr Glu Lys Pro Met Leu Ile Pro Glu Val Asp Phe Ser Gly
                485                 490                 495

att gcc cgc gcg atc ggg gcg gaa tcc gca atc atc cgc aag ctg tcg      1536
Ile Ala Arg Ala Ile Gly Ala Glu Ser Ala Ile Ile Arg Lys Leu Ser
            500                 505                 510

gac ctc tcc gcg ctc acg gac tgg atc gag gcc ggc gcc agg gga acc      1584
Asp Leu Ser Ala Leu Thr Asp Trp Ile Glu Ala Gly Ala Arg Gly Thr
        515                 520                 525

ttc gtg gcc gac tgc cgc atc acc tca agc gtc cgg gcc ccg tgg ctg      1632
Phe Val Ala Asp Cys Arg Ile Thr Ser Ser Val Arg Ala Pro Trp Leu
    530                 535                 540

agc gaa tgg atg agg gcc tcg caa gcg gcg aag gag gcg gtg gcg ggc      1680
Ser Glu Trp Met Arg Ala Ser Gln Ala Ala Lys Glu Ala Val Ala Gly
545                 550                 555                 560

tag                                                                  1683

<210> SEQ ID NO 2
<211> LENGTH: 560
<212> TYPE: PRT
<213> ORGANISM: Arthrobacter globiformis

<400> SEQUENCE: 2

Met Thr Ser Leu Thr Val Ser Gly Arg Val Ala Gln Val Leu Ser Ser
1               5                   10                  15

Tyr Val Ser Asp Val Phe Gly Val Met Gly Asn Gly Asn Val Tyr Phe
            20                  25                  30

Leu Asp Ala Ala Glu Lys Glu Gly Leu Arg Phe Thr Ala Val Arg His
        35                  40                  45

Glu Gly Ala Ala Ile Ala Ala Ala Asp Ala Tyr Tyr Arg Ala Ser Gly
    50                  55                  60

Arg Leu Ala Ala Gly Thr Thr Thr Tyr Gly Pro Gly Tyr Thr Asn Ala
65                  70                  75                  80

Leu Thr Ala Leu Ala Glu Ala Val Gln Ala Gln Ile Pro Val Val Leu
                85                  90                  95

Val Thr Gly Asp Ala Pro Ser Ser Gly Ala Arg Pro Trp Asp Val Asp
            100                 105                 110

Gln Ala Ala Ile Ala Ala Gly Leu Gly Ala Ala Thr Phe Thr Val Thr
        115                 120                 125

Arg Glu Ala Ala Gly Ser Ile Thr Gln Glu Ala Val Glu Tyr Ala Leu
    130                 135                 140

Ala Arg Arg Thr Ala Val Val Ile Ala Val Pro Tyr Asp Leu Ser Ala
145                 150                 155                 160

Leu Glu Ala Ala Glu Glu Asp Leu Pro Val Pro Pro Ala Ala Ser Val
                165                 170                 175
```

```
Pro Asp Ala Ile Gly Gly Gly Leu Gly Arg Ala Ala Glu Val Arg Ala
            180                 185                 190

Ala Glu Leu Leu Ala Gly Ala Lys Arg Pro Leu Ile Leu Ala Gly Arg
        195                 200                 205

Gly Ala His Leu Ala Gly Ala Gly Pro Glu Leu Arg Glu Leu Ala Asp
    210                 215                 220

Arg Leu Gly Ala Leu Thr Ala Gly Thr Ala Leu Ala Leu Asn Leu Leu
225                 230                 235                 240

Gln Gly Glu Gly Tyr Leu Gly Val Ala Gly Gly Phe Gly Thr Asp Thr
                245                 250                 255

Ala Ala Gly Leu Met Gly Glu Ala Asp Val Val Leu Val Ala Gly Ala
            260                 265                 270

Ser Leu Thr Pro Phe Thr Met Arg Phe Gly His Leu Ile Gly Pro Asp
        275                 280                 285

Ala Thr Val Ile Gln Ile Asp Thr Ala Met Glu Pro Thr Asp Pro Arg
    290                 295                 300

Val Asp Leu Phe Val Ser Ala Asp Ala Lys Ala Ala Ala Gly Arg Ile
305                 310                 315                 320

Leu Arg Leu Leu Asp Asp Ala Ala Gly Ala Asn Ala Ser Lys Ala Trp
                325                 330                 335

Arg Ala Glu Ala Leu Lys Arg Leu Ala Glu Gly Pro Cys His His Pro
            340                 345                 350

Gly Thr Ala Glu Thr Thr Asp Gly Arg Leu Asp Pro Arg Ala Leu Ala
        355                 360                 365

Ser Ala Leu Asp Ala Val Leu Pro Glu Arg Arg Thr Val Val Gln Asp
    370                 375                 380

Gly Gly His Phe Leu Gly Trp Ala Pro Met Tyr Trp Arg Ile Pro Arg
385                 390                 395                 400

Pro Gln Asp Leu Val Met Val Gly Thr Ala Tyr Gln Ser Ile Gly Leu
                405                 410                 415

Gly Leu Ala Ser Ala Val Gly Ala Ser Arg Ala Val Asp Asp Gly Asn
            420                 425                 430

Ile Leu Val Leu Ala Ala Gly Asp Gly Gly Phe Leu Met Gly Leu Ser
        435                 440                 445

Asp Leu Glu Ser Leu Val Gly Ala Ala Ser Ser Ala Val Val Val Ile
    450                 455                 460

Tyr Asn Asp Ala Ala Tyr Gly Ala Glu Ile His Gln Tyr Gly Ser Arg
465                 470                 475                 480

Gly Leu Thr Glu Lys Pro Met Leu Ile Pro Glu Val Asp Phe Ser Gly
                485                 490                 495

Ile Ala Arg Ala Ile Gly Ala Glu Ser Ala Ile Ile Arg Lys Leu Ser
            500                 505                 510

Asp Leu Ser Ala Leu Thr Asp Trp Ile Glu Ala Gly Ala Arg Gly Thr
        515                 520                 525

Phe Val Ala Asp Cys Arg Ile Thr Ser Ser Val Arg Ala Pro Trp Leu
    530                 535                 540

Ser Glu Trp Met Arg Ala Ser Gln Ala Ala Lys Glu Ala Val Ala Gly
545                 550                 555                 560
```

```
<210> SEQ ID NO 3
<211> LENGTH: 1944
<212> TYPE: DNA
<213> ORGANISM: Artificial
<220> FEATURE:
<221> NAME/KEY: CDS
```

```
<222> LOCATION: (55)..(1737)
<223> OTHER INFORMATION: A. globiformis HPPO mutant

<400> SEQUENCE: 3

ccgacgtcgc atgctcccgg ccgccatggc ggccgcggga attcgattga attc atg      57
                                                            Met
                                                            1

act tca ctt aca gtg tcc ggc cgg gtg gcg cag gtc ctc agc agc tat     105
Thr Ser Leu Thr Val Ser Gly Arg Val Ala Gln Val Leu Ser Ser Tyr
            5                   10                  15

gtc agc gat gtg ttc ggt gtg atg ggc aac gga aac gtc tac ttc ctg     153
Val Ser Asp Val Phe Gly Val Met Gly Asn Gly Asn Val Tyr Phe Leu
        20                  25                  30

gac gcc gcc gag aag gag ggc ctc cgc ttc acg gcc gta cgc cat gaa     201
Asp Ala Ala Glu Lys Glu Gly Leu Arg Phe Thr Ala Val Arg His Glu
    35                  40                  45

ggt gcc gcc atc gcg gcg gcg gac gcc tac tat cgg gca tcc ggg cgc     249
Gly Ala Ala Ile Ala Ala Ala Asp Ala Tyr Tyr Arg Ala Ser Gly Arg
50                  55                  60                  65

ctg gcg gcg ggg acc acc acc tac ggc ccc ggt tac acc aac gcc ctg     297
Leu Ala Ala Gly Thr Thr Thr Tyr Gly Pro Gly Tyr Thr Asn Ala Leu
                70                  75                  80

acg gcc ctc gcc gag gcg gtc cag gcg cag atc ccc gtg gtg ctc gtc     345
Thr Ala Leu Ala Glu Ala Val Gln Ala Gln Ile Pro Val Val Leu Val
            85                  90                  95

acc ggg gac gcc ccg agc agc ggc gcc cgg cct tgg gac gtg gac cag     393
Thr Gly Asp Ala Pro Ser Ser Gly Ala Arg Pro Trp Asp Val Asp Gln
        100                 105                 110

gcc gcg atc gcc gcc ggg ctg ggg gcg gcg acc ttc acg gtc acc cgt     441
Ala Ala Ile Ala Ala Gly Leu Gly Ala Ala Thr Phe Thr Val Thr Arg
    115                 120                 125

gaa gcc gca ggc tcc atc acg cag gaa gcg gtg gag tac gca ctt gcc     489
Glu Ala Ala Gly Ser Ile Thr Gln Glu Ala Val Glu Tyr Ala Leu Ala
130                 135                 140                 145

cgg cgg acc gcc gtc gtg atc gcc gtt cca tac gac ctg tcg gcc ctt     537
Arg Arg Thr Ala Val Val Ile Ala Val Pro Tyr Asp Leu Ser Ala Leu
                150                 155                 160

gag gcg gcg gag gaa gat ctt ccc gtg ccg ccg gcg gcc tcg gtt ccg     585
Glu Ala Ala Glu Glu Asp Leu Pro Val Pro Pro Ala Ala Ser Val Pro
            165                 170                 175

gac gcc atc ggc ggc gga ctc gga cgg gcg gcc gaa gtg cgg gcg gcc     633
Asp Ala Ile Gly Gly Gly Leu Gly Arg Ala Ala Glu Val Arg Ala Ala
        180                 185                 190

gaa ttg ctg gcg ggc gcg aag cgg ccg ctc atc ctt gcc ggc cgc ggt     681
Glu Leu Leu Ala Gly Ala Lys Arg Pro Leu Ile Leu Ala Gly Arg Gly
    195                 200                 205

gcg cac ctc gca gga acc ggc ccc gaa ctc cgg gaa ctc gcc gac cgc     729
Ala His Leu Ala Gly Thr Gly Pro Glu Leu Arg Glu Leu Ala Asp Arg
210                 215                 220                 225

ctc ggc gcg ctc acg gcc ggc acc gca ctg gcg ctg aac ctg ctg cag     777
Leu Gly Ala Leu Thr Ala Gly Thr Ala Leu Ala Leu Asn Leu Leu Gln
                230                 235                 240

ggc gag ggg tac ctc ggc gtc gcg ggc ggc ttc ggc acg gat acc gcc     825
Gly Glu Gly Tyr Leu Gly Val Ala Gly Gly Phe Gly Thr Asp Thr Ala
            245                 250                 255

gcc ggg ctc atg ggc gag gcg gac gtg gtg ctc gtg gcg gga gcc agc     873
Ala Gly Leu Met Gly Glu Ala Asp Val Val Leu Val Ala Gly Ala Ser
        260                 265                 270

ctg acc ccc ttc acc atg cgc ttc ggc cac ctg atc ggc ccg gac gcc     921
Leu Thr Pro Phe Thr Met Arg Phe Gly His Leu Ile Gly Pro Asp Ala
    275                 280                 285
```

```
acc gtg atc cag atc gac acc gcc atg gag ccg acg gac ccg cgg gtg      969
Thr Val Ile Gln Ile Asp Thr Ala Met Glu Pro Thr Asp Pro Arg Val
290                 295                 300                 305

gac ctg ttt gtc agt gcg gac gcg aag gcc gct gcc ggc cgg atc ctc     1017
Asp Leu Phe Val Ser Ala Asp Ala Lys Ala Ala Ala Gly Arg Ile Leu
                310                 315                 320

cgg ctg ctg gat gac gcc gcc ggg gcc aat gcg tcg aag gcc tgg cgc     1065
Arg Leu Leu Asp Asp Ala Ala Gly Ala Asn Ala Ser Lys Ala Trp Arg
            325                 330                 335

gcg gaa gca ctc aag cgt ctg gcc gaa gga ccc tgc cac cac ccc ggc     1113
Ala Glu Ala Leu Lys Arg Leu Ala Glu Gly Pro Cys His His Pro Gly
        340                 345                 350

acc gca gag acc acg gac ggc cgc ctt gac ccc cgg gcg ctt gct tcg     1161
Thr Ala Glu Thr Thr Asp Gly Arg Leu Asp Pro Arg Ala Leu Ala Ser
    355                 360                 365

gca ctg gat gcc gtc ctg ccg gaa cgc cgc acc gtg gtc cag gac ggc     1209
Ala Leu Asp Ala Val Leu Pro Glu Arg Arg Thr Val Val Gln Asp Gly
370                 375                 380                 385

ggg cac ttc ctg ggc tgg gca ccc atg tac tgg cgc atc ccc cgt cct     1257
Gly His Phe Leu Gly Trp Ala Pro Met Tyr Trp Arg Ile Pro Arg Pro
                390                 395                 400

cag gac ctg gtc atg gtg ggg acc gcg tac cag tcg atc ggg ctt ggc     1305
Gln Asp Leu Val Met Val Gly Thr Ala Tyr Gln Ser Ile Gly Leu Gly
            405                 410                 415

ctg gcc agc gcc gtg ggg gcg tcc cgg gcc gtg gac gac ggc aat atc     1353
Leu Ala Ser Ala Val Gly Ala Ser Arg Ala Val Asp Asp Gly Asn Ile
        420                 425                 430

ctg gtg ctg gcg gcg ggc gac ggc gga ttc ctg atg ggc ctg tcc gac     1401
Leu Val Leu Ala Ala Gly Asp Gly Gly Phe Leu Met Gly Leu Ser Asp
    435                 440                 445

ctg gaa tcg ctc gtg ggc gcg gcg agc agc gcc gtc gtg gtg atc tac     1449
Leu Glu Ser Leu Val Gly Ala Ala Ser Ser Ala Val Val Val Ile Tyr
450                 455                 460                 465

aac gac gcc gcc tac ggg gcc gag atc cat cag tac ggc tca cgg ggg     1497
Asn Asp Ala Ala Tyr Gly Ala Glu Ile His Gln Tyr Gly Ser Arg Gly
                470                 475                 480

ctc acc gaa aag ccc atg ctg atc ccc gaa gtg gac ttc agc ggg att     1545
Leu Thr Glu Lys Pro Met Leu Ile Pro Glu Val Asp Phe Ser Gly Ile
            485                 490                 495

gcc cgc gcg atc ggg gcg gaa tcc gca atc atc cgc aag ctg tcg gac     1593
Ala Arg Ala Ile Gly Ala Glu Ser Ala Ile Ile Arg Lys Leu Ser Asp
        500                 505                 510

ctc tcc gcg ctc acg gac tgg atc gag gcc ggc gcc agg gga acc ttc     1641
Leu Ser Ala Leu Thr Asp Trp Ile Glu Ala Gly Ala Arg Gly Thr Phe
    515                 520                 525

gtg gcc gac tgc cgc atc acc tca agc gtc cgg gcc ccg tgg ctg agc     1689
Val Ala Asp Cys Arg Ile Thr Ser Ser Val Arg Ala Pro Trp Leu Ser
530                 535                 540                 545

gaa tgg atg agg gcc tcg caa gcg gcg aag gag gcg gtg gcg ggc tag     1737
Glu Trp Met Arg Ala Ser Gln Ala Ala Lys Glu Ala Val Ala Gly
                550                 555                 560

ggccggcctc gtcgaaatgc cgccctccaa cccaactcag taccagctca gggcgttctc   1797

agggctggga acgccctgag ctgctactca tttgttcgaa ctcgagaatt caatcactag   1857

tgaattcgcg gccgcctgca ggtcgaccat atgggagagc tcccaacgcg ttggatgcat   1917

agcttgagta ttctatagtg tcaccta                                       1944
```

<210> SEQ ID NO 4
<211> LENGTH: 560

<212> TYPE: PRT
<213> ORGANISM: Artificial
<220> FEATURE:
<223> OTHER INFORMATION: A. Globiformis HPPO mutant

<400> SEQUENCE: 4

```
Met Thr Ser Leu Thr Val Ser Gly Arg Val Ala Gln Val Leu Ser Ser
1               5                   10                  15

Tyr Val Ser Asp Val Phe Gly Val Met Gly Asn Gly Asn Val Tyr Phe
            20                  25                  30

Leu Asp Ala Ala Glu Lys Glu Gly Leu Arg Phe Thr Ala Val Arg His
        35                  40                  45

Glu Gly Ala Ala Ile Ala Ala Ala Asp Ala Tyr Tyr Arg Ala Ser Gly
    50                  55                  60

Arg Leu Ala Ala Gly Thr Thr Thr Tyr Gly Pro Gly Tyr Thr Asn Ala
65                  70                  75                  80

Leu Thr Ala Leu Ala Glu Ala Val Gln Ala Gln Ile Pro Val Val Leu
                85                  90                  95

Val Thr Gly Asp Ala Pro Ser Ser Gly Ala Arg Pro Trp Asp Val Asp
            100                 105                 110

Gln Ala Ala Ile Ala Ala Gly Leu Gly Ala Ala Thr Phe Thr Val Thr
        115                 120                 125

Arg Glu Ala Ala Gly Ser Ile Thr Gln Glu Ala Val Glu Tyr Ala Leu
    130                 135                 140

Ala Arg Arg Thr Ala Val Val Ile Ala Val Pro Tyr Asp Leu Ser Ala
145                 150                 155                 160

Leu Glu Ala Ala Glu Glu Asp Leu Pro Val Pro Pro Ala Ala Ser Val
                165                 170                 175

Pro Asp Ala Ile Gly Gly Gly Leu Gly Arg Ala Ala Glu Val Arg Ala
            180                 185                 190

Ala Glu Leu Leu Ala Gly Ala Lys Arg Pro Leu Ile Leu Ala Gly Arg
        195                 200                 205

Gly Ala His Leu Ala Gly Thr Gly Pro Glu Leu Arg Glu Leu Ala Asp
    210                 215                 220

Arg Leu Gly Ala Leu Thr Ala Gly Thr Ala Leu Ala Leu Asn Leu Leu
225                 230                 235                 240

Gln Gly Glu Gly Tyr Leu Gly Val Ala Gly Gly Phe Gly Thr Asp Thr
                245                 250                 255

Ala Ala Gly Leu Met Gly Glu Ala Asp Val Val Leu Val Ala Gly Ala
            260                 265                 270

Ser Leu Thr Pro Phe Thr Met Arg Phe Gly His Leu Ile Gly Pro Asp
        275                 280                 285

Ala Thr Val Ile Gln Ile Asp Thr Ala Met Glu Pro Thr Asp Pro Arg
    290                 295                 300

Val Asp Leu Phe Val Ser Ala Asp Ala Lys Ala Ala Ala Gly Arg Ile
305                 310                 315                 320

Leu Arg Leu Leu Asp Asp Ala Ala Gly Ala Asn Ala Ser Lys Ala Trp
                325                 330                 335

Arg Ala Glu Ala Leu Lys Arg Leu Ala Glu Gly Pro Cys His His Pro
            340                 345                 350

Gly Thr Ala Glu Thr Thr Asp Gly Arg Leu Asp Pro Arg Ala Leu Ala
        355                 360                 365

Ser Ala Leu Asp Ala Val Leu Pro Glu Arg Arg Thr Val Val Gln Asp
    370                 375                 380

Gly Gly His Phe Leu Gly Trp Ala Pro Met Tyr Trp Arg Ile Pro Arg
```

```
385                 390                 395                 400

Pro Gln Asp Leu Val Met Val Gly Thr Ala Tyr Gln Ser Ile Gly Leu
                405                 410                 415

Gly Leu Ala Ser Ala Val Gly Ala Ser Arg Ala Val Asp Asp Gly Asn
            420                 425                 430

Ile Leu Val Leu Ala Ala Gly Asp Gly Gly Phe Leu Met Gly Leu Ser
        435                 440                 445

Asp Leu Glu Ser Leu Val Gly Ala Ala Ser Ser Ala Val Val Val Ile
    450                 455                 460

Tyr Asn Asp Ala Ala Tyr Gly Ala Glu Ile His Gln Tyr Gly Ser Arg
465                 470                 475                 480

Gly Leu Thr Glu Lys Pro Met Leu Ile Pro Glu Val Asp Phe Ser Gly
                485                 490                 495

Ile Ala Arg Ala Ile Gly Ala Glu Ser Ala Ile Ile Arg Lys Leu Ser
            500                 505                 510

Asp Leu Ser Ala Leu Thr Asp Trp Ile Glu Ala Gly Ala Arg Gly Thr
        515                 520                 525

Phe Val Ala Asp Cys Arg Ile Thr Ser Ser Val Arg Ala Pro Trp Leu
    530                 535                 540

Ser Glu Trp Met Arg Ala Ser Gln Ala Ala Lys Glu Ala Val Ala Gly
545                 550                 555                 560


<210> SEQ ID NO 5
<211> LENGTH: 1962
<212> TYPE: DNA
<213> ORGANISM: Artificial
<220> FEATURE:
<221> NAME/KEY: CDS
<222> LOCATION: (111)..(1793)
<223> OTHER INFORMATION: A. globiformis HPPO mutant

<400> SEQUENCE: 5

aggtgacact atagaatact caagctatgc atccaacgcg ttgggagctc tcccatatgg      60

tcgacctgca ggcggccgcg aattcactag tgattggaag gatccggtgc atg act        116
                                                       Met Thr
                                                       1

tca ctt aca gtg tcc ggc cgg gtg gcg cag gtc ctc agc agc tat gtc       164
Ser Leu Thr Val Ser Gly Arg Val Ala Gln Val Leu Ser Ser Tyr Val
        5                   10                  15

agc gat gtg ttc ggt gtg atg ggc aac gga aac gtc tac ttc ctg gac       212
Ser Asp Val Phe Gly Val Met Gly Asn Gly Asn Val Tyr Phe Leu Asp
    20                  25                  30

gcc gcc gag aag gag ggc ctc cgc ttc acg gcc gta cgc cat gaa ggt       260
Ala Ala Glu Lys Glu Gly Leu Arg Phe Thr Ala Val Arg His Glu Gly
35                  40                  45                  50

gcc gcc atc gcg gcg gcg gac gcc tac tat cgg gca tcc ggg cgc ctg       308
Ala Ala Ile Ala Ala Ala Asp Ala Tyr Tyr Arg Ala Ser Gly Arg Leu
                55                  60                  65

gcg gcg ggg acc acc acc tac ggc ccc ggt tac acc aac gcc ctg acg       356
Ala Ala Gly Thr Thr Thr Tyr Gly Pro Gly Tyr Thr Asn Ala Leu Thr
            70                  75                  80

gcc ctc gcc gag gcg gtc cag gcg cag atc ccc gtg gtg ctc gtc acc       404
Ala Leu Ala Glu Ala Val Gln Ala Gln Ile Pro Val Val Leu Val Thr
        85                  90                  95

ggg gac gcc ccg agc agc ggc gcc cgg cct tgg gac gtg gac cag gcc       452
Gly Asp Ala Pro Ser Ser Gly Ala Arg Pro Trp Asp Val Asp Gln Ala
    100                 105                 110

gcg atc gcc ggc ggg ctg ggg gcg gcg acc ttc acg gtc acc cgt gaa       500
Ala Ile Ala Gly Gly Leu Gly Ala Ala Thr Phe Thr Val Thr Arg Glu
```

```
115                 120                 125                 130

gcc gca ggc tcc atc acg cag gaa gcg gtg gag tac gca ctt gcc cgg      548
Ala Ala Gly Ser Ile Thr Gln Glu Ala Val Glu Tyr Ala Leu Ala Arg
                135                 140                 145

cgg acc gcc gtc gtg atc gcc gtt cca tac gac ctg tcg gcc ctt gag      596
Arg Thr Ala Val Val Ile Ala Val Pro Tyr Asp Leu Ser Ala Leu Glu
            150                 155                 160

gcg gca gag gaa gat ctt ccc gtg ccg ccg gcg gcc tcg gtt ccg gac      644
Ala Ala Glu Glu Asp Leu Pro Val Pro Pro Ala Ala Ser Val Pro Asp
        165                 170                 175

gcc atc ggc ggc gga ctc gga cgg gcg gcc gaa gtg cgg gcg gcc gaa      692
Ala Ile Gly Gly Gly Leu Gly Arg Ala Ala Glu Val Arg Ala Ala Glu
    180                 185                 190

ttg ctg gcg ggc gcg aag cgg ccg ctc atc ctt gcc ggc cgc ggt gcg      740
Leu Leu Ala Gly Ala Lys Arg Pro Leu Ile Leu Ala Gly Arg Gly Ala
195                 200                 205                 210

cac ctc gca gga gcc ggc ccc gaa ctc cgg gaa ctc gcc gac cgc ctc      788
His Leu Ala Gly Ala Gly Pro Glu Leu Arg Glu Leu Ala Asp Arg Leu
                215                 220                 225

ggc gcg ctc acg gcc ggc acc gca ctg gcg ctg aac ctg ctg cag ggc      836
Gly Ala Leu Thr Ala Gly Thr Ala Leu Ala Leu Asn Leu Leu Gln Gly
            230                 235                 240

gag ggg tac ctc ggc gtc gcg ggc ggc ttc ggc acg gat acc gcc gcc      884
Glu Gly Tyr Leu Gly Val Ala Gly Gly Phe Gly Thr Asp Thr Ala Ala
        245                 250                 255

ggg ctc atg ggc gag gcg gac gtg gtg ctc gtg gcg gga gcc agc ctg      932
Gly Leu Met Gly Glu Ala Asp Val Val Leu Val Ala Gly Ala Ser Leu
    260                 265                 270

acc ccc ttc acc atg cgc ttc ggc cac ctg atc ggc ccg gac gcc acc      980
Thr Pro Phe Thr Met Arg Phe Gly His Leu Ile Gly Pro Asp Ala Thr
275                 280                 285                 290

gtg atc cag atc gac acc gcc atg gag ccg acg gac ccg cgg gtg gac     1028
Val Ile Gln Ile Asp Thr Ala Met Glu Pro Thr Asp Pro Arg Val Asp
                295                 300                 305

ctg ttt gtc agt gcg gac gcg aag gcc gct gcc ggc cgg atc ctc cgg     1076
Leu Phe Val Ser Ala Asp Ala Lys Ala Ala Ala Gly Arg Ile Leu Arg
            310                 315                 320

ctg ctg gat gac gcc gcc ggg gcc aat gcg tcg aag gcc tgg cgc gcg     1124
Leu Leu Asp Asp Ala Ala Gly Ala Asn Ala Ser Lys Ala Trp Arg Ala
        325                 330                 335

gaa gca ctc aag cgt ctg gcc gaa gga ccc tgc cac cac ccc ggc acc     1172
Glu Ala Leu Lys Arg Leu Ala Glu Gly Pro Cys His His Pro Gly Thr
    340                 345                 350

gca gag acc acg gac ggc cgc ctt gac ccc cgg gcg ctt gct tcg gca     1220
Ala Glu Thr Thr Asp Gly Arg Leu Asp Pro Arg Ala Leu Ala Ser Ala
355                 360                 365                 370

ctg gat gcc gtc ctg ccg gaa cgc cgc acc gtg gtc cag gac ggc ggg     1268
Leu Asp Ala Val Leu Pro Glu Arg Arg Thr Val Val Gln Asp Gly Gly
                375                 380                 385

cac ttc ctg ggc tgg gca ccc atg tac tgg cgc atc ccc cgt cct cag     1316
His Phe Leu Gly Trp Ala Pro Met Tyr Trp Arg Ile Pro Arg Pro Gln
            390                 395                 400

gac ctg gtc atg gtg ggg acc gcg tac cag tcg atc ggg ctt ggc ctg     1364
Asp Leu Val Met Val Gly Thr Ala Tyr Gln Ser Ile Gly Leu Gly Leu
        405                 410                 415

gcc agc gcc gtg ggg gcg tcc cgg gcc gtg gac gac ggc aat atc ctg     1412
Ala Ser Ala Val Gly Ala Ser Arg Ala Val Asp Asp Gly Asn Ile Leu
    420                 425                 430

gtg ctg gcg gcg ggc gac ggc gga ttc ctg atg ggc ctg tcc gac ctg     1460
Val Leu Ala Ala Gly Asp Gly Gly Phe Leu Met Gly Leu Ser Asp Leu
```

```
435                 440                 445                 450

gaa tcg ctc gtg ggc gcg gcg agc agc gcc gtc gtg gtg atc tac aac      1508
Glu Ser Leu Val Gly Ala Ala Ser Ser Ala Val Val Val Ile Tyr Asn
            455                 460                 465

gat gcc gcc tac ggg gcc gag atc cat cag tac ggc tca cgg ggg ctc      1556
Asp Ala Ala Tyr Gly Ala Glu Ile His Gln Tyr Gly Ser Arg Gly Leu
            470                 475                 480

acc gaa aag ccc atg ctg atc ccc gaa gtg gac ttc agc ggg att gcc      1604
Thr Glu Lys Pro Met Leu Ile Pro Glu Val Asp Phe Ser Gly Ile Ala
        485                 490                 495

cgc gcg atc ggg gcg gaa tcc gca atc atc cgc aag ctg tcg gac ctc      1652
Arg Ala Ile Gly Ala Glu Ser Ala Ile Ile Arg Lys Leu Ser Asp Leu
    500                 505                 510

tcc gcg ctc acg gac tgg atc gag gcc ggc gcc agg gga acc ttc gtg      1700
Ser Ala Leu Thr Asp Trp Ile Glu Ala Gly Ala Arg Gly Thr Phe Val
515                 520                 525                 530

gcc gac tgc cgc atc acc tca agc gtc cgg gcc ccg tgg ctg agc gaa      1748
Ala Asp Cys Arg Ile Thr Ser Ser Val Arg Ala Pro Trp Leu Ser Glu
            535                 540                 545

tgg atg agg gcc tcg caa gcg gcg aag gag gcg gtg gcg ggc tag          1793
Trp Met Arg Ala Ser Gln Ala Ala Lys Glu Ala Val Ala Gly
            550                 555                 560

ggccggcctc gtcgaaatgc cgccctccaa cccaactcag taccagctca gggcgttctc   1853

agggctggga acgccctgag ctgctactca gtttgttcga actcgagaat tcaatcgaat   1913

tcccgcggcc gccatggcgg ccgggagcat gcgacgtcgg gcccattcg               1962


<210> SEQ ID NO 6
<211> LENGTH: 560
<212> TYPE: PRT
<213> ORGANISM: Artificial
<220> FEATURE:
<223> OTHER INFORMATION: A. Globiformis HPPO mutant

<400> SEQUENCE: 6

Met Thr Ser Leu Thr Val Ser Gly Arg Val Ala Gln Val Leu Ser Ser
1               5                   10                  15

Tyr Val Ser Asp Val Phe Gly Val Met Gly Asn Gly Asn Val Tyr Phe
            20                  25                  30

Leu Asp Ala Ala Glu Lys Glu Gly Leu Arg Phe Thr Ala Val Arg His
        35                  40                  45

Glu Gly Ala Ala Ile Ala Ala Ala Asp Ala Tyr Tyr Arg Ala Ser Gly
    50                  55                  60

Arg Leu Ala Ala Gly Thr Thr Thr Tyr Gly Pro Gly Tyr Thr Asn Ala
65                  70                  75                  80

Leu Thr Ala Leu Ala Glu Ala Val Gln Ala Gln Ile Pro Val Val Leu
                85                  90                  95

Val Thr Gly Asp Ala Pro Ser Ser Gly Ala Arg Pro Trp Asp Val Asp
            100                 105                 110

Gln Ala Ala Ile Ala Gly Gly Leu Gly Ala Ala Thr Phe Thr Val Thr
        115                 120                 125

Arg Glu Ala Ala Gly Ser Ile Thr Gln Glu Ala Val Glu Tyr Ala Leu
    130                 135                 140

Ala Arg Arg Thr Ala Val Val Ile Ala Val Pro Tyr Asp Leu Ser Ala
145                 150                 155                 160

Leu Glu Ala Ala Glu Glu Asp Leu Pro Val Pro Pro Ala Ala Ser Val
                165                 170                 175

Pro Asp Ala Ile Gly Gly Gly Leu Gly Arg Ala Ala Glu Val Arg Ala
```

```
            180                 185                 190

Ala Glu Leu Leu Ala Gly Ala Lys Arg Pro Leu Ile Leu Ala Gly Arg
        195                 200                 205

Gly Ala His Leu Ala Gly Ala Gly Pro Glu Leu Arg Glu Leu Ala Asp
    210                 215                 220

Arg Leu Gly Ala Leu Thr Ala Gly Thr Ala Leu Ala Leu Asn Leu Leu
225                 230                 235                 240

Gln Gly Glu Gly Tyr Leu Gly Val Ala Gly Gly Phe Gly Thr Asp Thr
                245                 250                 255

Ala Ala Gly Leu Met Gly Glu Ala Asp Val Val Leu Val Ala Gly Ala
            260                 265                 270

Ser Leu Thr Pro Phe Thr Met Arg Phe Gly His Leu Ile Gly Pro Asp
        275                 280                 285

Ala Thr Val Ile Gln Ile Asp Thr Ala Met Glu Pro Thr Asp Pro Arg
    290                 295                 300

Val Asp Leu Phe Val Ser Ala Asp Ala Lys Ala Ala Ala Gly Arg Ile
305                 310                 315                 320

Leu Arg Leu Leu Asp Asp Ala Ala Gly Ala Asn Ala Ser Lys Ala Trp
                325                 330                 335

Arg Ala Glu Ala Leu Lys Arg Leu Ala Glu Gly Pro Cys His His Pro
            340                 345                 350

Gly Thr Ala Glu Thr Thr Asp Gly Arg Leu Asp Pro Arg Ala Leu Ala
        355                 360                 365

Ser Ala Leu Asp Ala Val Leu Pro Glu Arg Arg Thr Val Val Gln Asp
    370                 375                 380

Gly Gly His Phe Leu Gly Trp Ala Pro Met Tyr Trp Arg Ile Pro Arg
385                 390                 395                 400

Pro Gln Asp Leu Val Met Val Gly Thr Ala Tyr Gln Ser Ile Gly Leu
                405                 410                 415

Gly Leu Ala Ser Ala Val Gly Ala Ser Arg Ala Val Asp Asp Gly Asn
            420                 425                 430

Ile Leu Val Leu Ala Ala Gly Asp Gly Gly Phe Leu Met Gly Leu Ser
        435                 440                 445

Asp Leu Glu Ser Leu Val Gly Ala Ala Ser Ser Ala Val Val Val Ile
    450                 455                 460

Tyr Asn Asp Ala Ala Tyr Gly Ala Glu Ile His Gln Tyr Gly Ser Arg
465                 470                 475                 480

Gly Leu Thr Glu Lys Pro Met Leu Ile Pro Glu Val Asp Phe Ser Gly
                485                 490                 495

Ile Ala Arg Ala Ile Gly Ala Glu Ser Ala Ile Ile Arg Lys Leu Ser
            500                 505                 510

Asp Leu Ser Ala Leu Thr Asp Trp Ile Glu Ala Gly Ala Arg Gly Thr
        515                 520                 525

Phe Val Ala Asp Cys Arg Ile Thr Ser Ser Val Arg Ala Pro Trp Leu
    530                 535                 540

Ser Glu Trp Met Arg Ala Ser Gln Ala Ala Lys Glu Ala Val Ala Gly
545                 550                 555                 560
```

<210> SEQ ID NO 7
<211> LENGTH: 1692
<212> TYPE: DNA
<213> ORGANISM: Pseudomonas acidivorans
<220> FEATURE:
<221> NAME/KEY: CDS
<222> LOCATION: (1)..(1692)

<400> SEQUENCE: 7

```
atg tcc cac ccc gcc atc tcc ctg caa gcg ctg cgc ggc agc ggc gca       48
Met Ser His Pro Ala Ile Ser Leu Gln Ala Leu Arg Gly Ser Gly Ala
1               5                   10                  15

gac ata cag tcc atc cac atc ccc tac gag cgc cat gcc gac cag gac       96
Asp Ile Gln Ser Ile His Ile Pro Tyr Glu Arg His Ala Asp Gln Asp
            20                  25                  30

gcc ggt gcg gac acg ccc gcc cgg cat ccc gtc gtc atc gtc ggc gcc      144
Ala Gly Ala Asp Thr Pro Ala Arg His Pro Val Val Ile Val Gly Ala
        35                  40                  45

ggc ccc gtg ggc ctg tcg ctg gcc atc gac ctg gcc cag cgc ggc cag      192
Gly Pro Val Gly Leu Ser Leu Ala Ile Asp Leu Ala Gln Arg Gly Gln
    50                  55                  60

cgc gtg gtg ctg ctg gac aac gac tgc cgg ctg tcc acg ggc tcg cgc      240
Arg Val Val Leu Leu Asp Asn Asp Cys Arg Leu Ser Thr Gly Ser Arg
65                  70                  75                  80

gcc atc tgc ttt tcc aag cgc acg ctg gag atc tgg gac cgc ctg ggc      288
Ala Ile Cys Phe Ser Lys Arg Thr Leu Glu Ile Trp Asp Arg Leu Gly
                85                  90                  95

gtg ggc cag ccc atg gtg gac aag ggc gtg tcc tgg aac ctg ggc aag      336
Val Gly Gln Pro Met Val Asp Lys Gly Val Ser Trp Asn Leu Gly Lys
            100                 105                 110

gtc ttc ttc aag gac cag ccg ctg tac cgc ttc gac ctg ctg ccc gag      384
Val Phe Phe Lys Asp Gln Pro Leu Tyr Arg Phe Asp Leu Leu Pro Glu
        115                 120                 125

gac ggc cac gag cgc ccg gcc ttc atc aac ctg cag cag tac tac gcc      432
Asp Gly His Glu Arg Pro Ala Phe Ile Asn Leu Gln Gln Tyr Tyr Ala
    130                 135                 140

gag gcc tat ctg gtc gag cgc gca ctg cag ctg ccg ctg atc gac ctg      480
Glu Ala Tyr Leu Val Glu Arg Ala Leu Gln Leu Pro Leu Ile Asp Leu
145                 150                 155                 160

cgc tgg cac agc aag gtc acg gca ctg gag ccg cag gcc gag ggc gcg      528
Arg Trp His Ser Lys Val Thr Ala Leu Glu Pro Gln Ala Glu Gly Ala
                165                 170                 175

ctg ctg acc gtg gag acg cct gac ggc agc tac cgc atc gat gcg caa      576
Leu Leu Thr Val Glu Thr Pro Asp Gly Ser Tyr Arg Ile Asp Ala Gln
            180                 185                 190

tgg gtc ctg gcc tgc gat ggc tcg cgc tcg ccg ctg cgc ggc ctg ctg      624
Trp Val Leu Ala Cys Asp Gly Ser Arg Ser Pro Leu Arg Gly Leu Leu
        195                 200                 205

ggc cag gaa agc cat ggc cgc atc ttc cgc gac cgc ttc ctg atc gcc      672
Gly Gln Glu Ser His Gly Arg Ile Phe Arg Asp Arg Phe Leu Ile Ala
    210                 215                 220

gac gtg aag atg cac gcc gaa ttc ccc acc gag cgc tgg ttc tgg ttc      720
Asp Val Lys Met His Ala Glu Phe Pro Thr Glu Arg Trp Phe Trp Phe
225                 230                 235                 240

gac ccg ccc ttc cac ccg ggc cag agc gtg ctg ctg cac cgc cag ccc      768
Asp Pro Pro Phe His Pro Gly Gln Ser Val Leu Leu His Arg Gln Pro
                245                 250                 255

gac gat gtc tgg cgc atc gac ttc cag ctg ggc tgg gac gcg gac ccc      816
Asp Asp Val Trp Arg Ile Asp Phe Gln Leu Gly Trp Asp Ala Asp Pro
            260                 265                 270

gag gaa gag aaa aag ccc gag aac atc gtg ccg cgc atc cgc gcc ctg      864
Glu Glu Glu Lys Lys Pro Glu Asn Ile Val Pro Arg Ile Arg Ala Leu
        275                 280                 285

ctg ggc aag gac gcg ccc ttc gag ctg gaa tgg gcc agc gtc tac acc      912
Leu Gly Lys Asp Ala Pro Phe Glu Leu Glu Trp Ala Ser Val Tyr Thr
    290                 295                 300

ttc gcc tgc ctg cgc atg gac cgc ttc gtc cat ggc cgc gtg gtc ttt      960
Phe Ala Cys Leu Arg Met Asp Arg Phe Val His Gly Arg Val Val Phe
```

```
305                 310                 315                 320

gcg ggc gac agc gcc cac ggc gtc tcg ccg ttt ggc gca cgc ggc gcc      1008
Ala Gly Asp Ser Ala His Gly Val Ser Pro Phe Gly Ala Arg Gly Ala
                325                 330                 335

aac agc ggc gtg cag gat gcc gag aac ctg gca tgg aag ctg gac cgc      1056
Asn Ser Gly Val Gln Asp Ala Glu Asn Leu Ala Trp Lys Leu Asp Arg
            340                 345                 350

gtg ctg cgc ggc cag gcc gat gcc tcg ctg atc gcc acc tac ggc gcc      1104
Val Leu Arg Gly Gln Ala Asp Ala Ser Leu Ile Ala Thr Tyr Gly Ala
        355                 360                 365

gag cgc gaa tac gcg gcc gac gag aac atc cgc aac tcc acg cgc gcc      1152
Glu Arg Glu Tyr Ala Ala Asp Glu Asn Ile Arg Asn Ser Thr Arg Ala
    370                 375                 380

acc gac ttc atc acg ccc aag agc gag atc agc cgc ctg ttt cgc gac      1200
Thr Asp Phe Ile Thr Pro Lys Ser Glu Ile Ser Arg Leu Phe Arg Asp
385                 390                 395                 400

gcc gtg ctg gac ctg gcg cgc gac cat gaa ttc gcg cgc cgc atc gtc      1248
Ala Val Leu Asp Leu Ala Arg Asp His Glu Phe Ala Arg Arg Ile Val
                405                 410                 415

aac agc ggg cgg ctg tcc gtg ccg gcc acg ctg cac ggc tcc gcg ctc      1296
Asn Ser Gly Arg Leu Ser Val Pro Ala Thr Leu His Gly Ser Ala Leu
            420                 425                 430

aac acg cct gac acc gac acc ttc gac gga acg cag ctg ccc ggc gcc      1344
Asn Thr Pro Asp Thr Asp Thr Phe Asp Gly Thr Gln Leu Pro Gly Ala
        435                 440                 445

gtg ctg gcc gat gcg ccc atg cgc cgg ccc ggc gca gac ggc acg gcc      1392
Val Leu Ala Asp Ala Pro Met Arg Arg Pro Gly Ala Asp Gly Thr Ala
    450                 455                 460

tgg ctg ctg cgc gca ctg gga ccg gac ttc acg ctg ctg cac ttc gac      1440
Trp Leu Leu Arg Ala Leu Gly Pro Asp Phe Thr Leu Leu His Phe Asp
465                 470                 475                 480

ccc acg ccc gcc tgg gcg cag gcg ctg ccc ggc gtg ctc aac ctg tcc      1488
Pro Thr Pro Ala Trp Ala Gln Ala Leu Pro Gly Val Leu Asn Leu Ser
                485                 490                 495

atc gcg gcc gag ggc gag gcc cat gcg cca gac gcc gac ctc atc gat      1536
Ile Ala Ala Glu Gly Glu Ala His Ala Pro Asp Ala Asp Leu Ile Asp
            500                 505                 510

gcg cgc ggc ctg gcg gcc aaa cgc ctg gat gca cgc ccc ggc acc agc      1584
Ala Arg Gly Leu Ala Ala Lys Arg Leu Asp Ala Arg Pro Gly Thr Ser
        515                 520                 525

tac ctg ctg cgg cct gac cag cat gtc tgc gcg cgc tgg cgc cgc ccc      1632
Tyr Leu Leu Arg Pro Asp Gln His Val Cys Ala Arg Trp Arg Arg Pro
    530                 535                 540

gac gaa gcc agc gtg cgc gcc gcg ctg caa aga gcc tgc ggc gcc gcc      1680
Asp Glu Ala Ser Val Arg Ala Ala Leu Gln Arg Ala Cys Gly Ala Ala
545                 550                 555                 560

gcc acg gcc tga                                                      1692
Ala Thr Ala


<210> SEQ ID NO 8
<211> LENGTH: 563
<212> TYPE: PRT
<213> ORGANISM: Pseudomonas acidivorans

<400> SEQUENCE: 8

Met Ser His Pro Ala Ile Ser Leu Gln Ala Leu Arg Gly Ser Gly Ala
1               5                   10                  15

Asp Ile Gln Ser Ile His Ile Pro Tyr Glu Arg His Ala Asp Gln Asp
            20                  25                  30

Ala Gly Ala Asp Thr Pro Ala Arg His Pro Val Val Ile Val Gly Ala
```

```
        35                  40                  45

Gly Pro Val Gly Leu Ser Leu Ala Ile Asp Leu Ala Gln Arg Gly Gln
    50                  55                  60

Arg Val Val Leu Leu Asp Asn Asp Cys Arg Leu Ser Thr Gly Ser Arg
65                  70                  75                  80

Ala Ile Cys Phe Ser Lys Arg Thr Leu Glu Ile Trp Asp Arg Leu Gly
                85                  90                  95

Val Gly Gln Pro Met Val Asp Lys Gly Val Ser Trp Asn Leu Gly Lys
            100                 105                 110

Val Phe Phe Lys Asp Gln Pro Leu Tyr Arg Phe Asp Leu Leu Pro Glu
        115                 120                 125

Asp Gly His Glu Arg Pro Ala Phe Ile Asn Leu Gln Gln Tyr Tyr Ala
    130                 135                 140

Glu Ala Tyr Leu Val Glu Arg Ala Leu Gln Leu Pro Leu Ile Asp Leu
145                 150                 155                 160

Arg Trp His Ser Lys Val Thr Ala Leu Glu Pro Gln Ala Glu Gly Ala
                165                 170                 175

Leu Leu Thr Val Glu Thr Pro Asp Gly Ser Tyr Arg Ile Asp Ala Gln
            180                 185                 190

Trp Val Leu Ala Cys Asp Gly Ser Arg Ser Pro Leu Arg Gly Leu Leu
        195                 200                 205

Gly Gln Glu Ser His Gly Arg Ile Phe Arg Asp Arg Phe Leu Ile Ala
    210                 215                 220

Asp Val Lys Met His Ala Glu Phe Pro Thr Glu Arg Trp Phe Trp Phe
225                 230                 235                 240

Asp Pro Pro Phe His Pro Gly Gln Ser Val Leu Leu His Arg Gln Pro
                245                 250                 255

Asp Asp Val Trp Arg Ile Asp Phe Gln Leu Gly Trp Asp Ala Asp Pro
            260                 265                 270

Glu Glu Glu Lys Lys Pro Glu Asn Ile Val Pro Arg Ile Arg Ala Leu
        275                 280                 285

Leu Gly Lys Asp Ala Pro Phe Glu Leu Glu Trp Ala Ser Val Tyr Thr
    290                 295                 300

Phe Ala Cys Leu Arg Met Asp Arg Phe Val His Gly Arg Val Val Phe
305                 310                 315                 320

Ala Gly Asp Ser Ala His Gly Val Ser Pro Phe Gly Ala Arg Gly Ala
                325                 330                 335

Asn Ser Gly Val Gln Asp Ala Glu Asn Leu Ala Trp Lys Leu Asp Arg
            340                 345                 350

Val Leu Arg Gly Gln Ala Asp Ala Ser Leu Ile Ala Thr Tyr Gly Ala
        355                 360                 365

Glu Arg Glu Tyr Ala Ala Asp Glu Asn Ile Arg Asn Ser Thr Arg Ala
    370                 375                 380

Thr Asp Phe Ile Thr Pro Lys Ser Glu Ile Ser Arg Leu Phe Arg Asp
385                 390                 395                 400

Ala Val Leu Asp Leu Ala Arg Asp His Glu Phe Ala Arg Arg Ile Val
                405                 410                 415

Asn Ser Gly Arg Leu Ser Val Pro Ala Thr Leu His Gly Ser Ala Leu
            420                 425                 430

Asn Thr Pro Asp Thr Asp Thr Phe Asp Gly Thr Gln Leu Pro Gly Ala
        435                 440                 445

Val Leu Ala Asp Ala Pro Met Arg Arg Pro Gly Ala Asp Gly Thr Ala
    450                 455                 460
```

```
Trp Leu Leu Arg Ala Leu Gly Pro Asp Phe Thr Leu Leu His Phe Asp
465                 470                 475                 480

Pro Thr Pro Ala Trp Ala Gln Ala Leu Pro Gly Val Leu Asn Leu Ser
                485                 490                 495

Ile Ala Ala Glu Gly Glu Ala His Ala Pro Asp Ala Asp Leu Ile Asp
            500                 505                 510

Ala Arg Gly Leu Ala Ala Lys Arg Leu Asp Ala Arg Pro Gly Thr Ser
        515                 520                 525

Tyr Leu Leu Arg Pro Asp Gln His Val Cys Ala Arg Trp Arg Arg Pro
    530                 535                 540

Asp Glu Ala Ser Val Arg Ala Ala Leu Gln Arg Ala Cys Gly Ala Ala
545                 550                 555                 560

Ala Thr Ala


<210> SEQ ID NO 9
<211> LENGTH: 966
<212> TYPE: DNA
<213> ORGANISM: Pseudomonas acidivorans
<220> FEATURE:
<221> NAME/KEY: CDS
<222> LOCATION: (1)..(966)

<400> SEQUENCE: 9

atg acc acc aag acc ttt gcc tcc gcc gcc gac ctc gaa atc aag cag       48
Met Thr Thr Lys Thr Phe Ala Ser Ala Ala Asp Leu Glu Ile Lys Gln
1               5                   10                  15

gtc agc ttc gac aag ctc tcc gag cac gcc tat gcc tac acg gcc gaa       96
Val Ser Phe Asp Lys Leu Ser Glu His Ala Tyr Ala Tyr Thr Ala Glu
            20                  25                  30

ggc gac ccc aac acc ggc atc atc att ggc gac gac gcg gtg atg gtg      144
Gly Asp Pro Asn Thr Gly Ile Ile Ile Gly Asp Asp Ala Val Met Val
        35                  40                  45

atc gac acc cag gcc acg ccc gtc atg gcc cag gac gtg atc cgc cgc      192
Ile Asp Thr Gln Ala Thr Pro Val Met Ala Gln Asp Val Ile Arg Arg
    50                  55                  60

atc cgt gag gtc acg gac aag ccc atc aag tac gtg acg ctg tcg cac      240
Ile Arg Glu Val Thr Asp Lys Pro Ile Lys Tyr Val Thr Leu Ser His
65                  70                  75                  80

tac cac gcg gtg cgc gtg ctg ggc gcc tcg gcc ttc ttc gcg gaa ggc      288
Tyr His Ala Val Arg Val Leu Gly Ala Ser Ala Phe Phe Ala Glu Gly
                85                  90                  95

gcc gaa cac atc att gcc agc cag gac acc tac gac ctc atc gtg gag      336
Ala Glu His Ile Ile Ala Ser Gln Asp Thr Tyr Asp Leu Ile Val Glu
            100                 105                 110

cgc ggc gag cag gac aag gcc agc gag atc ggc cgc ttt ccc cgc ctg      384
Arg Gly Glu Gln Asp Lys Ala Ser Glu Ile Gly Arg Phe Pro Arg Leu
        115                 120                 125

ttc cag aac gtg gaa agc gtg ccc gat ggc atg acc tgg ccc acc ctc      432
Phe Gln Asn Val Glu Ser Val Pro Asp Gly Met Thr Trp Pro Thr Leu
    130                 135                 140

acc ttc acc ggc aag atg acg ctg tgg ctg ggc aag ctg gaa gtg cag      480
Thr Phe Thr Gly Lys Met Thr Leu Trp Leu Gly Lys Leu Glu Val Gln
145                 150                 155                 160

atc ctg cag ctg ggc cgc ggc cac acc aag ggc gac acc gtg gtc tgg      528
Ile Leu Gln Leu Gly Arg Gly His Thr Lys Gly Asp Thr Val Val Trp
                165                 170                 175

ctg ccc cag gac aag gtg ctg ttc agc ggc gac ctg gtg gag ttc ggc      576
Leu Pro Gln Asp Lys Val Leu Phe Ser Gly Asp Leu Val Glu Phe Gly
            180                 185                 190

gcc acg ccc tat gcg ggc gat gcc tac ttc cag gac tgg ccg cac acg      624
```

```
Ala Thr Pro Tyr Ala Gly Asp Ala Tyr Phe Gln Asp Trp Pro His Thr
        195                 200                 205

ctg gac gcc atc gcc gcc ctg cag ccc gaa aag ctc gtg ccc ggc cgg      672
Leu Asp Ala Ile Ala Ala Leu Gln Pro Glu Lys Leu Val Pro Gly Arg
    210                 215                 220

ggc gcc gcg ctg cag acg ccg gcc gag gtg cag gcc ggc ctg gcc ggc      720
Gly Ala Ala Leu Gln Thr Pro Ala Glu Val Gln Ala Gly Leu Ala Gly
225                 230                 235                 240

acg cgc gac ttc atc agc gac ctg tgg acc gag gtc aag gcc ggc gcc      768
Thr Arg Asp Phe Ile Ser Asp Leu Trp Thr Glu Val Lys Ala Gly Ala
                245                 250                 255

gat gcc cag cag gac ctg cgc aag gtc tac gag gcc gcc ttc gcc aag      816
Asp Ala Gln Gln Asp Leu Arg Lys Val Tyr Glu Ala Ala Phe Ala Lys
            260                 265                 270

ctg cag ccc aag tac ggc cag tgg gtg atc ttc aac cac tgc atg ccc      864
Leu Gln Pro Lys Tyr Gly Gln Trp Val Ile Phe Asn His Cys Met Pro
        275                 280                 285

ttc gat gtg acc cgc gcc tat gac gag gca tcg ggc cac gcc gac cca      912
Phe Asp Val Thr Arg Ala Tyr Asp Glu Ala Ser Gly His Ala Asp Pro
    290                 295                 300

cgc atc tgg acc gcc gag cgc gac cgc cag atg tgg ctg gcg ctc gaa      960
Arg Ile Trp Thr Ala Glu Arg Asp Arg Gln Met Trp Leu Ala Leu Glu
305                 310                 315                 320

ggc tga                                                              966
Gly


<210> SEQ ID NO 10
<211> LENGTH: 321
<212> TYPE: PRT
<213> ORGANISM: Pseudomonas acidivorans

<400> SEQUENCE: 10

Met Thr Thr Lys Thr Phe Ala Ser Ala Ala Asp Leu Glu Ile Lys Gln
1               5                   10                  15

Val Ser Phe Asp Lys Leu Ser Glu His Ala Tyr Ala Tyr Thr Ala Glu
            20                  25                  30

Gly Asp Pro Asn Thr Gly Ile Ile Ile Gly Asp Asp Ala Val Met Val
        35                  40                  45

Ile Asp Thr Gln Ala Thr Pro Val Met Ala Gln Asp Val Ile Arg Arg
    50                  55                  60

Ile Arg Glu Val Thr Asp Lys Pro Ile Lys Tyr Val Thr Leu Ser His
65                  70                  75                  80

Tyr His Ala Val Arg Val Leu Gly Ala Ser Ala Phe Phe Ala Glu Gly
                85                  90                  95

Ala Glu His Ile Ile Ala Ser Gln Asp Thr Tyr Asp Leu Ile Val Glu
            100                 105                 110

Arg Gly Glu Gln Asp Lys Ala Ser Glu Ile Gly Arg Phe Pro Arg Leu
        115                 120                 125

Phe Gln Asn Val Glu Ser Val Pro Asp Gly Met Thr Trp Pro Thr Leu
    130                 135                 140

Thr Phe Thr Gly Lys Met Thr Leu Trp Leu Gly Lys Leu Glu Val Gln
145                 150                 155                 160

Ile Leu Gln Leu Gly Arg Gly His Thr Lys Gly Asp Thr Val Val Trp
                165                 170                 175

Leu Pro Gln Asp Lys Val Leu Phe Ser Gly Asp Leu Val Glu Phe Gly
            180                 185                 190

Ala Thr Pro Tyr Ala Gly Asp Ala Tyr Phe Gln Asp Trp Pro His Thr
        195                 200                 205
```

```
Leu Asp Ala Ile Ala Ala Leu Gln Pro Glu Lys Leu Val Pro Gly Arg
    210                 215                 220

Gly Ala Ala Leu Gln Thr Pro Ala Glu Val Gln Ala Gly Leu Ala Gly
225                 230                 235                 240

Thr Arg Asp Phe Ile Ser Asp Leu Trp Thr Glu Val Lys Ala Gly Ala
                245                 250                 255

Asp Ala Gln Gln Asp Leu Arg Lys Val Tyr Glu Ala Ala Phe Ala Lys
            260                 265                 270

Leu Gln Pro Lys Tyr Gly Gln Trp Val Ile Phe Asn His Cys Met Pro
        275                 280                 285

Phe Asp Val Thr Arg Ala Tyr Asp Glu Ala Ser Gly His Ala Asp Pro
    290                 295                 300

Arg Ile Trp Thr Ala Glu Arg Asp Arg Gln Met Trp Leu Ala Leu Glu
305                 310                 315                 320

Gly


<210> SEQ ID NO 11
<211> LENGTH: 966
<212> TYPE: DNA
<213> ORGANISM: Artificial
<220> FEATURE:
<221> NAME/KEY: CDS
<222> LOCATION: (1)..(966)
<223> OTHER INFORMATION: P. acidovorans HPAC mutant

<400> SEQUENCE: 11

atg tcc acc aag acc ttt gcc tcc gcc gcc gac ctc gaa atc aag cag       48
Met Ser Thr Lys Thr Phe Ala Ser Ala Ala Asp Leu Glu Ile Lys Gln
1               5                   10                  15

gtc agc ttc gac aag ctc tcc gag cac gcc tat gcc tac acg gcc gaa       96
Val Ser Phe Asp Lys Leu Ser Glu His Ala Tyr Ala Tyr Thr Ala Glu
            20                  25                  30

ggc gac ccc aac acc ggc atc atc att ggc gac gac gcg gtg atg gtg      144
Gly Asp Pro Asn Thr Gly Ile Ile Ile Gly Asp Asp Ala Val Met Val
        35                  40                  45

atc gac acc cag gcc acg ccc gtc atg gcc cag gac gtg atc cgc cgc      192
Ile Asp Thr Gln Ala Thr Pro Val Met Ala Gln Asp Val Ile Arg Arg
    50                  55                  60

atc cgt gag gtc acg gac aag ccc atc aag tac gtg acg ctg tcg cac      240
Ile Arg Glu Val Thr Asp Lys Pro Ile Lys Tyr Val Thr Leu Ser His
65                  70                  75                  80

tac cac gcg gtg cgc gtg ctg ggc gcc tcg gcc ttc ttc gcg gaa ggc      288
Tyr His Ala Val Arg Val Leu Gly Ala Ser Ala Phe Phe Ala Glu Gly
                85                  90                  95

gcc gaa cac atc att gcc agc cag gac acc tac gac ctc atc gtg gag      336
Ala Glu His Ile Ile Ala Ser Gln Asp Thr Tyr Asp Leu Ile Val Glu
            100                 105                 110

cgc ggc gag cag gac aag gcc agc gag atc ggc cgc ttt ccc cgc ctg      384
Arg Gly Glu Gln Asp Lys Ala Ser Glu Ile Gly Arg Phe Pro Arg Leu
        115                 120                 125

ttc cag aac gtg gaa agc gtg ccc gat ggc atg acc tgg ccc acc ctc      432
Phe Gln Asn Val Glu Ser Val Pro Asp Gly Met Thr Trp Pro Thr Leu
    130                 135                 140

acc ttc acc ggc aag atg acg ctg tgg ctg ggc aag ctg gaa gtg cag      480
Thr Phe Thr Gly Lys Met Thr Leu Trp Leu Gly Lys Leu Glu Val Gln
145                 150                 155                 160

atc ctg cag ctg ggc cgc ggc cac acc aag ggc gac acc gtg gtc tgg      528
Ile Leu Gln Leu Gly Arg Gly His Thr Lys Gly Asp Thr Val Val Trp
                165                 170                 175
```

```
ctg ccc cag gac aag gtg ctg ttc agc ggc gac ctg gtg gag ttc ggc      576
Leu Pro Gln Asp Lys Val Leu Phe Ser Gly Asp Leu Val Glu Phe Gly
            180                 185                 190

gcc acg ccc tat gcg ggc gat gcc tac ttc cag gac tgg ccg cac acg      624
Ala Thr Pro Tyr Ala Gly Asp Ala Tyr Phe Gln Asp Trp Pro His Thr
        195                 200                 205

ctg gac acc atc gcc gcc ctg cag ccc gaa aag ctc gtg ccc ggc cgg      672
Leu Asp Thr Ile Ala Ala Leu Gln Pro Glu Lys Leu Val Pro Gly Arg
    210                 215                 220

ggc gcc gcg ctg cag acg ccg gcc gag gtg cag gcc ggc ctg gcc ggc      720
Gly Ala Ala Leu Gln Thr Pro Ala Glu Val Gln Ala Gly Leu Ala Gly
225                 230                 235                 240

acg cgc gac ttc atc agc gac ctg tgg acc gag gtc aag gcc ggc gcc      768
Thr Arg Asp Phe Ile Ser Asp Leu Trp Thr Glu Val Lys Ala Gly Ala
                245                 250                 255

gat gcc cag cag gac ctg cgc aag gtc tac gag gcc gcc ttc gcc aag      816
Asp Ala Gln Gln Asp Leu Arg Lys Val Tyr Glu Ala Ala Phe Ala Lys
            260                 265                 270

ctg cag ccc aag tac ggc cag tgg gtg atc ttc aac cac tgc atg ccc      864
Leu Gln Pro Lys Tyr Gly Gln Trp Val Ile Phe Asn His Cys Met Pro
        275                 280                 285

ttc gat gtg acc cgc gcc tat gac gag gca tcg ggc cac gcc gac cca      912
Phe Asp Val Thr Arg Ala Tyr Asp Glu Ala Ser Gly His Ala Asp Pro
    290                 295                 300

cgc atc tgg acc gcc gag cgc gac cgc cag atg tgg ctg gcg ctc gaa      960
Arg Ile Trp Thr Ala Glu Arg Asp Arg Gln Met Trp Leu Ala Leu Glu
305                 310                 315                 320

ggc tga                                                              966
Gly


<210> SEQ ID NO 12
<211> LENGTH: 321
<212> TYPE: PRT
<213> ORGANISM: Artificial
<220> FEATURE:
<223> OTHER INFORMATION: P. acidovorans HPAC mutant

<400> SEQUENCE: 12

Met Ser Thr Lys Thr Phe Ala Ser Ala Ala Asp Leu Glu Ile Lys Gln
1               5                   10                  15

Val Ser Phe Asp Lys Leu Ser Glu His Ala Tyr Ala Tyr Thr Ala Glu
            20                  25                  30

Gly Asp Pro Asn Thr Gly Ile Ile Ile Gly Asp Asp Ala Val Met Val
        35                  40                  45

Ile Asp Thr Gln Ala Thr Pro Val Met Ala Gln Asp Val Ile Arg Arg
    50                  55                  60

Ile Arg Glu Val Thr Asp Lys Pro Ile Lys Tyr Val Thr Leu Ser His
65                  70                  75                  80

Tyr His Ala Val Arg Val Leu Gly Ala Ser Ala Phe Phe Ala Glu Gly
                85                  90                  95

Ala Glu His Ile Ile Ala Ser Gln Asp Thr Tyr Asp Leu Ile Val Glu
            100                 105                 110

Arg Gly Glu Gln Asp Lys Ala Ser Glu Ile Gly Arg Phe Pro Arg Leu
        115                 120                 125

Phe Gln Asn Val Glu Ser Val Pro Asp Gly Met Thr Trp Pro Thr Leu
    130                 135                 140

Thr Phe Thr Gly Lys Met Thr Leu Trp Leu Gly Lys Leu Glu Val Gln
145                 150                 155                 160

Ile Leu Gln Leu Gly Arg Gly His Thr Lys Gly Asp Thr Val Val Trp
```

```
                165                 170                 175

Leu Pro Gln Asp Lys Val Leu Phe Ser Gly Asp Leu Val Glu Phe Gly
            180                 185                 190

Ala Thr Pro Tyr Ala Gly Asp Ala Tyr Phe Gln Asp Trp Pro His Thr
        195                 200                 205

Leu Asp Thr Ile Ala Ala Leu Gln Pro Glu Lys Leu Val Pro Gly Arg
    210                 215                 220

Gly Ala Ala Leu Gln Thr Pro Ala Glu Val Gln Ala Gly Leu Ala Gly
225                 230                 235                 240

Thr Arg Asp Phe Ile Ser Asp Leu Trp Thr Glu Val Lys Ala Gly Ala
                245                 250                 255

Asp Ala Gln Gln Asp Leu Arg Lys Val Tyr Glu Ala Ala Phe Ala Lys
            260                 265                 270

Leu Gln Pro Lys Tyr Gly Gln Trp Val Ile Phe Asn His Cys Met Pro
        275                 280                 285

Phe Asp Val Thr Arg Ala Tyr Asp Glu Ala Ser Gly His Ala Asp Pro
    290                 295                 300

Arg Ile Trp Thr Ala Glu Arg Asp Arg Gln Met Trp Leu Ala Leu Glu
305                 310                 315                 320

Gly


<210> SEQ ID NO 13
<211> LENGTH: 966
<212> TYPE: DNA
<213> ORGANISM: Artificial
<220> FEATURE:
<221> NAME/KEY: CDS
<222> LOCATION: (1)..(966)
<223> OTHER INFORMATION: P. acidovorans HPAC mutant

<400> SEQUENCE: 13

atg tcc acc aag acc ttt gcc tcc gcc gcc gac ctc gaa atc aag cag       48
Met Ser Thr Lys Thr Phe Ala Ser Ala Ala Asp Leu Glu Ile Lys Gln
1               5                   10                  15

gtc agc ttc gac aag ctc tcc gag cac gcc tat gcc tac acg gcc gaa       96
Val Ser Phe Asp Lys Leu Ser Glu His Ala Tyr Ala Tyr Thr Ala Glu
            20                  25                  30

ggc gac ccc aac acc ggc atc atc att ggc gac gac gcg gtg atg gtg      144
Gly Asp Pro Asn Thr Gly Ile Ile Ile Gly Asp Asp Ala Val Met Val
        35                  40                  45

atc gac acc cag gcc acg ccc gtc atg gcc cag gac gtg atc cgc cgc      192
Ile Asp Thr Gln Ala Thr Pro Val Met Ala Gln Asp Val Ile Arg Arg
    50                  55                  60

atc cgt gag gtc acg gac aag ccc atc aag tac gtg acg ctg tcg cac      240
Ile Arg Glu Val Thr Asp Lys Pro Ile Lys Tyr Val Thr Leu Ser His
65                  70                  75                  80

tac cac gcg gtg cgc gtg ctg ggc gcc tcg gcc ttc ttc gcg gaa ggc      288
Tyr His Ala Val Arg Val Leu Gly Ala Ser Ala Phe Phe Ala Glu Gly
                85                  90                  95

gcc gaa cac atc att gcc agc cag gac acc tac gac ctc atc gtg gag      336
Ala Glu His Ile Ile Ala Ser Gln Asp Thr Tyr Asp Leu Ile Val Glu
            100                 105                 110

cgc ggc gag cag gac aag gcc agc gag atc ggc cgc ttt ccc cgc ctg      384
Arg Gly Glu Gln Asp Lys Ala Ser Glu Ile Gly Arg Phe Pro Arg Leu
        115                 120                 125

ttc cag aac gtg gaa agc gtg ccc gat ggc atg acc tgg ccc acc ctc      432
Phe Gln Asn Val Glu Ser Val Pro Asp Gly Met Thr Trp Pro Thr Leu
    130                 135                 140

acc ttc acc ggc aag atg acg ctg tgg ctg ggc aag ctg gaa gtg cag      480
```

```
Thr Phe Thr Gly Lys Met Thr Leu Trp Leu Gly Lys Leu Glu Val Gln
145                 150                 155                 160

atc ctg cag ctg ggc cgc ggc cac acc aag ggc gac acc gtg gtc tgg      528
Ile Leu Gln Leu Gly Arg Gly His Thr Lys Gly Asp Thr Val Val Trp
                165                 170                 175

ctg ccc cag gac aag gtg ctg ttc agc ggc gac ctg gtg gag ttc ggc      576
Leu Pro Gln Asp Lys Val Leu Phe Ser Gly Asp Leu Val Glu Phe Gly
            180                 185                 190

gcc acg ccc tat gcg ggc gat gcc tac ttc cag gac tgg ccg cac acg      624
Ala Thr Pro Tyr Ala Gly Asp Ala Tyr Phe Gln Asp Trp Pro His Thr
        195                 200                 205

ctg gac gcc atc gcc gcc ctg cag ccc gaa aag ctc gtg ccc ggc cgg      672
Leu Asp Ala Ile Ala Ala Leu Gln Pro Glu Lys Leu Val Pro Gly Arg
    210                 215                 220

ggc gcc gcg ctg cag acg ccg gcc gag gtg cag gcc ggc ctg gcc ggc      720
Gly Ala Ala Leu Gln Thr Pro Ala Glu Val Gln Ala Gly Leu Ala Gly
225                 230                 235                 240

acg cgc gac ttc atc agc gac ctg tgg acc gag gtc aag gcc ggc gcc      768
Thr Arg Asp Phe Ile Ser Asp Leu Trp Thr Glu Val Lys Ala Gly Ala
                245                 250                 255

gat gcc cag cag gac ctg cgc aag gtc tac gag gcc gcc ttc gcc aag      816
Asp Ala Gln Gln Asp Leu Arg Lys Val Tyr Glu Ala Ala Phe Ala Lys
            260                 265                 270

ctg cag ccc aag tac ggc cag tgg gtg atc ttc aac cac tgc atg ccc      864
Leu Gln Pro Lys Tyr Gly Gln Trp Val Ile Phe Asn His Cys Met Pro
        275                 280                 285

ttc gat gtg acc cgc gcc tat gac gag gca tcg ggc cac gcc gac cca      912
Phe Asp Val Thr Arg Ala Tyr Asp Glu Ala Ser Gly His Ala Asp Pro
    290                 295                 300

cgc atc tgg acc gcc gag cgc gac cgc cag atg tgg ctg gcg ctc gaa      960
Arg Ile Trp Thr Ala Glu Arg Asp Arg Gln Met Trp Leu Ala Leu Glu
305                 310                 315                 320

ggc tga                                                              966
Gly


<210> SEQ ID NO 14
<211> LENGTH: 321
<212> TYPE: PRT
<213> ORGANISM: Artificial
<220> FEATURE:
<223> OTHER INFORMATION: P. acidovorans HPAC mutant

<400> SEQUENCE: 14

Met Ser Thr Lys Thr Phe Ala Ser Ala Ala Asp Leu Glu Ile Lys Gln
1               5                   10                  15

Val Ser Phe Asp Lys Leu Ser Glu His Ala Tyr Ala Tyr Thr Ala Glu
            20                  25                  30

Gly Asp Pro Asn Thr Gly Ile Ile Ile Gly Asp Asp Ala Val Met Val
        35                  40                  45

Ile Asp Thr Gln Ala Thr Pro Val Met Ala Gln Asp Val Ile Arg Arg
    50                  55                  60

Ile Arg Glu Val Thr Asp Lys Pro Ile Lys Tyr Val Thr Leu Ser His
65                  70                  75                  80

Tyr His Ala Val Arg Val Leu Gly Ala Ser Ala Phe Phe Ala Glu Gly
                85                  90                  95

Ala Glu His Ile Ile Ala Ser Gln Asp Thr Tyr Asp Leu Ile Val Glu
            100                 105                 110

Arg Gly Glu Gln Asp Lys Ala Ser Glu Ile Gly Arg Phe Pro Arg Leu
        115                 120                 125
```

```
Phe Gln Asn Val Glu Ser Val Pro Asp Gly Met Thr Trp Pro Thr Leu
    130                 135                 140

Thr Phe Thr Gly Lys Met Thr Leu Trp Leu Gly Lys Leu Glu Val Gln
145                 150                 155                 160

Ile Leu Gln Leu Gly Arg Gly His Thr Lys Gly Asp Thr Val Val Trp
                165                 170                 175

Leu Pro Gln Asp Lys Val Leu Phe Ser Gly Asp Leu Val Glu Phe Gly
            180                 185                 190

Ala Thr Pro Tyr Ala Gly Asp Ala Tyr Phe Gln Asp Trp Pro His Thr
        195                 200                 205

Leu Asp Ala Ile Ala Ala Leu Gln Pro Glu Lys Leu Val Pro Gly Arg
    210                 215                 220

Gly Ala Ala Leu Gln Thr Pro Ala Glu Val Gln Ala Gly Leu Ala Gly
225                 230                 235                 240

Thr Arg Asp Phe Ile Ser Asp Leu Trp Thr Glu Val Lys Ala Gly Ala
                245                 250                 255

Asp Ala Gln Gln Asp Leu Arg Lys Val Tyr Glu Ala Ala Phe Ala Lys
            260                 265                 270

Leu Gln Pro Lys Tyr Gly Gln Trp Val Ile Phe Asn His Cys Met Pro
        275                 280                 285

Phe Asp Val Thr Arg Ala Tyr Asp Glu Ala Ser Gly His Ala Asp Pro
    290                 295                 300

Arg Ile Trp Thr Ala Glu Arg Asp Arg Gln Met Trp Leu Ala Leu Glu
305                 310                 315                 320

Gly


<210> SEQ ID NO 15
<211> LENGTH: 3549
<212> TYPE: DNA
<213> ORGANISM: Artificial
<220> FEATURE:
<221> NAME/KEY:
<222> LOCATION:
<223> OTHER INFORMATION: Synthetic expression cassette
<220> FEATURE:
<221> NAME/KEY: promoter
<222> LOCATION: (1)..(928)
<220> FEATURE:
<221> NAME/KEY: CDS
<222> LOCATION: (965)..(2647)
<220> FEATURE:
<221> NAME/KEY: terminator
<222> LOCATION: (2811)..(3549)

<400> SEQUENCE: 15

tgcatgccta ggtcgaggag aaatatgagt cgaggcatgg atacactaag ttcccctgaa      60

gtgagcatga tctttgatgc tgagatgatt cccagagcaa gatagtttgt gctgcaagtg     120

acacaattgt aatgaaacca ccactcaacg aatttacttg tggctttgac atgtcgtgtg     180

ctctgtttgt atttgtgagt gccggttggt aattattttt gttaatgtga ttttaaaacc     240

tcttatgtaa atagttactt tatctattga agtgtgttct tgtggtctat agtttctcaa     300

agggaaatta aaatgttgac atcccattta caattgataa cttggtatac acaaactttg     360

taaatttggt gatatttatg gtcgaaagaa ggcaataccc attgtatgtt ccaatatcaa     420

tatcaatacg ataacttgat aatactaaca tatgattgtc attgtttttc cagtatcaat     480

atacattaag ctactacaaa attagtataa atcactatat tataaatctt tttcggttgt     540

aacttgtaat tcgtgggttt ttaaaataaa agcatgtgaa aattttcaaa taatgtgatg     600

gcgcaatttt attttccgag ttccaaaata ttgccgcttc attaccctaa tttgtggcgc     660
```

```
cacatgtaaa acaaaagacg attcttagtg gctatcactg ccatcacgcg gatcactaat    720

atgaaccgtc gattaaaaca gatcgacggt ttatacatca ttttattgta cacacggatc    780

gatatctcag ccgttagatt taatatgcga tctgattgct caaaaaatag actctccgtc    840

tttgcctata aaaacaattt cacatctttc tcacccaaat ctactcttaa ccgttcttct    900

tcttctacag acatcaattt ctctcgactc tagaggatcc aagcttatcg atttcgaacc    960

cctc atg act tca ctt aca gtg tcc ggc cgg gtg gcg cag gtc ctc agc    1009
     Met Thr Ser Leu Thr Val Ser Gly Arg Val Ala Gln Val Leu Ser
     1               5                   10                  15

agc tat gtc agc gat gtg ttc ggt gtg atg ggc aac gga aac gtc tac    1057
Ser Tyr Val Ser Asp Val Phe Gly Val Met Gly Asn Gly Asn Val Tyr
                20                  25                  30

ttc ctg gac gcc gcc gag aag gag ggc ctc cgc ttc acg gcc gta cgc    1105
Phe Leu Asp Ala Ala Glu Lys Glu Gly Leu Arg Phe Thr Ala Val Arg
            35                  40                  45

cat gaa ggt gcc gcc atc gcg gcg gcg gac gcc tac tat cgg gca tcc    1153
His Glu Gly Ala Ala Ile Ala Ala Ala Asp Ala Tyr Tyr Arg Ala Ser
        50                  55                  60

ggg cgc ctg gcg gcg ggg acc acc acc tac ggc ccc ggt tac acc aac    1201
Gly Arg Leu Ala Ala Gly Thr Thr Thr Tyr Gly Pro Gly Tyr Thr Asn
    65                  70                  75

gcc ctg acg gcc ctc gcc gag gcg gtc cag gcg cag atc ccc gtg gtg    1249
Ala Leu Thr Ala Leu Ala Glu Ala Val Gln Ala Gln Ile Pro Val Val
80                  85                  90                  95

ctc gtc acc ggg gac gcc ccg agc agc ggc gcc cgg cct tgg gac gtg    1297
Leu Val Thr Gly Asp Ala Pro Ser Ser Gly Ala Arg Pro Trp Asp Val
                100                 105                 110

gac cag gcc gcg atc gcc gcc ggg ctg ggg gcg gcg acc ttc acg gtc    1345
Asp Gln Ala Ala Ile Ala Ala Gly Leu Gly Ala Ala Thr Phe Thr Val
            115                 120                 125

acc cgt gaa gcc gca ggc tcc atc acg cag gaa gcg gtg gag tac gca    1393
Thr Arg Glu Ala Ala Gly Ser Ile Thr Gln Glu Ala Val Glu Tyr Ala
        130                 135                 140

ctt gcc cgg cgg acc gcc gtc gtg atc gcc gtt cca tac gac ctg tcg    1441
Leu Ala Arg Arg Thr Ala Val Val Ile Ala Val Pro Tyr Asp Leu Ser
    145                 150                 155

gcc ctt gag gcg gcg gag gaa gat ctt ccc gtg ccg ccg gcg gcc tcg    1489
Ala Leu Glu Ala Ala Glu Glu Asp Leu Pro Val Pro Pro Ala Ala Ser
160                 165                 170                 175

gtt ccg gac gcc atc ggc ggc gga ctc gga cgg gcg gcc gaa gtg cgg    1537
Val Pro Asp Ala Ile Gly Gly Gly Leu Gly Arg Ala Ala Glu Val Arg
                180                 185                 190

gcg gcc gaa ttg ctg gcg ggc gcg aag cgg ccg ctc atc ctt gcc ggc    1585
Ala Ala Glu Leu Leu Ala Gly Ala Lys Arg Pro Leu Ile Leu Ala Gly
            195                 200                 205

cgc ggt gcg cac ctc gca gga acc ggc ccc gaa ctc cgg gaa ctc gcc    1633
Arg Gly Ala His Leu Ala Gly Thr Gly Pro Glu Leu Arg Glu Leu Ala
        210                 215                 220

gac cgc ctc ggc gcg ctc acg gcc ggc acc gca ctg gcg ctg aac ctg    1681
Asp Arg Leu Gly Ala Leu Thr Ala Gly Thr Ala Leu Ala Leu Asn Leu
    225                 230                 235

ctg cag ggc gag ggg tac ctc ggc gtc gcg ggc ggc ttc ggc acg gat    1729
Leu Gln Gly Glu Gly Tyr Leu Gly Val Ala Gly Gly Phe Gly Thr Asp
240                 245                 250                 255

acc gcc gcc ggg ctc atg ggc gag gcg gac gtg gtg ctc gtg gcg gga    1777
Thr Ala Ala Gly Leu Met Gly Glu Ala Asp Val Val Leu Val Ala Gly
                260                 265                 270

gcc agc ctg acc ccc ttc acc atg cgc ttc ggc cac ctg atc ggc ccg    1825
```

```
Ala Ser Leu Thr Pro Phe Thr Met Arg Phe Gly His Leu Ile Gly Pro
            275                 280                 285

gac gcc acc gtg atc cag atc gac acc gcc atg gag ccg acg gac ccg      1873
Asp Ala Thr Val Ile Gln Ile Asp Thr Ala Met Glu Pro Thr Asp Pro
        290                 295                 300

cgg gtg gac ctg ttt gtc agt gcg gac gcg aag gcc gct gcc ggc cgg      1921
Arg Val Asp Leu Phe Val Ser Ala Asp Ala Lys Ala Ala Ala Gly Arg
    305                 310                 315

atc ctc cgg ctg ctg gat gac gcc gcc ggg gcc aat gcg tcg aag gcc      1969
Ile Leu Arg Leu Leu Asp Asp Ala Ala Gly Ala Asn Ala Ser Lys Ala
320                 325                 330                 335

tgg cgc gcg gaa gca ctc aag cgt ctg gcc gaa gga ccc tgc cac cac      2017
Trp Arg Ala Glu Ala Leu Lys Arg Leu Ala Glu Gly Pro Cys His His
                340                 345                 350

ccc ggc acc gca gag acc acg gac ggc cgc ctt gac ccc cgg gcg ctt      2065
Pro Gly Thr Ala Glu Thr Thr Asp Gly Arg Leu Asp Pro Arg Ala Leu
            355                 360                 365

gct tcg gca ctg gat gcc gtc ctg ccg gaa cgc cgc acc gtg gtc cag      2113
Ala Ser Ala Leu Asp Ala Val Leu Pro Glu Arg Arg Thr Val Val Gln
        370                 375                 380

gac ggc ggg cac ttc ctg ggc tgg gca ccc atg tac tgg cgc atc ccc      2161
Asp Gly Gly His Phe Leu Gly Trp Ala Pro Met Tyr Trp Arg Ile Pro
    385                 390                 395

cgt cct cag gac ctg gtc atg gtg ggg acc gcg tac cag tcg atc ggg      2209
Arg Pro Gln Asp Leu Val Met Val Gly Thr Ala Tyr Gln Ser Ile Gly
400                 405                 410                 415

ctt ggc ctg gcc agc gcc gtg ggg gcg tcc cgg gcc gtg gac gac ggc      2257
Leu Gly Leu Ala Ser Ala Val Gly Ala Ser Arg Ala Val Asp Asp Gly
                420                 425                 430

aat atc ctg gtg ctg gcg gcg ggc gac ggc gga ttc ctg atg ggc ctg      2305
Asn Ile Leu Val Leu Ala Ala Gly Asp Gly Gly Phe Leu Met Gly Leu
            435                 440                 445

tcc gac ctg gaa tcg ctc gtg ggc gcg gcg agc agc gcc gtc gtg gtg      2353
Ser Asp Leu Glu Ser Leu Val Gly Ala Ala Ser Ser Ala Val Val Val
        450                 455                 460

atc tac aac gac gcc gcc tac ggg gcc gag atc cat cag tac ggc tca      2401
Ile Tyr Asn Asp Ala Ala Tyr Gly Ala Glu Ile His Gln Tyr Gly Ser
    465                 470                 475

cgg ggg ctc acc gaa aag ccc atg ctg atc ccc gaa gtg gac ttc agc      2449
Arg Gly Leu Thr Glu Lys Pro Met Leu Ile Pro Glu Val Asp Phe Ser
480                 485                 490                 495

ggg att gcc cgc gcg atc ggg gcg gaa tcc gca atc atc cgc aag ctg      2497
Gly Ile Ala Arg Ala Ile Gly Ala Glu Ser Ala Ile Ile Arg Lys Leu
                500                 505                 510

tcg gac ctc tcc gcg ctc acg gac tgg atc gag gcc ggc gcc agg gga      2545
Ser Asp Leu Ser Ala Leu Thr Asp Trp Ile Glu Ala Gly Ala Arg Gly
            515                 520                 525

acc ttc gtg gcc gac tgc cgc atc acc tca agc gtc cgg gcc ccg tgg      2593
Thr Phe Val Ala Asp Cys Arg Ile Thr Ser Ser Val Arg Ala Pro Trp
        530                 535                 540

ctg agc gaa tgg atg agg gcc tcg caa gcg gcg aag gag gcg gtg gcg      2641
Leu Ser Glu Trp Met Arg Ala Ser Gln Ala Ala Lys Glu Ala Val Ala
    545                 550                 555

ggc tag ggccggcctc gtcgaaatgc cgccctccaa cccaactcag taccagctca      2697
Gly
560

gggcgttctc agggctggga acgccctgag ctgctactca tttgttcgaa ctcgaggtcg    2757

acggtatcga taagcttgat atcgaattcc tgcagcccgg gggatccact aggggatccc    2817

ccgatccgcg tttgtgtttt ctgggtttct cacttaagcg tctgcgtttt acttttgtat    2877
```

```
tgggtttggc gtttagtagt ttgcggtagc gttcttgtta tgtgtaatta cgctttttct   2937

tcttgcttca gcagtttcgg ttgaaatata aatcgaatca agtttcactt tatcagcgtt   2997

gttttaaatt ttggcattaa attggtgaaa attgcttcaa ttttgtatct aaatagaaga   3057

gacaacatga aattcgactt ttgacctcaa atcttcgaac atttatttcc tgatttcacg   3117

atggatgagg ataacgaaag ggcggttcct atgtccggga aagttcccgt agaagacaat   3177

gagcaaagct actgaaacgc ggacacgacg tcgcattggt acggatatga gttaaaccga   3237

ctcaattcct ttattaagac ataaaccgat tttggttaaa gtgtaacagt gagctgatat   3297

aaaaccgaaa caaaccggta caagtttgat tgagcaactt gatgacaaac ttcagaattt   3357

tggttattga atgaaaatca tagtctaatc gtaaaaaatg tacagaagaa aagctagagc   3417

agaacaaaga ttctatattc tggttccaat ttatcatcgc tttaacgtcc ctcagatttg   3477

atcgggctgc aggaattcgg cctgactgat catttaaaca ctagttctag agcggccgcc   3537

accgcggtgg ag                                                       3549
```

```
<210> SEQ ID NO 16
<211> LENGTH: 560
<212> TYPE: PRT
<213> ORGANISM: Artificial
<220> FEATURE:
<223> OTHER INFORMATION: Expression cassette

<400> SEQUENCE: 16

Met Thr Ser Leu Thr Val Ser Gly Arg Val Ala Gln Val Leu Ser Ser
1               5                   10                  15

Tyr Val Ser Asp Val Phe Gly Val Met Gly Asn Gly Asn Val Tyr Phe
            20                  25                  30

Leu Asp Ala Ala Glu Lys Glu Gly Leu Arg Phe Thr Ala Val Arg His
        35                  40                  45

Glu Gly Ala Ala Ile Ala Ala Ala Asp Ala Tyr Tyr Arg Ala Ser Gly
    50                  55                  60

Arg Leu Ala Ala Gly Thr Thr Thr Tyr Gly Pro Gly Tyr Thr Asn Ala
65                  70                  75                  80

Leu Thr Ala Leu Ala Glu Ala Val Gln Ala Gln Ile Pro Val Val Leu
                85                  90                  95

Val Thr Gly Asp Ala Pro Ser Ser Gly Ala Arg Pro Trp Asp Val Asp
            100                 105                 110

Gln Ala Ala Ile Ala Ala Gly Leu Gly Ala Ala Thr Phe Thr Val Thr
        115                 120                 125

Arg Glu Ala Ala Gly Ser Ile Thr Gln Glu Ala Val Glu Tyr Ala Leu
    130                 135                 140

Ala Arg Arg Thr Ala Val Val Ile Ala Val Pro Tyr Asp Leu Ser Ala
145                 150                 155                 160

Leu Glu Ala Ala Glu Glu Asp Leu Pro Val Pro Pro Ala Ala Ser Val
                165                 170                 175

Pro Asp Ala Ile Gly Gly Gly Leu Gly Arg Ala Ala Glu Val Arg Ala
            180                 185                 190

Ala Glu Leu Leu Ala Gly Ala Lys Arg Pro Leu Ile Leu Ala Gly Arg
        195                 200                 205

Gly Ala His Leu Ala Gly Thr Gly Pro Glu Leu Arg Glu Leu Ala Asp
    210                 215                 220

Arg Leu Gly Ala Leu Thr Ala Gly Thr Ala Leu Ala Leu Asn Leu Leu
225                 230                 235                 240
```

```
Gln Gly Glu Gly Tyr Leu Gly Val Ala Gly Gly Phe Gly Thr Asp Thr
                245                 250                 255

Ala Ala Gly Leu Met Gly Glu Ala Asp Val Val Leu Val Ala Gly Ala
            260                 265                 270

Ser Leu Thr Pro Phe Thr Met Arg Phe Gly His Leu Ile Gly Pro Asp
        275                 280                 285

Ala Thr Val Ile Gln Ile Asp Thr Ala Met Glu Pro Thr Asp Pro Arg
    290                 295                 300

Val Asp Leu Phe Val Ser Ala Asp Ala Lys Ala Ala Ala Gly Arg Ile
305                 310                 315                 320

Leu Arg Leu Leu Asp Asp Ala Ala Gly Ala Asn Ala Ser Lys Ala Trp
                325                 330                 335

Arg Ala Glu Ala Leu Lys Arg Leu Ala Glu Gly Pro Cys His His Pro
            340                 345                 350

Gly Thr Ala Glu Thr Thr Asp Gly Arg Leu Asp Pro Arg Ala Leu Ala
        355                 360                 365

Ser Ala Leu Asp Ala Val Leu Pro Glu Arg Arg Thr Val Val Gln Asp
    370                 375                 380

Gly Gly His Phe Leu Gly Trp Ala Pro Met Tyr Trp Arg Ile Pro Arg
385                 390                 395                 400

Pro Gln Asp Leu Val Met Val Gly Thr Ala Tyr Gln Ser Ile Gly Leu
                405                 410                 415

Gly Leu Ala Ser Ala Val Gly Ala Ser Arg Ala Val Asp Asp Gly Asn
            420                 425                 430

Ile Leu Val Leu Ala Ala Gly Asp Gly Gly Phe Leu Met Gly Leu Ser
        435                 440                 445

Asp Leu Glu Ser Leu Val Gly Ala Ala Ser Ser Ala Val Val Val Ile
    450                 455                 460

Tyr Asn Asp Ala Ala Tyr Gly Ala Glu Ile His Gln Tyr Gly Ser Arg
465                 470                 475                 480

Gly Leu Thr Glu Lys Pro Met Leu Ile Pro Glu Val Asp Phe Ser Gly
                485                 490                 495

Ile Ala Arg Ala Ile Gly Ala Glu Ser Ala Ile Ile Arg Lys Leu Ser
            500                 505                 510

Asp Leu Ser Ala Leu Thr Asp Trp Ile Glu Ala Gly Ala Arg Gly Thr
        515                 520                 525

Phe Val Ala Asp Cys Arg Ile Thr Ser Ser Val Arg Ala Pro Trp Leu
    530                 535                 540

Ser Glu Trp Met Arg Ala Ser Gln Ala Ala Lys Glu Ala Val Ala Gly
545                 550                 555                 560
```

```
<210> SEQ ID NO 17
<211> LENGTH: 2838
<212> TYPE: DNA
<213> ORGANISM: Artificial
<220> FEATURE:
<221> NAME/KEY:
<222> LOCATION:
<223> OTHER INFORMATION: Synthetic expression cassette
<220> FEATURE:
<221> NAME/KEY: promoter
<222> LOCATION: (1)..(807)
<220> FEATURE:
<221> NAME/KEY: CDS
<222> LOCATION: (847)..(2538)
<220> FEATURE:
<221> NAME/KEY: terminator
<222> LOCATION: (2539)..(2838)
<223> OTHER INFORMATION: Expression cassette
```

```
<400> SEQUENCE: 17

ggcccccccct cgagcccaca gatggttaga gaggcttacg cagcaggtct catcaagacg      60

atctacccga gcaataatct ccaggaaatc aaataccttc ccaagaaggt taaagatgca     120

gtcaaaagat tcaggactaa ctgcatcaag aacacagaga aagatatatt tctcaagatc     180

agaagtacta ttccagtatg gacgattcaa ggcttgcttc acaaaccaag gcaagtaata     240

gagattggag tctctaaaaa ggtagttccc actgaatcaa aggccatgga gtcaaagatt     300

caaatagagg acctaacaga actcgccgta aagactggcg aacagttcat acagagtctc     360

ttacgactca atgacaagaa gaaaatcttc gtcaacatgg tggagcacga cacacttgtc     420

tactccaaaa atatcaaaga tacagtctca gaagaccaaa gggcaattga gacttttcaa     480

caaagggtaa tatccggaaa cctcctcgga ttccattgcc cagctatctg tcactttatt     540

gtgaagatag tggaaaagga aggtggctcc tacaaatgcc atcattgcga taaaggaaag     600

gccatcgttg aagatgcctc tgccgacagt ggtcccaaag atggaccccc acccacgagg     660

agcatcgtgg aaaaagaaga cgttccaacc acgtcttcaa agcaagtgga ttgatgtgat     720

atctccactg acgtaaggga tgacgcacaa tcccactatc cttcgcaaga cccttcctct     780

atataaggaa gttcatttca tttggagaga acacgggggga ctctagagga tcagaggacg     840

aacaac atg tcc cac ccc gcc atc tcc ctg caa gcg ctg cgc ggc agc        888
       Met Ser His Pro Ala Ile Ser Leu Gln Ala Leu Arg Gly Ser
       1               5                   10

ggc gca gac ata cag tcc atc cac atc ccc tac gag cgc cat gcc gac       936
Gly Ala Asp Ile Gln Ser Ile His Ile Pro Tyr Glu Arg His Ala Asp
15                  20                  25                  30

cag gac gcc ggt gcg gac acg ccc gcc cgg cat ccc gtc gtc atc gtc       984
Gln Asp Ala Gly Ala Asp Thr Pro Ala Arg His Pro Val Val Ile Val
                35                  40                  45

ggc gcc ggc ccc gtg ggc ctg tcg ctg gcc atc gac ctg gcc cag cgc      1032
Gly Ala Gly Pro Val Gly Leu Ser Leu Ala Ile Asp Leu Ala Gln Arg
            50                  55                  60

ggc cag cgc gtg gtg ctg ctg gac aac gac tgc cgg ctg tcc acg ggc      1080
Gly Gln Arg Val Val Leu Leu Asp Asn Asp Cys Arg Leu Ser Thr Gly
        65                  70                  75

tcg cgc gcc atc tgc ttt tcc aag cgc acg ctg gag atc tgg gac cgc      1128
Ser Arg Ala Ile Cys Phe Ser Lys Arg Thr Leu Glu Ile Trp Asp Arg
    80                  85                  90

ctg ggc gtg ggc cag ccc atg gtg gac aag ggc gtg tcc tgg aac ctg      1176
Leu Gly Val Gly Gln Pro Met Val Asp Lys Gly Val Ser Trp Asn Leu
95                  100                 105                 110

ggc aag gtc ttc ttc aag gac cag ccg ctg tac cgc ttc gac ctg ctg      1224
Gly Lys Val Phe Phe Lys Asp Gln Pro Leu Tyr Arg Phe Asp Leu Leu
                115                 120                 125

ccc gag gac ggc cac gag cgc ccg gcc ttc atc aac ctg cag cag tac      1272
Pro Glu Asp Gly His Glu Arg Pro Ala Phe Ile Asn Leu Gln Gln Tyr
            130                 135                 140

tac gcc gag gcc tat ctg gtc gag cgc gca ctg cag ctg ccg ctg atc      1320
Tyr Ala Glu Ala Tyr Leu Val Glu Arg Ala Leu Gln Leu Pro Leu Ile
        145                 150                 155

gac ctg cgc tgg cac agc aag gtc acg gca ctg gag ccg cag gcc gag      1368
Asp Leu Arg Trp His Ser Lys Val Thr Ala Leu Glu Pro Gln Ala Glu
    160                 165                 170

ggc gcg ctg ctg acc gtg gag acg cct gac ggc agc tac cgc atc gat      1416
Gly Ala Leu Leu Thr Val Glu Thr Pro Asp Gly Ser Tyr Arg Ile Asp
175                 180                 185                 190

gcg caa tgg gtc ctg gcc tgc gat ggc tcg cgc tcg ccg ctg cgc ggc      1464
Ala Gln Trp Val Leu Ala Cys Asp Gly Ser Arg Ser Pro Leu Arg Gly
```

```
                195                 200                 205

ctg ctg ggc cag gaa agc cat ggc cgc atc ttc cgc gac cgc ttc ctg      1512
Leu Leu Gly Gln Glu Ser His Gly Arg Ile Phe Arg Asp Arg Phe Leu
            210                 215                 220

atc gcc gac gtg aag atg cac gcc gaa ttc ccc acc gag cgc tgg ttc      1560
Ile Ala Asp Val Lys Met His Ala Glu Phe Pro Thr Glu Arg Trp Phe
        225                 230                 235

tgg ttc gac ccg ccc ttc cac ccg ggc cag agc gtg ctg ctg cac cgc      1608
Trp Phe Asp Pro Pro Phe His Pro Gly Gln Ser Val Leu Leu His Arg
    240                 245                 250

cag ccc gac gat gtc tgg cgc atc gac ttc cag ctg ggc tgg gac gcg      1656
Gln Pro Asp Asp Val Trp Arg Ile Asp Phe Gln Leu Gly Trp Asp Ala
255                 260                 265                 270

gac ccc gag gaa gag aaa aag ccc gag aac atc gtg ccg cgc atc cgc      1704
Asp Pro Glu Glu Glu Lys Lys Pro Glu Asn Ile Val Pro Arg Ile Arg
                275                 280                 285

gcc ctg ctg ggc aag gac gcg ccc ttc gag ctg gaa tgg gcc agc gtc      1752
Ala Leu Leu Gly Lys Asp Ala Pro Phe Glu Leu Glu Trp Ala Ser Val
            290                 295                 300

tac acc ttc gcc tgc ctg cgc atg gac cgc ttc gtc cat ggc cgc gtg      1800
Tyr Thr Phe Ala Cys Leu Arg Met Asp Arg Phe Val His Gly Arg Val
        305                 310                 315

gtc ttt gcg ggc gac agc gcc cac ggc gtc tcg ccg ttt ggc gca cgc      1848
Val Phe Ala Gly Asp Ser Ala His Gly Val Ser Pro Phe Gly Ala Arg
    320                 325                 330

ggc gcc aac agc ggc gtg cag gat gcc gag aac ctg gca tgg aag ctg      1896
Gly Ala Asn Ser Gly Val Gln Asp Ala Glu Asn Leu Ala Trp Lys Leu
335                 340                 345                 350

gac cgc gtg ctg cgc ggc cag gcc gat gcc tcg ctg atc gcc acc tac      1944
Asp Arg Val Leu Arg Gly Gln Ala Asp Ala Ser Leu Ile Ala Thr Tyr
                355                 360                 365

ggc gcc gag cgc gaa tac gcg gcc gac gag aac atc cgc aac tcc acg      1992
Gly Ala Glu Arg Glu Tyr Ala Ala Asp Glu Asn Ile Arg Asn Ser Thr
            370                 375                 380

cgc gcc acc gac ttc atc acg ccc aag agc gag atc agc cgc ctg ttt      2040
Arg Ala Thr Asp Phe Ile Thr Pro Lys Ser Glu Ile Ser Arg Leu Phe
        385                 390                 395

cgc gac gcc gtg ctg gac ctg gcg cgc gac cat gaa ttc gcg cgc cgc      2088
Arg Asp Ala Val Leu Asp Leu Ala Arg Asp His Glu Phe Ala Arg Arg
    400                 405                 410

atc gtc aac agc ggg cgg ctg tcc gtg ccg gcc acg ctg cac ggc tcc      2136
Ile Val Asn Ser Gly Arg Leu Ser Val Pro Ala Thr Leu His Gly Ser
415                 420                 425                 430

gcg ctc aac acg cct gac acc gac acc ttc gac gga acg cag ctg ccc      2184
Ala Leu Asn Thr Pro Asp Thr Asp Thr Phe Asp Gly Thr Gln Leu Pro
                435                 440                 445

ggc gcc gtg ctg gcc gat gcg ccc atg cgc cgg ccc ggc gca gac ggc      2232
Gly Ala Val Leu Ala Asp Ala Pro Met Arg Arg Pro Gly Ala Asp Gly
            450                 455                 460

acg gcc tgg ctg ctg cgc gca ctg gga ccg gac ttc acg ctg ctg cac      2280
Thr Ala Trp Leu Leu Arg Ala Leu Gly Pro Asp Phe Thr Leu Leu His
        465                 470                 475

ttc gac ccc acg ccc gcc tgg gcg cag gcg ctg ccc ggc gtg ctc aac      2328
Phe Asp Pro Thr Pro Ala Trp Ala Gln Ala Leu Pro Gly Val Leu Asn
    480                 485                 490

ctg tcc atc gcg gcc gag ggc gag gcc cat gcg cca gac gcc gac ctc      2376
Leu Ser Ile Ala Ala Glu Gly Glu Ala His Ala Pro Asp Ala Asp Leu
495                 500                 505                 510

atc gat gcg cgc ggc ctg gcg gcc aaa cgc ctg gat gca cgc ccc ggc      2424
Ile Asp Ala Arg Gly Leu Ala Ala Lys Arg Leu Asp Ala Arg Pro Gly
```

```
                515                 520                 525

acc agc tac ctg ctg cgg cct gac cag cat gtc tgc gcg cgc tgg cgc      2472
Thr Ser Tyr Leu Leu Arg Pro Asp Gln His Val Cys Ala Arg Trp Arg
            530                 535                 540

cgc ccc gac gaa gcc agc gtg cgc gcc gcg ctg caa aga gcc tgc ggc      2520
Arg Pro Asp Glu Ala Ser Val Arg Ala Ala Leu Gln Arg Ala Cys Gly
        545                 550                 555

gcc gcc gcc acg gcc tga acctcttaag cttatcgata ccgtcgacga             2568
Ala Ala Ala Thr Ala
    560

atttccccga tcgttcaaac atttggcaat aaagtttctt aagattgaat cctgttgccg   2628

gtcttgcgat gattatcata taatttctgt tgaattacgt taagcatgta ataattaaca   2688

tgtaatgcat gacgttattt atgagatggg tttttatgat tagagtcccg caattataca   2748

tttaatacgc gatagaaaac aaaatatagc gcgcaaacta ggataaatta tcgcgcgcgg   2808

tgtcatctat gttcctaggt cgggaattgc                                     2838


<210> SEQ ID NO 18
<211> LENGTH: 563
<212> TYPE: PRT
<213> ORGANISM: Artificial
<220> FEATURE:
<223> OTHER INFORMATION: Expression Cassette

<400> SEQUENCE: 18

Met Ser His Pro Ala Ile Ser Leu Gln Ala Leu Arg Gly Ser Gly Ala
1               5                   10                  15

Asp Ile Gln Ser Ile His Ile Pro Tyr Glu Arg His Ala Asp Gln Asp
            20                  25                  30

Ala Gly Ala Asp Thr Pro Ala Arg His Pro Val Val Ile Val Gly Ala
        35                  40                  45

Gly Pro Val Gly Leu Ser Leu Ala Ile Asp Leu Ala Gln Arg Gly Gln
    50                  55                  60

Arg Val Val Leu Leu Asp Asn Asp Cys Arg Leu Ser Thr Gly Ser Arg
65                  70                  75                  80

Ala Ile Cys Phe Ser Lys Arg Thr Leu Glu Ile Trp Asp Arg Leu Gly
                85                  90                  95

Val Gly Gln Pro Met Val Asp Lys Gly Val Ser Trp Asn Leu Gly Lys
            100                 105                 110

Val Phe Phe Lys Asp Gln Pro Leu Tyr Arg Phe Asp Leu Leu Pro Glu
        115                 120                 125

Asp Gly His Glu Arg Pro Ala Phe Ile Asn Leu Gln Gln Tyr Tyr Ala
    130                 135                 140

Glu Ala Tyr Leu Val Glu Arg Ala Leu Gln Leu Pro Leu Ile Asp Leu
145                 150                 155                 160

Arg Trp His Ser Lys Val Thr Ala Leu Glu Pro Gln Ala Glu Gly Ala
                165                 170                 175

Leu Leu Thr Val Glu Thr Pro Asp Gly Ser Tyr Arg Ile Asp Ala Gln
            180                 185                 190

Trp Val Leu Ala Cys Asp Gly Ser Arg Ser Pro Leu Arg Gly Leu Leu
        195                 200                 205

Gly Gln Glu Ser His Gly Arg Ile Phe Arg Asp Arg Phe Leu Ile Ala
    210                 215                 220

Asp Val Lys Met His Ala Glu Phe Pro Thr Glu Arg Trp Phe Trp Phe
225                 230                 235                 240

Asp Pro Pro Phe His Pro Gly Gln Ser Val Leu Leu His Arg Gln Pro
```

```
                245                 250                 255

Asp Asp Val Trp Arg Ile Asp Phe Gln Leu Gly Trp Asp Ala Asp Pro
            260                 265                 270

Glu Glu Glu Lys Lys Pro Glu Asn Ile Val Pro Arg Ile Arg Ala Leu
        275                 280                 285

Leu Gly Lys Asp Ala Pro Phe Glu Leu Glu Trp Ala Ser Val Tyr Thr
    290                 295                 300

Phe Ala Cys Leu Arg Met Asp Arg Phe Val His Gly Arg Val Val Phe
305                 310                 315                 320

Ala Gly Asp Ser Ala His Gly Val Ser Pro Phe Gly Ala Arg Gly Ala
                325                 330                 335

Asn Ser Gly Val Gln Asp Ala Glu Asn Leu Ala Trp Lys Leu Asp Arg
            340                 345                 350

Val Leu Arg Gly Gln Ala Asp Ala Ser Leu Ile Ala Thr Tyr Gly Ala
        355                 360                 365

Glu Arg Glu Tyr Ala Ala Asp Glu Asn Ile Arg Asn Ser Thr Arg Ala
    370                 375                 380

Thr Asp Phe Ile Thr Pro Lys Ser Glu Ile Ser Arg Leu Phe Arg Asp
385                 390                 395                 400

Ala Val Leu Asp Leu Ala Arg Asp His Glu Phe Ala Arg Arg Ile Val
                405                 410                 415

Asn Ser Gly Arg Leu Ser Val Pro Ala Thr Leu His Gly Ser Ala Leu
            420                 425                 430

Asn Thr Pro Asp Thr Asp Thr Phe Asp Gly Thr Gln Leu Pro Gly Ala
        435                 440                 445

Val Leu Ala Asp Ala Pro Met Arg Arg Pro Gly Ala Asp Gly Thr Ala
    450                 455                 460

Trp Leu Leu Arg Ala Leu Gly Pro Asp Phe Thr Leu Leu His Phe Asp
465                 470                 475                 480

Pro Thr Pro Ala Trp Ala Gln Ala Leu Pro Gly Val Leu Asn Leu Ser
                485                 490                 495

Ile Ala Ala Glu Gly Glu Ala His Ala Pro Asp Ala Asp Leu Ile Asp
            500                 505                 510

Ala Arg Gly Leu Ala Ala Lys Arg Leu Asp Ala Arg Pro Gly Thr Ser
        515                 520                 525

Tyr Leu Leu Arg Pro Asp Gln His Val Cys Ala Arg Trp Arg Arg Pro
    530                 535                 540

Asp Glu Ala Ser Val Arg Ala Ala Leu Gln Arg Ala Cys Gly Ala Ala
545                 550                 555                 560

Ala Thr Ala
```

<210> SEQ ID NO 19
<211> LENGTH: 1839
<212> TYPE: DNA
<213> ORGANISM: Artificial
<220> FEATURE:
<221> NAME/KEY:
<222> LOCATION:
<223> OTHER INFORMATION: Synthetic expression cassette
<220> FEATURE:
<221> NAME/KEY: promoter
<222> LOCATION: (1)..(547)
<220> FEATURE:
<221> NAME/KEY: CDS
<222> LOCATION: (574)..(1539)
<220> FEATURE:
<221> NAME/KEY: terminator
<222> LOCATION: (1540)..(1839)

<400> SEQUENCE: 19

```
cccccctcgag gtcgacggta ttgatcagct tccagaaggt aattatccaa gatgtagcat      60

caagaatcca atgtttacgg gaaaaactat ggaagtatta tgtgagctca gcaagaagca     120

gatcaatatg cggcacatat gcaacctatg ttcaaaaatg aagaatgtac agatacaaga     180

tcctatactg ccagaatacg aagaagaata cgtagaaatt gaaaaagaag aaccaggcga     240

agaaaagaat cttgaagacg taagcactga cgacaacaat gaaaagaaga agataaggtc     300

ggtgattgtg aaagagacat agaggacaca tgtaaggtgg aaaatgtaag ggcggaaagt     360

aaccttatca caaaggaatc ttatccccca ctacttatcc ttttatattt ttccgtgtca     420

tttttgccct tgagttttcc tatataagga accaagttcg gcatttgtga aaacaagaaa     480

aaatttggtg taagctattt tctttgaagt actgaggata caacttcaga gaaatttgta     540

agtttgtaga tctgaattcg atgcaggatg cac atg tcc acc aag acc ttt gcc     594
                                      Met Ser Thr Lys Thr Phe Ala
                                      1               5

tcc gcc gcc gac ctc gaa atc aag cag gtc agc ttc gac aag ctc tcc     642
Ser Ala Ala Asp Leu Glu Ile Lys Gln Val Ser Phe Asp Lys Leu Ser
        10                  15                  20

gag cac gcc tat gcc tac acg gcc gaa ggc gac ccc aac acc ggc atc     690
Glu His Ala Tyr Ala Tyr Thr Ala Glu Gly Asp Pro Asn Thr Gly Ile
    25                  30                  35

atc att ggc gac gac gcg gtg atg gtg atc gac acc cag gcc acg ccc     738
Ile Ile Gly Asp Asp Ala Val Met Val Ile Asp Thr Gln Ala Thr Pro
40                  45                  50                  55

gtc atg gcc cag gac gtg atc cgc cgc atc cgt gag gtc acg gac aag     786
Val Met Ala Gln Asp Val Ile Arg Arg Ile Arg Glu Val Thr Asp Lys
                60                  65                  70

ccc atc aag tac gtg acg ctg tcg cac tac cac gcg gtg cgc gtg ctg     834
Pro Ile Lys Tyr Val Thr Leu Ser His Tyr His Ala Val Arg Val Leu
            75                  80                  85

ggc gcc tcg gcc ttc ttc gcg gaa ggc gcc gaa cac atc att gcc agc     882
Gly Ala Ser Ala Phe Phe Ala Glu Gly Ala Glu His Ile Ile Ala Ser
        90                  95                  100

cag gac acc tac gac ctc atc gtg gag cgc ggc gag cag gac aag gcc     930
Gln Asp Thr Tyr Asp Leu Ile Val Glu Arg Gly Glu Gln Asp Lys Ala
    105                 110                 115

agc gag atc ggc cgc ttt ccc cgc ctg ttc cag aac gtg gaa agc gtg     978
Ser Glu Ile Gly Arg Phe Pro Arg Leu Phe Gln Asn Val Glu Ser Val
120                 125                 130                 135

ccc gat ggc atg acc tgg ccc acc ctc acc ttc acc ggc aag atg acg    1026
Pro Asp Gly Met Thr Trp Pro Thr Leu Thr Phe Thr Gly Lys Met Thr
                140                 145                 150

ctg tgg ctg ggc aag ctg gaa gtg cag atc ctg cag ctg ggc cgc ggc    1074
Leu Trp Leu Gly Lys Leu Glu Val Gln Ile Leu Gln Leu Gly Arg Gly
            155                 160                 165

cac acc aag ggc gac acc gtg gtc tgg ctg ccc cag gac aag gtg ctg    1122
His Thr Lys Gly Asp Thr Val Val Trp Leu Pro Gln Asp Lys Val Leu
        170                 175                 180

ttc agc ggc gac ctg gtg gag ttc ggc gcc acg ccc tat gcg ggc gat    1170
Phe Ser Gly Asp Leu Val Glu Phe Gly Ala Thr Pro Tyr Ala Gly Asp
    185                 190                 195

gcc tac ttc cag gac tgg ccg cac acg ctg gac gcc atc gcc gcc ctg    1218
Ala Tyr Phe Gln Asp Trp Pro His Thr Leu Asp Ala Ile Ala Ala Leu
200                 205                 210                 215

cag ccc gaa aag ctc gtg ccc ggc cgg ggc gcc gcg ctg cag acg ccg    1266
Gln Pro Glu Lys Leu Val Pro Gly Arg Gly Ala Ala Leu Gln Thr Pro
                220                 225                 230
```

```
gcc gag gtg cag gcc ggc ctg gcc ggc acg cgc gac ttc atc agc gac     1314
Ala Glu Val Gln Ala Gly Leu Ala Gly Thr Arg Asp Phe Ile Ser Asp
            235                 240                 245

ctg tgg acc gag gtc aag gcc ggc gcc gat gcc cag cag gac ctg cgc     1362
Leu Trp Thr Glu Val Lys Ala Gly Ala Asp Ala Gln Gln Asp Leu Arg
        250                 255                 260

aag gtc tac gag gcc gcc ttc gcc aag ctg cag ccc aag tac ggc cag     1410
Lys Val Tyr Glu Ala Ala Phe Ala Lys Leu Gln Pro Lys Tyr Gly Gln
    265                 270                 275

tgg gtg atc ttc aac cac tgc atg ccc ttc gat gtg acc cgc gcc tat     1458
Trp Val Ile Phe Asn His Cys Met Pro Phe Asp Val Thr Arg Ala Tyr
280                 285                 290                 295

gac gag gca tcg ggc cac gcc gac cca cgc atc tgg acc gcc gag cgc     1506
Asp Glu Ala Ser Gly His Ala Asp Pro Arg Ile Trp Thr Ala Glu Arg
                300                 305                 310

gac cgc cag atg tgg ctg gcg ctc gaa ggc tga tgcaagctta tcgataccgt   1559
Asp Arg Gln Met Trp Leu Ala Leu Glu Gly
            315                 320

cgacgaattt ccccgatcgt tcaaacattt ggcaataaag tttcttaaga ttgaatcctg   1619

ttgccggtct tgcgatgatt atcatataat ttctgttgaa ttacgttaag catgtaataa   1679

ttaacatgta atgcatgacg ttatttatga gatgggtttt tatgattaga gtcccgcaat   1739

tatacattta atacgcgata gaaaacaaaa tatagcgcgc aaactaggat aaattatcgc   1799

gcgcggtgtc atctatgtta ctagatcggg aattgcggcc                         1839


<210> SEQ ID NO 20
<211> LENGTH: 321
<212> TYPE: PRT
<213> ORGANISM: Artificial
<220> FEATURE:
<223> OTHER INFORMATION: Expression cassette

<400> SEQUENCE: 20

Met Ser Thr Lys Thr Phe Ala Ser Ala Ala Asp Leu Glu Ile Lys Gln
1               5                   10                  15

Val Ser Phe Asp Lys Leu Ser Glu His Ala Tyr Ala Tyr Thr Ala Glu
            20                  25                  30

Gly Asp Pro Asn Thr Gly Ile Ile Ile Gly Asp Asp Ala Val Met Val
        35                  40                  45

Ile Asp Thr Gln Ala Thr Pro Val Met Ala Gln Asp Val Ile Arg Arg
    50                  55                  60

Ile Arg Glu Val Thr Asp Lys Pro Ile Lys Tyr Val Thr Leu Ser His
65                  70                  75                  80

Tyr His Ala Val Arg Val Leu Gly Ala Ser Ala Phe Phe Ala Glu Gly
                85                  90                  95

Ala Glu His Ile Ile Ala Ser Gln Asp Thr Tyr Asp Leu Ile Val Glu
            100                 105                 110

Arg Gly Glu Gln Asp Lys Ala Ser Glu Ile Gly Arg Phe Pro Arg Leu
        115                 120                 125

Phe Gln Asn Val Glu Ser Val Pro Asp Gly Met Thr Trp Pro Thr Leu
    130                 135                 140

Thr Phe Thr Gly Lys Met Thr Leu Trp Leu Gly Lys Leu Glu Val Gln
145                 150                 155                 160

Ile Leu Gln Leu Gly Arg Gly His Thr Lys Gly Asp Thr Val Val Trp
                165                 170                 175

Leu Pro Gln Asp Lys Val Leu Phe Ser Gly Asp Leu Val Glu Phe Gly
            180                 185                 190
```

```
Ala Thr Pro Tyr Ala Gly Asp Ala Tyr Phe Gln Asp Trp Pro His Thr
        195                 200                 205

Leu Asp Ala Ile Ala Ala Leu Gln Pro Glu Lys Leu Val Pro Gly Arg
    210                 215                 220

Gly Ala Ala Leu Gln Thr Pro Ala Glu Val Gln Ala Gly Leu Ala Gly
225                 230                 235                 240

Thr Arg Asp Phe Ile Ser Asp Leu Trp Thr Glu Val Lys Ala Gly Ala
                245                 250                 255

Asp Ala Gln Gln Asp Leu Arg Lys Val Tyr Glu Ala Ala Phe Ala Lys
            260                 265                 270

Leu Gln Pro Lys Tyr Gly Gln Trp Val Ile Phe Asn His Cys Met Pro
        275                 280                 285

Phe Asp Val Thr Arg Ala Tyr Asp Glu Ala Ser Gly His Ala Asp Pro
    290                 295                 300

Arg Ile Trp Thr Ala Glu Arg Asp Arg Gln Met Trp Leu Ala Leu Glu
305                 310                 315                 320

Gly
```

<210> SEQ ID NO 21
<211> LENGTH: 4677
<212> TYPE: DNA
<213> ORGANISM: Artificial
<220> FEATURE:
<223> OTHER INFORMATION: Expression cassette

<400> SEQUENCE: 21

```
cccccctcgag gtcgacggta ttgatcagct tccagaaggt aattatccaa gatgtagcat     60

caagaatcca atgtttacgg gaaaaactat ggaagtatta tgtgagctca gcaagaagca    120

gatcaatatg cggcacatat gcaacctatg ttcaaaaatg aagaatgtac agatacaaga    180

tcctatactg ccagaatacg aagaagaata cgtagaaatt gaaaaagaag aaccaggcga    240

agaaaagaat cttgaagacg taagcactga cgacaacaat gaaaagaaga agataaggtc    300

ggtgattgtg aaagagacat agaggacaca tgtaaggtgg aaaatgtaag ggcggaaagt    360

aaccttatca caaaggaatc ttatccccca ctacttatcc ttttatattt ttccgtgtca    420

tttttgccct tgagttttcc tatataagga accaagttcg gcatttgtga aaacaagaaa    480

aaatttggtg taagctattt tctttgaagt actgaggata caacttcaga gaaatttgta    540

agtttgtaga tctgaattcg atgcaggatg cacatgtcca ccaagacctt tgcctccgcc    600

gccgacctcg aaatcaagca ggtcagcttc gacaagctct ccgagcacgc ctatgcctac    660

acggccgaag gcgaccccaa caccggcatc atcattggcg acgacgcggt gatggtgatc    720

gacacccagg ccacgcccgt catggcccag gacgtgatcc gccgcatccg tgaggtcacg    780

gacaagccca tcaagtacgt gacgctgtcg cactaccacg cggtgcgcgt gctgggcgcc    840

tcggccttct tcgcggaagg cgccgaacac atcattgcca gccaggacac ctacgacctc    900

atcgtggagc gcggcgagca ggacaaggcc agcgagatcg gccgctttcc ccgcctgttc    960

cagaacgtgg aaagcgtgcc cgatggcatg acctggccca ccctcacctt caccggcaag   1020

atgacgctgt ggctgggcaa gctggaagtg cagatcctgc agctgggccg cggccacacc   1080

aagggcgaca ccgtggtctg gctgccccag gacaaggtgc tgttcagcgg cgacctggtg   1140

gagttcggcg ccacgcccta tgcgggcgat gcctacttcc aggactggcc gcacacgctg   1200

gacgccatcg ccgccctgca gcccgaaaag ctcgtgcccg gccggggcgc cgcgctgcag   1260

acgccggccg aggtgcaggc cggcctggcc ggcacgcgcg acttcatcag cgacctgtgg   1320
```

-continued

```
accgaggtca aggccggcgc cgatgcccag caggacctgc gcaaggtcta cgaggccgcc   1380
ttcgccaagc tgcagcccaa gtacggccag tgggtgatct tcaaccactg catgcccttc   1440
gatgtgaccc gcgcctatga cgaggcatcg ggccacgccg acccacgcat ctggaccgcc   1500
gagcgcgacc gccagatgtg gctggcgctc gaaggctgat gcaagcttat cgataccgtc   1560
gacgaatttc cccgatcgtt caaacatttg gcaataaagt ttcttaagat tgaatcctgt   1620
tgccggtctt gcgatgatta tcatataatt tctgttgaat tacgttaagc atgtaataat   1680
taacatgtaa tgcatgacgt tatttatgag atgggttttt atgattagag tcccgcaatt   1740
atacatttaa tacgcgatag aaaacaaaat atagcgcgca aactaggata aattatcgcg   1800
cgcggtgtca tctatgttac tagatcggga attgcggccc cccctcgagc ccacagatgg   1860
ttagagaggc ttacgcagca ggtctcatca agacgatcta cccgagcaat aatctccagg   1920
aaatcaaata ccttcccaag aaggttaaag atgcagtcaa aagattcagg actaactgca   1980
tcaagaacac agagaaagat atatttctca agatcagaag tactattcca gtatggacga   2040
ttcaaggctt gcttcacaaa ccaaggcaag taatagagat tggagtctct aaaaaggtag   2100
ttcccactga atcaaaggcc atggagtcaa agattcaaat agaggaccta acagaactcg   2160
ccgtaaagac tggcgaacag ttcatacaga gtctcttacg actcaatgac aagaagaaaa   2220
tcttcgtcaa catggtggag cacgacacac ttgtctactc caaaaatatc aaagatacag   2280
tctcagaaga ccaaagggca attgagactt ttcaacaaag ggtaatatcc ggaaacctcc   2340
tcggattcca ttgcccagct atctgtcact ttattgtgaa gatagtggaa aaggaaggtg   2400
gctcctacaa atgccatcat tgcgataaag gaaaggccat cgttgaagat gcctctgccg   2460
acagtggtcc caaagatgga cccccaccca cgaggagcat cgtggaaaaa gaagacgttc   2520
caaccacgtc ttcaaagcaa gtggattgat gtgatatctc cactgacgta agggatgacg   2580
cacaatccca ctatccttcg caagaccctt cctctatata aggaagttca tttcatttgg   2640
agagaacacg ggggactcta gaggatcaga ggacgaacaa catgtcccac cccgccatct   2700
ccctgcaagc gctgcgcggc agcggcgcag acatacagtc catccacatc ccctacgagc   2760
gccatgccga ccaggacgcc ggtgcggaca cgcccgcccg gcatcccgtc gtcatcgtcg   2820
gcgccggccc cgtgggcctg tcgctggcca tcgacctggc ccagcgcggc cagcgcgtgg   2880
tgctgctgga caacgactgc cggctgtcca cgggctcgcg cgccatctgc ttttccaagc   2940
gcacgctgga gatctgggac cgcctgggcg tgggccagcc catggtggac aagggcgtgt   3000
cctggaacct gggcaaggtc ttcttcaagg accagccgct gtaccgcttc gacctgctgc   3060
ccgaggacgg ccacgagcgc ccggccttca tcaacctgca gcagtactac gccgaggcct   3120
atctggtcga gcgcgcactg cagctgccgc tgatcgacct gcgctggcac agcaaggtca   3180
cggcactgga gccgcaggcc gagggcgcgc tgctgaccgt ggagacgcct gacggcagct   3240
accgcatcga tgcgcaatgg gtcctggcct gcgatggctc gcgctcgccg ctgcgcggcc   3300
tgctgggcca ggaaagccat ggccgcatct tccgcgaccg cttcctgatc gccgacgtga   3360
agatgcacgc cgaattcccc accgagcgct ggttctggtt cgacccgccc ttccacccgg   3420
gccagagcgt gctgctgcac cgccagcccg acgatgtctg gcgcatcgac ttccagctgg   3480
gctgggacgc ggaccccgag gaagagaaaa agcccgagaa catcgtgccg cgcatccgcg   3540
ccctgctggg caaggacgcg cccttcgagc tggaatgggc cagcgtctac accttcgcct   3600
gcctgcgcat ggaccgcttc gtccatggcc gcgtggtctt tgcgggcgac agcgcccacg   3660
gcgtctcgcc gtttggcgca cgcggcgcca acagcggcgt gcaggatgcc gagaacctgg   3720
```

catggaagct ggaccgcgtg ctgcgcggcc aggccgatgc ctcgctgatc gccacctacg 3780
gcgccgagcg cgaatacgcg gccgacgaga acatccgcaa ctccacgcgc gccaccgact 3840
tcatcacgcc caagagcgag atcagccgcc tgtttcgcga cgccgtgctg gacctggcgc 3900
gcgaccatga attcgcgcgc cgcatcgtca acagcgggcg gctgtccgtg ccggccacgc 3960
tgcacggctc cgcgctcaac acgcctgaca ccgacacctt cgacggaacg cagctgcccg 4020
gcgccgtgct ggccgatgcg cccatgcgcc ggcccggcgc agacggcacg gcctggctgc 4080
tgcgcgcact gggaccggac ttcacgctgc tgcacttcga ccccacgccc gcctgggcgc 4140
aggcgctgcc cggcgtgctc aacctgtcca tcgcggccga gggcgaggcc catgcgccag 4200
acgccgacct catcgatgcg cgcggcctgg cggccaaacg cctggatgca cgcccccggca 4260 ccagctacct gctgcggcct gaccagcatg tctgcgcgcg ctggcgccgc cccgacgaag 4320
ccagcgtgcg cgccgcgctg caaagagcct gcggcgccgc cgccacggcc tgaacctctt 4380
aagcttatcg ataccgtcga cgaatttccc cgatcgttca aacatttggc aataaagttt 4440
cttaagattg aatcctgttg ccggtcttgc gatgattatc atataatttc tgttgaatta 4500
cgttaagcat gtaataatta acatgtaatg catgacgtta tttatgagat gggtttttat 4560
gattagagtc ccgcaattat acatttaata cgcgatagaa aacaaaatat agcgcgcaaa 4620
ctaggataaa ttatcgcgcg cggtgtcatc tatgttccta ggtcgggaat tgcggcc 4677

<210> SEQ ID NO 22
<211> LENGTH: 8187
<212> TYPE: DNA
<213> ORGANISM: Artificial
<220> FEATURE:
<223> OTHER INFORMATION: Expression cassette

<400> SEQUENCE: 22 cccctcgag gtcgacggta ttgatcagct tccagaaggt aattatccaa gatgtagcat 60
caagaatcca atgtttacgg gaaaaactat ggaagtatta tgtgagctca gcaagaagca 120
gatcaatatg cggcacatat gcaacctatg ttcaaaaatg aagaatgtac agatacaaga 180
tcctatactg ccagaatacg aagaagaata cgtagaaatt gaaaaagaag aaccaggcga 240
agaaaagaat cttgaagacg taagcactga cgacaacaat gaaaagaaga agataaggtc 300
ggtgattgtg aaagagacat agaggacaca tgtaaggtgg aaaatgtaag ggcggaaagt 360
aaccttatca caaaggaatc ttatccccca ctacttatcc ttttatattt ttccgtgtca 420
tttttgccct tgagttttcc tatataagga accaagttcg gcatttgtga aaacaagaaa 480
aaatttggtg taagctattt tctttgaagt actgaggata caacttcaga gaaatttgta 540
agtttgtaga tctgaattcg atgcaggatg cacatgtcca ccaagacctt tgcctccgcc 600
gccgacctcg aaatcaagca ggtcagcttc gacaagctct ccgagcacgc ctatgcctac 660
acggccgaag gcgaccccaa caccggcatc atcattggcg acgacgcggt gatggtgatc 720
gacacccagg ccacgcccgt catggcccag gacgtgatcc gccgcatccg tgaggtcacg 780
gacaagccca tcaagtacgt gacgctgtcg cactaccacg cggtgcgcgt gctgggcgcc 840
tcggccttct tcgcggaagg cgccgaacac atcattgcca gccaggacac ctacgacctc 900
atcgtggagc gcggcgagca ggacaaggcc agcgagatcg gccgctttcc ccgcctgttc 960
cagaacgtgg aaagcgtgcc cgatggcatg acctggccca ccctcacctt caccggcaag 1020
atgacgctgt ggctgggcaa gctggaagtg cagatcctgc agctgggccg cggccacacc 1080
aagggcgaca ccgtggtctg gctgccccag gacaaggtgc tgttcagcgg cgacctggtg 1140

-continued

```
gagttcggcg ccacgcccta tgcgggcgat gcctacttcc aggactggcc gcacacgctg   1200
gacgccatcg ccgccctgca gcccgaaaag ctcgtgcccg gccggggcgc cgcgctgcag   1260
acgccggccg aggtgcaggc cggcctggcc ggcacgcgcg acttcatcag cgacctgtgg   1320
accgaggtca aggccggcgc cgatgcccag caggacctgc gcaaggtcta cgaggccgcc   1380
ttcgccaagc tgcagcccaa gtacggccag tgggtgatct tcaaccactg catgcccttc   1440
gatgtgaccc gcgcctatga cgaggcatcg ggccacgccg acccacgcat ctggaccgcc   1500
gagcgcgacc gccagatgtg gctggcgctc gaaggctgat gcaagcttat cgataccgtc   1560
gacgaatttc cccgatcgtt caaacatttg gcaataaagt ttcttaagat tgaatcctgt   1620
tgccggtctt gcgatgatta tcatataatt tctgttgaat tacgttaagc atgtaataat   1680
taacatgtaa tgcatgacgt tatttatgag atgggttttt atgattagag tcccgcaatt   1740
atacatttaa tacgcgatag aaaacaaaat atagcgcgca aactaggata aattatcgcg   1800
cgcggtgtca tctatgttac tagatcggga attgcggccc cccctcgagc ccacagatgg   1860
ttagagaggc ttacgcagca ggtctcatca agacgatcta cccgagcaat aatctccagg   1920
aaatcaaata ccttcccaag aaggttaaag atgcagtcaa aagattcagg actaactgca   1980
tcaagaacac agagaaagat atatttctca agatcagaag tactattcca gtatggacga   2040
ttcaaggctt gcttcacaaa ccaaggcaag taatagagat tggagtctct aaaaaggtag   2100
ttcccactga atcaaaggcc atggagtcaa agattcaaat agaggaccta acagaactcg   2160
ccgtaaagac tggcgaacag ttcatacaga gtctcttacg actcaatgac aagaagaaaa   2220
tcttcgtcaa catggtggag cacgacacac ttgtctactc caaaaatatc aaagatacag   2280
tctcagaaga ccaaagggca attgagactt ttcaacaaag ggtaatatcc ggaaacctcc   2340
tcggattcca ttgcccagct atctgtcact ttattgtgaa gatagtggaa aaggaaggtg   2400
gctcctacaa atgccatcat tgcgataaag gaaaggccat cgttgaagat gcctctgccg   2460
acagtggtcc caaagatgga cccccaccca cgaggagcat cgtggaaaaa gaagacgttc   2520
caaccacgtc ttcaaagcaa gtggattgat gtgatatctc cactgacgta agggatgacg   2580
cacaatccca ctatccttcg caagaccctt cctctatata aggaagttca tttcatttgg   2640
agagaacacg ggggactcta gaggatcaga ggacgaacaa catgtcccac cccgccatct   2700
ccctgcaagc gctgcgcggc agcggcgcag acatacagtc catccacatc ccctacgagc   2760
gccatgccga ccaggacgcc ggtgcggaca cgcccgcccg gcatcccgtc gtcatcgtcg   2820
gcgccggccc cgtgggcctg tcgctggcca tcgacctggc ccagcgcggc cagcgcgtgg   2880
tgctgctgga caacgactgc cggctgtcca cgggctcgcg cgccatctgc ttttccaagc   2940
gcacgctgga gatctgggac cgcctgggcg tgggccagcc catggtggac aagggcgtgt   3000
cctggaacct gggcaaggtc ttcttcaagg accagccgct gtaccgcttc gacctgctgc   3060
ccgaggacgg ccacgagcgc ccggccttca tcaacctgca gcagtactac gccgaggcct   3120
atctggtcga gcgcgcactg cagctgccgc tgatcgacct gcgctggcac agcaaggtca   3180
cggcactgga gccgcaggcc gagggcgcgc tgctgaccgt ggagacgcct gacggcagct   3240
accgcatcga tgcgcaatgg gtcctggcct gcgatggctc gcgctcgccg ctgcgcggcc   3300
tgctgggcca ggaaagccat ggccgcatct tccgcgaccg cttcctgatc gccgacgtga   3360
agatgcacgc cgaattcccc accgagcgct ggttctggtt cgacccgccc ttccacccgg   3420
gccagagcgt gctgctgcac cgccagcccg acgatgtctg gcgcatcgac ttccagctgg   3480
gctgggacgc ggaccccgag gaagagaaaa agcccgagaa catcgtgccg cgcatccgcg   3540
```

```
ccctgctggg caaggacgcg cccttcgagc tggaatgggc cagcgtctac accttcgcct   3600
gcctgcgcat ggaccgcttc gtccatggcc gcgtggtctt tgcgggcgac agcgcccacg   3660
gcgtctcgcc gtttggcgca cgcggcgcca acagcggcgt gcaggatgcc gagaacctgg   3720
catggaagct ggaccgcgtg ctgcgcggcc aggccgatgc ctcgctgatc gccacctacg   3780
gcgccgagcg cgaatacgcg gccgacgaga acatccgcaa ctccacgcgc gccaccgact   3840
tcatcacgcc caagagcgag atcagccgcc tgtttcgcga cgccgtgctg gacctggcgc   3900
gcgaccatga attcgcgcgc cgcatcgtca acagcgggcg gctgtccgtg ccggccacgc   3960
tgcacggctc cgcgctcaac acgcctgaca ccgacacctt cgacggaacg cagctgcccg   4020
gcgccgtgct ggccgatgcg cccatgcgcc ggcccggcgc agacggcacg gcctggctgc   4080
tgcgcgcact gggaccggac ttcacgctgc tgcacttcga ccccacgccc gcctgggcgc   4140
aggcgctgcc cggcgtgctc aacctgtcca tcgcggccga gggcgaggcc catgcgccag   4200
acgccgacct catcgatgcg cgcggcctgg cggccaaacg cctggatgca cgccccggca   4260
ccagctacct gctgcggcct gaccagcatg tctgcgcgcg ctggcgccgc cccgacgaag   4320
ccagcgtgcg cgccgcgctg caaagagcct gcggcgccgc cgccacggcc tgaacctctt   4380
aagcttatcg ataccgtcga cgaatttccc cgatcgttca aacatttggc aataaagttt   4440
cttaagattg aatcctgttg ccggtcttgc gatgattatc atataatttc tgttgaatta   4500
cgttaagcat gtaataatta acatgtaatg catgacgtta tttatgagat gggtttttat   4560
gattagagtc ccgcaattat acatttaata cgcgatagaa aacaaaatat agcgcgcaaa   4620
ctaggataaa ttatcgcgcg cggtgtcatc tatgttccta ggtcgaggag aaatatgagt   4680
cgaggcatgg atacactaag ttcccctgaa gtgagcatga tctttgatgc tgagatgatt   4740
cccagagcaa gatagtttgt gctgcaagtg acacaattgt aatgaaacca ccactcaacg   4800
aatttacttg tggctttgac atgtcgtgtg ctctgtttgt atttgtgagt gccggttggt   4860
aattattttt gttaatgtga ttttaaaacc tcttatgtaa atagttactt tatctattga   4920
agtgtgttct tgtggtctat agtttctcaa agggaaatta aaatgttgac atcccattta   4980
caattgataa cttggtatac acaaactttg taaatttggt gatatttatg gtcgaaagaa   5040
ggcaataccc attgtatgtt ccaatatcaa tatcaatacg ataacttgat aatactaaca   5100
tatgattgtc attgtttttc cagtatcaat atacattaag ctactacaaa attagtataa   5160
atcactatat tataaatctt tttcggttgt aacttgtaat tcgtgggttt ttaaaataaa   5220
agcatgtgaa aattttcaaa taatgtgatg gcgcaatttt attttccgag ttccaaaata   5280
ttgccgcttc attaccctaa tttgtggcgc cacatgtaaa acaaaagacg attcttagtg   5340
gctatcactg ccatcacgcg gatcactaat atgaaccgtc gattaaaaca gatcgacggt   5400
ttatacatca ttttattgta cacacggatc gatatctcag ccgttagatt taatatgcga   5460
tctgattgct caaaaaatag actctccgtc tttgcctata aaaacaattt cacatctttc   5520
tcacccaaat ctactcttaa ccgttcttct tcttctacag acatcaattt ctctcgactc   5580
tagaggatcc aagcttatcg atttcgaacc cctcatgact tcacttacag tgtccggccg   5640
ggtggcgcag gtcctcagca gctatgtcag cgatgtgttc ggtgtgatgg gcaacggaaa   5700
cgtctacttc ctggacgccg ccgagaagga gggcctccgc ttcacggccg tacgccatga   5760
aggtgccgcc atcgcggcgg cggacgccta ctatcgggca tccgggcgcc tggcggcggg   5820
gaccaccacc tacggccccg gttacaccaa cgccctgacg gccctcgccg aggcggtcca   5880
ggcgcagatc cccgtggtgc tcgtcaccgg ggacgccccg agcagcggcg cccggccttg   5940
```

```
ggacgtggac caggccgcga tcgccgccgg gctgggggcg gcgaccttca cggtcacccg   6000

tgaagccgca ggctccatca cgcaggaagc ggtggagtac gcacttgccc ggcggaccgc   6060

cgtcgtgatc gccgttccat acgacctgtc ggcccttgag gcggcggagg aagatcttcc   6120

cgtgccgccg gcggcctcgg ttccggacgc catcggcggc ggactcggac gggcggccga   6180

agtgcgggcg gccgaattgc tggcgggcgc gaagcggccg ctcatccttg ccggccgcgg   6240

tgcgcacctc gcaggaaccg gccccgaact ccgggaactc gccgaccgcc tcggcgcgct   6300

cacggccggc accgcactgg cgctgaacct gctgcagggc gaggggtacc tcggcgtcgc   6360

gggcggcttc ggcacggata ccgccgccgg gctcatgggc gaggcggacg tggtgctcgt   6420

ggcgggagcc agcctgaccc ccttcaccat gcgcttcggc cacctgatcg gcccggacgc   6480

caccgtgatc cagatcgaca ccgccatgga gccgacggac ccgcgggtgg acctgtttgt   6540

cagtgcggac gcgaaggccg ctgccggccg gatcctccgg ctgctggatg acgccgccgg   6600

ggccaatgcg tcgaaggcct ggcgcgcgga agcactcaag cgtctggccg aaggaccctg   6660

ccaccacccc ggcaccgcag agaccacgga cggccgcctt gacccccggg cgcttgcttc   6720

ggcactggat gccgtcctgc cggaacgccg caccgtggtc caggacggcg ggcacttcct   6780

gggctgggca cccatgtact ggcgcatccc ccgtcctcag gacctggtca tggtggggac   6840

cgcgtaccag tcgatcgggc ttggcctggc cagcgccgtg gggcgtccc gggccgtgga   6900

cgacggcaat atcctggtgc tggcggcggg cgacggcgga ttcctgatgg gcctgtccga   6960

cctggaatcg ctcgtgggcg cggcgagcag cgccgtcgtg gtgatctaca acgacgccgc   7020

ctacggggcc gagatccatc agtacggctc acgggggctc accgaaaagc ccatgctgat   7080

ccccgaagtg gacttcagcg ggattgcccg cgcgatcggg gcggaatccg caatcatccg   7140

caagctgtcg gacctctccg cgctcacgga ctggatcgag gccggcgcca ggggaacctt   7200

cgtggccgac tgccgcatca cctcaagcgt ccgggccccg tggctgagcg aatggatgag   7260

ggcctcgcaa gcggcgaagg aggcggtggc gggctagggc cggcctcgtc gaaatgccgc   7320

cctccaaccc aactcagtac cagctcaggg cgttctcagg gctgggaacg ccctgagctg   7380

ctactcattt gttcgaactc gaggtcgacg gtatcgataa gcttgatatc gaattcctgc   7440

agcccggggg atccactagg ggatcccccg atccgcgttt gtgttttctg ggtttctcac   7500

ttaagcgtct gcgttttact tttgtattgg gtttggcgtt tagtagtttg cggtagcgtt   7560

cttgttatgt gtaattacgc tttttcttct tgcttcagca gtttcggttg aaatataaat   7620

cgaatcaagt ttcactttat cagcgttgtt ttaaattttg gcattaaatt ggtgaaaatt   7680

gcttcaattt tgtatctaaa tagaagagac aacatgaaat tcgacttttg acctcaaatc   7740

ttcgaacatt tatttcctga tttcacgatg gatgaggata acgaaagggc ggttcctatg   7800

tccgggaaag ttcccgtaga agacaatgag caaagctact gaaacgcgga cacgacgtcg   7860

cattggtacg gatatgagtt aaaccgactc aattccttta ttaagacata aaccgatttt   7920

ggttaaagtg taacagtgag ctgatataaa accgaaacaa accggtacaa gtttgattga   7980

gcaacttgat gacaaacttc agaattttgg ttattgaatg aaaatcatag tctaatcgta   8040

aaaaatgtac agaagaaaag ctagagcaga acaaagattc tatattctgg ttccaattta   8100

tcatcgcttt aacgtccctc agatttgatc gggctgcagg aattcggcct gactgatcat   8160

ttaaacacta ggtcgggaat tgcggcc                                       8187
```

<210> SEQ ID NO 23
<211> LENGTH: 23
<212> TYPE: DNA

```
<213> ORGANISM: Artificial
<220> FEATURE:
<223> OTHER INFORMATION: Synthetic primer OZ-MnD-S711

<400> SEQUENCE: 23

acgtcaccga agaggatgaa aac                                              23


<210> SEQ ID NO 24
<211> LENGTH: 20
<212> TYPE: DNA
<213> ORGANISM: Artificial
<220> FEATURE:
<223> OTHER INFORMATION: Synthetic primer OZ-MnD-AS1578

<400> SEQUENCE: 24

acggccattt cggacttttc                                                  20


<210> SEQ ID NO 25
<211> LENGTH: 7
<212> TYPE: PRT
<213> ORGANISM: Artificial
<220> FEATURE:
<223> OTHER INFORMATION: Synthetic peptide

<400> SEQUENCE: 25

Trp Trp Ala Glu Ala Leu Lys
1               5


<210> SEQ ID NO 26
<211> LENGTH: 20
<212> TYPE: PRT
<213> ORGANISM: Artificial
<220> FEATURE:
<223> OTHER INFORMATION: Synthtic peptide

<400> SEQUENCE: 26

Ala Ala Ala Gly Arg Ile Leu Arg Leu Leu Asp Asp Ala Ala Gly Ala
1               5                   10                  15

Asn Ala Ser Lys
            20


<210> SEQ ID NO 27
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 27

Xaa Asp Asn Arg Phe Thr Ala Val Asp Phe Xaa Thr
1               5                   10


<210> SEQ ID NO 28
<211> LENGTH: 30
<212> TYPE: PRT
<213> ORGANISM: Artificial
<220> FEATURE:
<223> OTHER INFORMATION: Synthetic peptide

<400> SEQUENCE: 28
```

```
Thr Ser Leu Thr Val Ser Gly Arg Val Ala Gln Val Leu Ser Ser Tyr
1               5                   10                  15

Val Ser Asp Val Phe Gly Val Met Gly Asn Gly Asn Val Tyr
            20                  25                  30


<210> SEQ ID NO 29
<211> LENGTH: 20
<212> TYPE: DNA
<213> ORGANISM: Artificial
<220> FEATURE:
<223> OTHER INFORMATION: Synthetic primer Ox3
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 29

ttngcnccng cngcrtcrtc                                                  20


<210> SEQ ID NO 30
<211> LENGTH: 26
<212> TYPE: DNA
<213> ORGANISM: Artificial
<220> FEATURE:
<223> OTHER INFORMATION: Synthetic primer OZ10N
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 30

gaygtnttyg gngtnatggg naaygg                                           26


<210> SEQ ID NO 31
<211> LENGTH: 22
<212> TYPE: DNA
<213> ORGANISM: Artificial
<220> FEATURE:
<223> OTHER INFORMATION: Synthetic primer

<400> SEQUENCE: 31

catgacttca cttacagtgt cc                                               22


<210> SEQ ID NO 32
<211> LENGTH: 21
<212> TYPE: DNA
<213> ORGANISM: Artificial
<220> FEATURE:
```

<223> OTHER INFORMATION: Synthetic primer HPP-C-term

<400> SEQUENCE: 32
caaactgagt agcagctcag g 21

<210> SEQ ID NO 33
<211> LENGTH: 25
<212> TYPE: DNA
<213> ORGANISM: Artificial
<220> FEATURE:
<223> OTHER INFORMATION: Synthetic primer

<400> SEQUENCE: 33
gcaggatgca catgtccacc aagac 25

<210> SEQ ID NO 34
<211> LENGTH: 25
<212> TYPE: DNA
<213> ORGANISM: Artificial
<220> FEATURE:
<223> OTHER INFORMATION: Synthetic primer

<400> SEQUENCE: 34
cggacgccga catgtatcag ccttc 25

<210> SEQ ID NO 35
<211> LENGTH: 26
<212> TYPE: PRT
<213> ORGANISM: Artificial
<220> FEATURE:
<223> OTHER INFORMATION: Synthetic N-terminal peptide

<400> SEQUENCE: 35

Ser His Pro Ala Ile Ser Leu Gln Ala Leu Arg Gly Ser Gly Ala Asp
1 5 10 15

Ile Gln Ser Ile His Ile Pro Tyr Glu Arg
20 25

<210> SEQ ID NO 36
<211> LENGTH: 8
<212> TYPE: PRT
<213> ORGANISM: Artificial
<220> FEATURE:
<223> OTHER INFORMATION: Synthetic peptide

<400> SEQUENCE: 36

Ala Thr Asp Phe Ile Thr Pro Lys
1 5

<210> SEQ ID NO 37
<211> LENGTH: 10
<212> TYPE: PRT
<213> ORGANISM: Artificial
<220> FEATURE:
<223> OTHER INFORMATION: Synthetic peptide

<400> SEQUENCE: 37

Leu Gly Val Gly Gln Pro Met Val Asp Lys
1 5 10

<210> SEQ ID NO 38
<211> LENGTH: 15
<212> TYPE: PRT
<213> ORGANISM: Artificial
<220> FEATURE:
<223> OTHER INFORMATION: Synthetic peptide
<220> FEATURE:

<221> NAME/KEY: misc_feature
<222> LOCATION: (15)..(15)
<223> OTHER INFORMATION: Xaa can be any naturally occurring amino acid

<400> SEQUENCE: 38

Val Val Phe Ala Gly Asp Ser Ala His Gly Val Ser Pro Phe Xaa
1               5                   10                  15

<210> SEQ ID NO 39
<211> LENGTH: 12
<212> TYPE: PRT
<213> ORGANISM: Artificial
<220> FEATURE:
<223> OTHER INFORMATION: Synthetic peptide

<400> SEQUENCE: 39

Val Thr Ala Leu Glu Pro Gln Ala Glu Gly Ala Leu
1               5                   10

<210> SEQ ID NO 40
<211> LENGTH: 15
<212> TYPE: PRT
<213> ORGANISM: Artificial
<220> FEATURE:
<223> OTHER INFORMATION: Synthetic peptide

<400> SEQUENCE: 40

Ile Asp Phe Gln Leu Gly Trp Asp Ala Asp Pro Glu Glu Glu Lys
1               5                   10                  15

<210> SEQ ID NO 41
<211> LENGTH: 20
<212> TYPE: PRT
<213> ORGANISM: Artificial
<220> FEATURE:
<223> OTHER INFORMATION: Synthetic peptide

<400> SEQUENCE: 41

Leu Ser Val Pro Ala Thr Leu His Gly Ser Ala Leu Asn Thr Pro Asp
1               5                   10                  15

Thr Asp Thr Phe
            20

<210> SEQ ID NO 42
<211> LENGTH: 20
<212> TYPE: DNA
<213> ORGANISM: Artificial
<220> FEATURE:
<223> OTHER INFORMATION: Synthetic primer Hy4R
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 42
tcytcnggrt cngcrtccca                                                   20

<210> SEQ ID NO 43
<211> LENGTH: 20
<212> TYPE: DNA
<213> ORGANISM: Artificial
<220> FEATURE:
<223> OTHER INFORMATION: Synthetic primer Hy5F
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 43
ggngtnggnc arccnatggt 20

<210> SEQ ID NO 44
<211> LENGTH: 6
<212> TYPE: PRT
<213> ORGANISM: Artificial
<220> FEATURE:
<223> OTHER INFORMATION: Synthetic consensus sequence
<220> FEATURE:
<221> NAME/KEY: MISC_FEATURE
<222> LOCATION: (2)..(5)
<223> OTHER INFORMATION: Xaa at positions 2, 4 and 5 can be any amino acid

<400> SEQUENCE: 44

Gly Xaa Gly Xaa Xaa Gly
1 5

<210> SEQ ID NO 45
<211> LENGTH: 11
<212> TYPE: PRT
<213> ORGANISM: Artificial
<220> FEATURE:
<223> OTHER INFORMATION: Synthetic consensus sequence
<220> FEATURE:
<221> NAME/KEY: MISC_FEATURE
<222> LOCATION: (4)..(10)
<223> OTHER INFORMATION: Xaa at positions 4, 5 and 10 can be any amino acid

<400> SEQUENCE: 45

Gly Arg Val Xaa Xaa Ala Gly Asp Ala Xaa His
1 5 10

<210> SEQ ID NO 46
<211> LENGTH: 29
<212> TYPE: PRT
<213> ORGANISM: Artificial
<220> FEATURE:
<223> OTHER INFORMATION: Synthetic consensus sequence
<220> FEATURE:
<221> NAME/KEY: MISC_FEATURE
<222> LOCATION: (2)..(27)
<223> OTHER INFORMATION: Xaa at positions 3, 3, 4, 6, 10-20, 23-34 and 26-27 can be any amino acid

<400> SEQUENCE: 46

Asp Xaa Xaa Xaa Leu Xaa Trp Lys Leu Xaa Xaa Xaa Xaa Xaa Xaa Xaa
1 5 10 15

Xaa Xaa Xaa Xaa Leu Leu Xaa Xaa Tyr Xaa Xaa Glu Arg
20 25

<210> SEQ ID NO 47
<211> LENGTH: 7
<212> TYPE: PRT

<213> ORGANISM: Artificial
<220> FEATURE:
<223> OTHER INFORMATION: Synthetic peptide

<400> SEQUENCE: 47

Met Thr Thr Lys Thr Phe Ala
1 5

<210> SEQ ID NO 48
<211> LENGTH: 25
<212> TYPE: DNA
<213> ORGANISM: Artificial
<220> FEATURE:
<223> OTHER INFORMATION: Synthetic primer Start ORF1

<400> SEQUENCE: 48
gcaggatgca catgtccacc aagac 25

<210> SEQ ID NO 49
<211> LENGTH: 25
<212> TYPE: DNA
<213> ORGANISM: Artificial
<220> FEATURE:
<223> OTHER INFORMATION: Synthetic primer ORF1 Fin

<400> SEQUENCE: 49
cggacgcaag cttgcatcag ccttc 25

<210> SEQ ID NO 50
<211> LENGTH: 32
<212> TYPE: DNA
<213> ORGANISM: Artificial
<220> FEATURE:
<223> OTHER INFORMATION: Synthetic primer N-CsVMV

<400> SEQUENCE: 50
gccctcgagg tcgacggtat tgatcagctt cc 32

<210> SEQ ID NO 51
<211> LENGTH: 25
<212> TYPE: DNA
<213> ORGANISM: Artificial
<220> FEATURE:
<223> OTHER INFORMATION: Synthetic primer C-CsVMV

<400> SEQUENCE: 51
cgctctagaa ttcagatcta caaac 25

<210> SEQ ID NO 52
<211> LENGTH: 25
<212> TYPE: DNA
<213> ORGANISM: Artificial
<220> FEATURE:
<223> OTHER INFORMATION: Synthetic primer Start ORF2

<400> SEQUENCE: 52
cagaggacga acaacatgtc ccacc 25

<210> SEQ ID NO 53
<211> LENGTH: 28
<212> TYPE: DNA
<213> ORGANISM: Artificial
<220> FEATURE:
<223> OTHER INFORMATION: Synthetic primer ORF2 fin3

<400> SEQUENCE: 53
ctgtggatga agcttaagag gttcaggc 28

```
<210> SEQ ID NO 54
<211> LENGTH: 23
<212> TYPE: DNA
<213> ORGANISM: Artificial
<220> FEATURE:
<223> OTHER INFORMATION: Synthetic primer N-CaMV

<400> SEQUENCE: 54

gcatgcctcg agcccacaga tgg                                              23


<210> SEQ ID NO 55
<211> LENGTH: 21
<212> TYPE: DNA
<213> ORGANISM: Artificial
<220> FEATURE:
<223> OTHER INFORMATION: Synthetic primer C-CaMV

<400> SEQUENCE: 55

ccacccgggg atcctctaga g                                                21


<210> SEQ ID NO 56
<211> LENGTH: 23
<212> TYPE: DNA
<213> ORGANISM: Artificial
<220> FEATURE:
<223> OTHER INFORMATION: Synthetic primer N-Nos

<400> SEQUENCE: 56

caagcttatc gataccgtcg acg                                              23


<210> SEQ ID NO 57
<211> LENGTH: 35
<212> TYPE: DNA
<213> ORGANISM: Artificial
<220> FEATURE:
<223> OTHER INFORMATION: Synthetic primer C-Nos

<400> SEQUENCE: 57

gssttgcggc cgcaattccc gacctaggaa catag                                 35


<210> SEQ ID NO 58
<211> LENGTH: 30
<212> TYPE: DNA
<213> ORGANISM: Artificial
<220> FEATURE:
<223> OTHER INFORMATION: Synthetic primer N-term-HPPO-ScaI

<400> SEQUENCE: 58

gaattcagta cttcacttac agtgtccggc                                       30


<210> SEQ ID NO 59
<211> LENGTH: 36
<212> TYPE: DNA
<213> ORGANISM: Artificial
<220> FEATURE:
<223> OTHER INFORMATION: Synthetic primer C-term-HPPO-AsuII-XhoI

<400> SEQUENCE: 59

gaattctcga gttcgaacaa actgagtagc agctca                                36


<210> SEQ ID NO 60
<211> LENGTH: 30
<212> TYPE: DNA
<213> ORGANISM: Artificial
<220> FEATURE:
<223> OTHER INFORMATION: Synthetic primer N-SH
```

<400> SEQUENCE: 60
gcttgcatgc ctaggtcgag gagaaatatg 30

<210> SEQ ID NO 61
<211> LENGTH: 25
<212> TYPE: DNA
<213> ORGANISM: Artificial
<220> FEATURE:
<223> OTHER INFORMATION: Synthetic primer C-SH

<400> SEQUENCE: 61
catgaggggt tcgaaatcga taagc 25

<210> SEQ ID NO 62
<211> LENGTH: 24
<212> TYPE: DNA
<213> ORGANISM: Artificial
<220> FEATURE:
<223> OTHER INFORMATION: Synthetic primer N-Hister

<400> SEQUENCE: 62
ctagacctag ggatccccc gatc 24

<210> SEQ ID NO 63
<211> LENGTH: 34
<212> TYPE: DNA
<213> ORGANISM: Artificial
<220> FEATURE:
<223> OTHER INFORMATION: Synthetic primer C-Hister

<400> SEQUENCE: 63
cccactagtg tttaaatgat cagtcaggcc gaat 34

<210> SEQ ID NO 64
<211> LENGTH: 400
<212> TYPE: DNA
<213> ORGANISM: Arthrobacter globiformis

<400> SEQUENCE: 64
tttggaaatc gacgggatcc agcggaccag cactgccatc tccgtcgtgg agctcatgcc 60
gccccgctat gacggcctgc tggcccggct gtcccagcag gagagccgcc atcccagcta 120
gggcataggt gatccgcacc acctttgagc atatttgcag tagctactgt gataaactgc 180
caaaaatacc agctcatgtc tgttcacttg ccaatcgctg atccagatcc gacgattcct 240
gcatgacttc acttacagtg tccggccggg tggcgcaggt cctcagcagc tatgtcagcg 300
ggcgaaggag gcggtggcgg gctagggccg gcctcgtcga aatgccgccc tccaacccaa 360
ctcagtacca gctcagggcg ttctcagggc tgggaacgcc 400

<210> SEQ ID NO 65
<211> LENGTH: 400
<212> TYPE: DNA
<213> ORGANISM: Arthrobacter globiformis

<400> SEQUENCE: 65
ggcgttccca gccctgagaa cgccctgagc tggtactgag ttgggttgga gggcggcatt 60
tcgacgaggc cggccctagc ccgccaccgc ctccttcgcc cgctgacata gctgctgagg 120
acctgcgcca cccggccgga cactgtaagt gaagtcatgc aggaatcgtc ggatctggat 180
cagcgattgg caagtgaaca gacatgagct ggtatttttg gcagtttatc acagtagcta 240
ctgcaaatat gctcaaaggt ggtgcggatc acctatgccc tagctgggat ggcggctctc 300

```
ctgctgggac agccgggcca gcaggccgtc atagcggggc ggcatgagct ccacgacgga    360

gatggcagtg ctggtccgct ggatcccgtc gatttccaaa                          400


<210> SEQ ID NO 66
<211> LENGTH: 49
<212> TYPE: PRT
<213> ORGANISM: Artificial
<220> FEATURE:
<223> OTHER INFORMATION: synthetic sequence

<400> SEQUENCE: 66

Gly Leu Arg Phe Thr Ala Val Arg His Glu Gly Ala Ala Ile Ala Ala
1               5                   10                  15

Ala Asp Ala Tyr Tyr Arg Ala Ser Gly Arg Leu Ala Ala Gly Thr Thr
            20                  25                  30

Thr Tyr Gly Pro Gly Tyr Thr Asn Ala Leu Thr Ala Leu Ala Glu Ala
        35                  40                  45

Val


<210> SEQ ID NO 67
<211> LENGTH: 49
<212> TYPE: PRT
<213> ORGANISM: Artificial
<220> FEATURE:
<223> OTHER INFORMATION: Synthetic sequence

<400> SEQUENCE: 67

Ser Ile Arg Ile Ile Pro Val Arg His Glu Ala Asn Ala Ala Phe Met
1               5                   10                  15

Ala Ala Ala Val Gly Arg Ile Thr Gly Lys Ala Gly Val Ala Leu Val
            20                  25                  30

Thr Ser Gly Pro Gly Cys Ser Asn Leu Ile Thr Gly Met Ala Thr Ala
        35                  40                  45

Asn


<210> SEQ ID NO 68
<211> LENGTH: 49
<212> TYPE: PRT
<213> ORGANISM: Artificial
<220> FEATURE:
<223> OTHER INFORMATION: Synthetic sequence

<400> SEQUENCE: 68

Gly Ile Arg His Ile Thr Thr Arg His Glu Gln Gly Ala Thr His Ala
1               5                   10                  15

Ala Asp Gly Tyr Ala Arg Ala Ser Gly Lys Val Gly Val Ala Phe Ala
            20                  25                  30

Thr Ser Gly Pro Gly Ala Thr Asn Thr Val Thr Gly Ile Ala Thr Ala
        35                  40                  45

Tyr


<210> SEQ ID NO 69
<211> LENGTH: 49
<212> TYPE: PRT
<213> ORGANISM: Artificial
<220> FEATURE:
<223> OTHER INFORMATION: Synthetic sequence

<400> SEQUENCE: 69

Gln Ile Arg His Ile Leu Ala Arg His Glu Gln Gly Ala Gly Phe Ile
1               5                   10                  15
```

```
Ala Gln Gly Met Ala Arg Thr Asp Gly Lys Pro Ala Val Cys Met Ala
            20                  25                  30

Cys Ser Gly Pro Gly Ala Thr Asn Leu Val Thr Ala Ile Ala Asp Ala
        35                  40                  45

Arg


<210> SEQ ID NO 70
<211> LENGTH: 50
<212> TYPE: PRT
<213> ORGANISM: Artificial
<220> FEATURE:
<223> OTHER INFORMATION: Synthetic sequence

<400> SEQUENCE: 70

Asp Arg Ile His Tyr Ile Gln Val Arg His Glu Glu Val Gly Ala Met
1               5                   10                  15

Ala Ala Ala Ala Asp Ala Lys Leu Thr Gly Lys Ile Gly Val Cys Phe
            20                  25                  30

Gly Ser Ala Gly Pro Gly Gly Thr His Leu Met Asn Gly Leu Tyr Asp
        35                  40                  45

Ala Arg
    50


<210> SEQ ID NO 71
<211> LENGTH: 49
<212> TYPE: PRT
<213> ORGANISM: Artificial
<220> FEATURE:
<223> OTHER INFORMATION: Synthetic sequence

<400> SEQUENCE: 71

Gly Ile Glu Trp Val His Val Arg His Glu Glu Thr Ala Ala Phe Ala
1               5                   10                  15

Ala Gly Ala Glu Ala Gln Ile Thr Gly Lys Leu Thr Ala Cys Ala Gly
            20                  25                  30

Ser Cys Gly Pro Gly Asn Leu His Leu Ile Asn Gly Leu Tyr Asp Ala
        35                  40                  45

His


<210> SEQ ID NO 72
<211> LENGTH: 49
<212> TYPE: PRT
<213> ORGANISM: Artificial
<220> FEATURE:
<223> OTHER INFORMATION: Synthetic sequence

<400> SEQUENCE: 72

Arg Ala Val Asp Asp Gly Asn Ile Leu Val Leu Ala Ala Gly Asp Gly
1               5                   10                  15

Gly Phe Leu Met Gly Leu Ser Asp Leu Glu Ser Leu Val Gly Ala Ala
            20                  25                  30

Ser Ser Ala Val Val Val Ile Tyr Asn Asp Ala Ala Tyr Gly Ala Glu
        35                  40                  45

Ile


<210> SEQ ID NO 73
<211> LENGTH: 49
<212> TYPE: PRT
<213> ORGANISM: Artificial
<220> FEATURE:
<223> OTHER INFORMATION: Synthetic sequence
```

<400> SEQUENCE: 73

```
Leu Val Asn Pro Gln Arg Lys Val Val Ser Val Ser Gly Asp Gly Gly
1               5                   10                  15

Phe Leu Gln Ser Ser Met Glu Leu Glu Thr Ala Val Arg Leu His Ala
            20                  25                  30

Asn Ile Leu His Ile Ile Trp Val Asp Asn Gly Tyr Asn Met Val Ala
        35                  40                  45

Ile
```

<210> SEQ ID NO 74
<211> LENGTH: 48
<212> TYPE: PRT
<213> ORGANISM: Artificial
<220> FEATURE:
<223> OTHER INFORMATION: Synthetic sequence

<400> SEQUENCE: 74

```
Val Ala Phe Pro Glu Lys Thr Val Ile Asp Ile Ala Gly Asp Gly Ser
1               5                   10                  15

Phe Phe Met Asn Ile Gln Glu Leu Ala Thr Cys Val Lys Tyr Glu Ile
            20                  25                  30

Pro Val Lys Val Leu Val Leu Asn Asn Gly Tyr Leu Gly Met Val Arg
        35                  40                  45
```

<210> SEQ ID NO 75
<211> LENGTH: 48
<212> TYPE: PRT
<213> ORGANISM: Artificial
<220> FEATURE:
<223> OTHER INFORMATION: Synthetic sequence

<400> SEQUENCE: 75

```
Leu Ala Asn Pro Asp Arg Lys Val Leu Cys Phe Ser Gly Asp Gly Ser
1               5                   10                  15

Leu Met Met Asn Ile Gln Glu Met Ala Thr Ala Ser Glu Asn Gln Leu
            20                  25                  30

Asp Val Lys Ile Ile Leu Met Asn Asn Glu Ala Leu Gly Leu Val His
        35                  40                  45
```

<210> SEQ ID NO 76
<211> LENGTH: 49
<212> TYPE: PRT
<213> ORGANISM: Artificial
<220> FEATURE:
<223> OTHER INFORMATION: Synthetic sequence

<400> SEQUENCE: 76

```
Leu Asn Tyr Pro Glu Arg Gln Val Phe Asn Leu Ala Gly Asp Gly Gly
1               5                   10                  15

Ala Ser Met Thr Met Gln Asp Leu Ala Thr Gln Val Gln Tyr His Leu
            20                  25                  30

Pro Val Ile Asn Val Val Phe Thr Asn Cys Gln Tyr Gly Phe Ile Lys
        35                  40                  45

Asp
```

<210> SEQ ID NO 77
<211> LENGTH: 48
<212> TYPE: PRT
<213> ORGANISM: Artificial
<220> FEATURE:
<223> OTHER INFORMATION: Synthetic sequence

<400> SEQUENCE: 77

```
Phe Thr Asp Arg Arg Arg Gln Val Val Ser Met Ser Gly Asp Gly Gly
1               5                   10                  15

Phe Thr Met Leu Met Gly Asp Phe Leu Thr Leu Val Gln His Asp Leu
            20                  25                  30

Pro Val Lys Ile Val Leu Phe Asn Asn Ser Ser Leu Gly Met Val Glu
        35                  40                  45
```

<210> SEQ ID NO 78
<211> LENGTH: 50
<212> TYPE: PRT
<213> ORGANISM: Artificial
<220> FEATURE:
<223> OTHER INFORMATION: Synthetic sequence

<400> SEQUENCE: 78

```
Gln Ser Ile His Ile Pro Tyr Glu Arg His Ala Asp Gln Asp Ala Gly
1               5                   10                  15

Ala Asp Thr Pro Ala Arg His Pro Val Val Ile Val Gly Ala Gly Pro
            20                  25                  30

Val Gly Leu Ser Leu Ala Ile Asp Leu Ala Gln Arg Gly Gln Arg Val
        35                  40                  45

Val Leu
    50
```

<210> SEQ ID NO 79
<211> LENGTH: 26
<212> TYPE: PRT
<213> ORGANISM: Artificial
<220> FEATURE:
<223> OTHER INFORMATION: Synthetic sequence

<400> SEQUENCE: 79

```
Met Val Val Ala Gly Ala Gly Pro Thr Gly Leu Met Leu Ala Cys Glu
1               5                   10                  15

Leu Ala Leu Gly Gly Ala Arg Ala Val Val
            20                  25
```

<210> SEQ ID NO 80
<211> LENGTH: 50
<212> TYPE: PRT
<213> ORGANISM: Artificial
<220> FEATURE:
<223> OTHER INFORMATION: Synthetic sequence

<400> SEQUENCE: 80

```
Ser Arg Pro Ile Arg Phe Arg Ile Met Ser Ile Cys Glu Arg Ile Gly
1               5                   10                  15

Met Leu Pro Cys Ser Glu Lys Lys Val Phe Ile Val Gly Gly Gly Pro
            20                  25                  30

Cys Gly Leu Met Leu Ser Ile Asp Leu Ser Arg Arg Gly Ile Pro Ser
        35                  40                  45

Ile Leu
    50
```

<210> SEQ ID NO 81
<211> LENGTH: 30
<212> TYPE: PRT
<213> ORGANISM: Artificial
<220> FEATURE:
<223> OTHER INFORMATION: Synthetic sequence

<400> SEQUENCE: 81

```
Met Asp Ala Ser Val Ile Val Ala Gly Ala Gly Pro Thr Gly Leu Met
1               5                   10                  15

Leu Ala Gly Glu Leu Arg Leu Ala Gly Val Asp Val Ile Val
            20                  25                  30
```

<210> SEQ ID NO 82
<211> LENGTH: 43
<212> TYPE: PRT
<213> ORGANISM: Artificial
<220> FEATURE:
<223> OTHER INFORMATION: Synthetic sequence

<400> SEQUENCE: 82

```
Met Ala Ile Gln His Pro Asp Ile Gln Pro Ala Val Asn His Ser Val
1               5                   10                  15

Gln Val Ala Ile Ala Gly Ala Gly Pro Val Gly Leu Met Met Ala Asn
            20                  25                  30

Tyr Leu Gly Gln Met Gly Ile Asp Val Leu Val
        35                  40
```

<210> SEQ ID NO 83
<211> LENGTH: 32
<212> TYPE: PRT
<213> ORGANISM: Artificial
<220> FEATURE:
<223> OTHER INFORMATION: Synthetic sequence

<400> SEQUENCE: 83

```
Met Ala Asp Pro Thr Arg Val Leu Val Ala Gly Ala Gly Pro Val Gly
1               5                   10                  15

Leu Thr Ala Ala His Glu Leu Ala Arg Arg Gly Leu Arg Val Arg Leu
            20                  25                  30
```

<210> SEQ ID NO 84
<211> LENGTH: 48
<212> TYPE: PRT
<213> ORGANISM: Artificial
<220> FEATURE:
<223> OTHER INFORMATION: Synthetic sequence

<400> SEQUENCE: 84

```
Ala Leu Gln Leu Pro Leu Ile Asp Leu Arg Trp His Ser Lys Val Thr
1               5                   10                  15

Ala Leu Glu Pro Gln Ala Glu Gly Ala Leu Leu Thr Val Glu Thr Pro
            20                  25                  30

Asp Gly Ser Tyr Arg Ile Asp Ala Gln Trp Val Leu Ala Cys Asp Gly
        35                  40                  45
```

<210> SEQ ID NO 85
<211> LENGTH: 43
<212> TYPE: PRT
<213> ORGANISM: Artificial
<220> FEATURE:
<223> OTHER INFORMATION: Synthetic sequence

<400> SEQUENCE: 85

```
Ala Arg Glu Leu Gly Val Arg Ile Val Arg Gly Ser Gly Val Thr Gly
1               5                   10                  15

Phe Ala Gln Asp Ala Asp Gly Val Thr Val Glu Thr Asp Thr Gly Leu
            20                  25                  30

Leu Arg Ala Arg Tyr Leu Val Gly Cys Asp Gly
        35                  40
```

<210> SEQ ID NO 86
<211> LENGTH: 50
<212> TYPE: PRT
<213> ORGANISM: Artificial
<220> FEATURE:
<223> OTHER INFORMATION: Synthetic sequence

<400> SEQUENCE: 86

Ala Glu Ala Ser Glu Leu Ala Ser Val Asn Tyr Gly Trp Arg Met Ile
1 5 10 15

Asp Phe Glu Gln Gly Ala Asp Gly Val Ser Ala Thr Val Glu Glu Ala
20 25 30

Ala Thr Gly Lys Gln Gln Lys Ile Arg Ala Glu Tyr Leu Val Gly Ala
35 40 45

Asp Gly
50

<210> SEQ ID NO 87
<211> LENGTH: 48
<212> TYPE: PRT
<213> ORGANISM: Artificial
<220> FEATURE:
<223> OTHER INFORMATION: Synthetic sequence

<400> SEQUENCE: 87

Ala Arg Glu Leu Gly Ala Asp Ile Arg Arg Gly His Glu Leu Val Thr
1 5 10 15

Leu His Asp His Gly Asp His Val Glu Ala Glu Val Arg Gly Pro Glu
20 25 30

Asp Glu Lys Ile Arg Leu Thr Ala Pro Tyr Leu Val Gly Cys Asp Gly
35 40 45

<210> SEQ ID NO 88
<211> LENGTH: 49
<212> TYPE: PRT
<213> ORGANISM: Artificial
<220> FEATURE:
<223> OTHER INFORMATION: Synthetic sequence

<400> SEQUENCE: 88

Val Ser Arg Phe Pro Asn Val Arg Cys Leu Phe Ser Arg Glu Leu Glu
1 5 10 15

Ala Phe Ser Gln Gln Asp Asp Glu Val Thr Leu His Leu Lys Thr Ala
20 25 30

Glu Gly Gln Arg Glu Ile Val Lys Ala Gln Trp Leu Val Ala Cys Asp
35 40 45

Gly

<210> SEQ ID NO 89
<211> LENGTH: 48
<212> TYPE: PRT
<213> ORGANISM: Artificial
<220> FEATURE:
<223> OTHER INFORMATION: Synthetic sequence

<400> SEQUENCE: 89

Val Ala Arg Leu Gly Val Asp Val Glu Trp Glu Thr Arg Leu Thr Gly
1 5 10 15

Phe Ser Gln Asp Ala Glu Gly Val Asp Val Thr Leu Glu His Ala Asp
20 25 30

Gly Thr Thr Glu Ser Thr Arg Val Pro Trp Leu Val Gly Cys Asp Gly 35 40 45

<210> SEQ ID NO 90
<211> LENGTH: 50
<212> TYPE: PRT
<213> ORGANISM: Artificial
<220> FEATURE:
<223> OTHER INFORMATION: Synthetic sequence

<400> SEQUENCE: 90

Leu Leu Gly Lys Asp Ala Pro Phe Glu Leu Glu Trp Ala Ser Val Tyr
1 5 10 15

Thr Phe Ala Cys Leu Arg Met Asp Arg Phe Val His Gly Arg Val Val
20 25 30

Phe Ala Gly Asp Ser Ala His Gly Val Ser Pro Phe Gly Ala Arg Gly
35 40 45

Ala Asn
50

<210> SEQ ID NO 91
<211> LENGTH: 48
<212> TYPE: PRT
<213> ORGANISM: Artificial
<220> FEATURE:
<223> OTHER INFORMATION: Synthetic sequence

<400> SEQUENCE: 91

Ser Asp His Gly Met His Asp Val Thr Trp Leu Ser Arg Leu Thr Asp
1 5 10 15

Val Ser Arg Leu Ala Asp Ser Tyr Arg Leu Gly Arg Val Leu Leu Ala
20 25 30

Gly Asp Ala Ala His Ile His Leu Pro Ala Gly Gly Gln Gly Leu Asn
35 40 45

<210> SEQ ID NO 92
<211> LENGTH: 49
<212> TYPE: PRT
<213> ORGANISM: Artificial
<220> FEATURE:
<223> OTHER INFORMATION: Synthetic sequence

<400> SEQUENCE: 92

Gly Met Ala Leu Asp Ile Glu Ile Ile Asp Met Gly Thr Trp Val Ala
1 5 10 15

Gly His Ala Leu Tyr Val Glu Gln Met Val Ser Gly Arg Val Ile Leu
20 25 30

Ala Gly Asp Ala Ala His Leu Phe Thr Pro Ala Gly Gly Leu Gly Tyr
35 40 45

Asn

<210> SEQ ID NO 93
<211> LENGTH: 48
<212> TYPE: PRT
<213> ORGANISM: Artificial
<220> FEATURE:
<223> OTHER INFORMATION: Synthetic sequence

<400> SEQUENCE: 93

Ile Asp Ile Ser His Ala Glu His Glu Trp Val Ser Ala Phe Gly Asp
1 5 10 15

Ala Thr Arg Leu Val Thr Glu Tyr Arg Arg Gly Arg Val Leu Leu Ala
20 25 30

```
Gly Asp Ala Ala His Ile His Leu Pro Ala Gly Gly Gln Gly Met Asn
        35                  40                  45


<210> SEQ ID NO 94
<211> LENGTH: 48
<212> TYPE: PRT
<213> ORGANISM: Artificial
<220> FEATURE:
<223> OTHER INFORMATION: Synthetic sequence

<400> SEQUENCE: 94

Pro Asn Pro Asp Asn Val Glu Leu Ile Arg Gln Arg Val Tyr Thr His
1               5                   10                  15

Asn Ala Arg Leu Ala Gln Arg Phe Arg Ile Asp Arg Val Leu Leu Ala
            20                  25                  30

Gly Asp Ala Ala His Ile Met Pro Val Trp Gln Gly Gln Gly Tyr Asn
        35                  40                  45


<210> SEQ ID NO 95
<211> LENGTH: 47
<212> TYPE: PRT
<213> ORGANISM: Artificial
<220> FEATURE:
<223> OTHER INFORMATION: Synthetic sequence

<400> SEQUENCE: 95

Val Arg Gln Val Arg Thr Pro Thr Trp Thr Ser Val Phe Thr Phe Gln
1               5                   10                  15

Gln Arg Met Val Pro Arg Met Gly Glu Gly Arg Val Phe Val Ala Gly
            20                  25                  30

Asp Ala Ala His Val His Ser Pro Ala Ser Gly Arg Gly Met Asn
        35                  40                  45


<210> SEQ ID NO 96
<211> LENGTH: 46
<212> TYPE: PRT
<213> ORGANISM: Artificial
<220> FEATURE:
<223> OTHER INFORMATION: Synthetic sequence

<400> SEQUENCE: 96

Ser Gly Val Gln Asp Ala Glu Asn Leu Ala Trp Lys Leu Asp Arg Val
1               5                   10                  15

Leu Arg Gly Gln Ala Asp Ala Ser Leu Ile Ala Thr Tyr Gly Ala Glu
            20                  25                  30

Arg Glu Tyr Ala Ala Asp Glu Asn Ile Arg Asn Ser Thr Arg
        35                  40                  45


<210> SEQ ID NO 97
<211> LENGTH: 46
<212> TYPE: PRT
<213> ORGANISM: Artificial
<220> FEATURE:
<223> OTHER INFORMATION: Synthetic sequence

<400> SEQUENCE: 97

Leu Gly Phe Gln Asp Ala Val Asn Leu Gly Trp Lys Leu Ala Ala Val
1               5                   10                  15

Val Arg Gly His Gly Thr Glu Glu Leu Leu Asp Ser Tyr Gly Arg Glu
            20                  25                  30

Arg Arg Pro Ile Ala Asp Gly Val Val Arg Asn Thr Arg Thr
        35                  40                  45
```

```
<210> SEQ ID NO 98
<211> LENGTH: 50
<212> TYPE: PRT
<213> ORGANISM: Artificial
<220> FEATURE:
<223> OTHER INFORMATION: Synthetic sequence

<400> SEQUENCE: 98

Thr Ala Val Glu Asp Ala Val Asn Leu Gly Trp Lys Leu Ala Ala Ile
1               5                   10                  15

Leu Lys Gly Gln Ala Gly Pro Glu Leu Leu Ala Ser Tyr Glu Phe Glu
            20                  25                  30

Arg Ser Lys Leu Ala Lys Arg Asn Thr Gly Tyr Ala Arg Gly Leu Ala
        35                  40                  45

Asp Ser
    50


<210> SEQ ID NO 99
<211> LENGTH: 46
<212> TYPE: PRT
<213> ORGANISM: Artificial
<220> FEATURE:
<223> OTHER INFORMATION: Synthetic sequence

<400> SEQUENCE: 99

Thr Gly Ile Gln Asp Ala Val Asn Leu Gly Trp Lys Leu Ala Ala Val
1               5                   10                  15

Leu Arg Gly Thr Ala Ser Glu Ser Leu Leu Asp Ser Tyr His Ser Glu
            20                  25                  30

Arg His Ala Val Gly Glu Arg Leu Met Met Asn Thr Lys Ala
        35                  40                  45


<210> SEQ ID NO 100
<211> LENGTH: 46
<212> TYPE: PRT
<213> ORGANISM: Artificial
<220> FEATURE:
<223> OTHER INFORMATION: Synthetic sequence

<400> SEQUENCE: 100

Ser Gly Met Arg Asp Ala Phe Asn Leu Ala Trp Lys Leu Ala Leu Val
1               5                   10                  15

Ile Gln Gly Lys Ala Arg Asp Ala Leu Leu Asp Thr Tyr Gln Gln Glu
            20                  25                  30

Arg Arg Asp His Ala Lys Ala Met Ile Asp Leu Ser Val Thr
        35                  40                  45


<210> SEQ ID NO 101
<211> LENGTH: 46
<212> TYPE: PRT
<213> ORGANISM: Artificial
<220> FEATURE:
<223> OTHER INFORMATION: Synthetic sequence

<400> SEQUENCE: 101

Thr Gly Val Gln Glu Ala Tyr Asn Leu Ala Trp Lys Leu Ala Leu Val
1               5                   10                  15

Ala Glu Gly His Ala Glu Arg Glu Leu Leu Asp Ser Tyr Ser Leu Glu
            20                  25                  30

Arg Val Pro Ile Gly Glu Arg Leu Leu Gly Ser Thr Lys Lys
        35                  40                  45
```

HERBICIDE-TOLERANT PLANTS THROUGH BYPASSING METABOLIC PATHWAY

REFERENCE TO RELATED APPLICATIONS

This application is a divisional of application Ser. No. 10/415,302 filed Aug. 29, 2003 now U.S. Pat. No. 7,304,209, which is the National Stage of International Application No. PCT/FR01/03364 filed Oct. 30, 2001, which claims the benefit of French Patent Application No. FR 00/13942 filed Oct. 30, 2000.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: 5500-169 Sequence Listing, date recorded: Oct. 29, 2007, size: 158 KB.

FIELD OF THE INVENTION

The present invention relates to a novel method for making plants tolerant to herbicides, in particular to HPPD-inhibiting herbicides, to the nucleic acid sequences encoding enzymes which can be used in this method, to the expression cassettes containing them and to the transgenic plants comprising at least one of these expression cassettes.

BACKGROUND OF THE INVENTION

Hydroxyphenylpyruvate dioxygenases are enzymes which catalyze the reaction of conversion of para-hydroxyphenylpyruvate (HPP) to homogentisate. This reaction takes place in the presence of iron ($Fe^{2+}$) in the presence of oxygen (N. P. Crouch et al., Tetrahedron, 53, 20, 6993-7010, 1997).

Certain molecules which inhibit this enzyme are, moreover, known, which attach to the enzyme so as to inhibit the conversion of HPP to homogentisate. Some of these molecules have found a use as herbicides, insofar as inhibition of the reaction in plants leads to a bleaching of the leaves of the treated plants and to the death of said plants (K. E. Pallett et al., 1997 Pestic. Sci. 50 83-84). Such herbicides having HPPD as the target, described in the state of the art, are in particular isoxazoles (EP 418 175, EP 470 856, EP 487 352, EP 527 036, EP 560 482, EP 682,659, U.S. Pat. No. 5,424,276), in particular isoxaflutole, a herbicide selective for maize, diketonitriles (EP 496 630, EP 496 631), in particular 2-cyano-3-cyclopropyl-1-(2-$SO_2CH_3$-4-$CF_3$-pheny-1)propane-1,3-dione and 2-cyano-3-cyclopropyl-1-(2-$SO_2CH_3$-4-2,3-$Cl_2$-phenyl))propane-1,3-dione, triketones (EP 625 505, EP 625 508, U.S. Pat. No. 5,506,195), in particular sulcotrione or mesotrione, or else pyrazolinates.

Assays to confirm that HPPD is indeed the target for diketonitriles (DKNS) and to demonstrate that HPPD is, at least at certain doses, the only target for diketonitriles, were carried out in the laboratory by germinating *Arabidopsis* seeds on three types of medium under sterile conditions in vitro:

1 Murashige and Skoog medium (T. Murashige and F. Skoog, 1962. A revised medium for a rapid growth and bioassays with tobacco tissue culture. Physiol. Plant. 15, 473-479), control experiment for germination 2 MS medium plus DKN at a dose of 1 ppm 3 MS medium plus DKN at the same dose+homogentisate at a concentration of 5 mM.

It is very clear that, on medium 1, germination occurs normally, each plantlet developing two cotyledons which are clearly green. Development then takes place normally. On medium 2, germination occurs, but the plantlet which emerges is white, the two cotyledons exhibiting no pigmentation. The plantlets then die in a few days. On medium 3, germination occurs normally, the cotyledons are clearly green. The plants develop, but very rapidly, the amount of homogentisate in the medium decreasing, the first symptoms of bleaching appear and plant growth stops, they end up dying as in the assay carried out on medium No. 2.

This makes it possible to confirm that HPPD is clearly the target for DKNs in plants and that it appears to be the only target. This also shows that homogentisate is transported from the culture medium to the cell site where it is necessary for correct functioning of the cell and survival of the plant.

Three strategies are currently available to make plants tolerant to herbicides, (1) detoxification of the herbicide with an enzyme which converts the herbicide, or its active metabolite, to nontoxic degradation products, such as, for example, the enzymes for tolerance to bromoxynil or to basta (EP 242 236, EP 337 899); (2) mutation of the target enzyme to a functional enzyme less sensitive to the herbicide, or its active metabolite, such as, for example, the enzymes for tolerance to glyphosate (EP 293 356, S. R. Padgette et al., J. Biol. Chem., 266, 33, 1991); or (3) overexpression of the sensitive enzyme, so as to produce in the plant amounts of target enzyme which are sufficient with regard to the kinetic constants of this enzyme with respect to the herbicide in order to have sufficient functional enzyme, despite the presence of its inhibitor.

This third strategy which has been described for successfully obtaining plants tolerant to HPPD inhibitors (WO 96/38567), it being understood that, for the first time, a strategy of simple overexpression of the sensitive (nonmutated) target enzyme, was used successfully to impart on plants tolerance at an agronomic level to a herbicide. The identification of HPPDs mutated in the C-terminal portion which exhibit improved tolerance to HPPD inhibitors has made it possible to obtain an improvement in the tolerance of plants using the second strategy (WO 99/24585).

SUMMARY OF THE INVENTION

The present invention consists of a novel method for making plants tolerant to a herbicide, which uses a novel or fourth strategy of herbicide tolerance, this novel strategy comprising bypassing the metabolic pathway inhibited by said herbicide. This metabolic bypassing can be summarized as follows:

- for instance a herbicide "H" which is active by inhibiting the activity of an enzyme "E" which converts the, substrate "S" to product "P", said product P and its metabolites being essential to the life of the plant,
- the metabolic bypassing consists in expressing in the plant at least one novel heterologous enzyme "NE" insensitive to "H" allowing conversion of "S" to an intermediate product "I", which product is then converted into "P" either via the natural biosynthesis pathways of the plant or via the expression of at least one other heterologous enzyme "OE" also insensitive to "H",
- the metabolic bypassing also consisting in expressing at least one other heterologous enzyme "OE" insensitive to "H" allowing conversion of "I" to "P", "I" being an intermediate either naturally produced by the plant or obtained by expressing at least one novel heterologous enzyme "NE" insensitive to "H" allowing conversion of "S" to "I".

The present invention relates more particularly to a novel method for making plants tolerant to HPPD inhibitors, said method comprising the metabolic bypassing of HPPD.

No pathway of metabolic bypassing has been described to date in plants.

BRIEF DESCRIPTION OF THE DRAWINGS

FIG. 3 shows a diagram of a vector containing hppO and restriction sites.

FIG. 4 shows part of a 936 bp nucleotide sequence identified by PCR potentially encoding part of hppO (SEQ ID NO: 64) and complementary sequence (SEQ ID NO: 65)

FIG. 5 shows amino acid sequence alignments of HPPoxydase (upper SEQ ID NO: 66; lower SEQ ID NO: 72), D47069 (upper SEQ ID NO: 67; lower SEQ ID NO: 73), G69464 (upper SEQ ID NO: 68; lower SEQ ID NO: 74), YCEC1L (upper SEQ ID NO: 69; lower SEQ ID NO: 75), P37603 (upper SEQ ID NO: 70; lower SEQ ID NO: 76), and T34668 (upper SEQ ID NO: 71; lower SEQ ID NO: 77).

FIG. 7 shows a diagram of the 5.2 kb insert of plasmid p5kbC.

FIG. 8 shows amino acid sequence alignments of HPAH, hydroxylase-Q53657, monoxygenase-Q9EAM4, putative oxygenase-Q5471, MHPA_ECOLI and Oxygenase-086481 and consensus sequence.

In A, HPAH (SEQ ID NO: 78), hydroxylase-Q53657 (SEQ ID NO: 79), monoxygenase-Q9EAM4 (SEQ ID NO: 80), putative oxygenase-Q5471 (SEQ ID NO: 81), MHPA_E-COLI (SEQ ID NO: 82), Oxygenase-086481 (SEQ ID NO: 83) and consensus sequence (SEQ ID NO: 43).

In B, HPAH (SEQ ID NO: 84), hydroxylase-Q53657 (SEQ ID NO: 85), monoxygenase-Q9EAM4 (SEQ ID NO: 86), putative oxygenase-Q5471 (SEQ ID NO: 87), MHPA_E-COLI (SEQ ID NO: 88), Oxygenase-086481 (SEQ ID NO: 89).

In C, HPAH (SEQ ID NO: 90), hydroxylase-Q53657 (SEQ ID NO: 91), monoxygenase-Q9EAM4 (SEQ ID NO: 92), putative oxygenase-Q5471 (SEQ ID NO: 93), MHPA_E-COLI (SEQ ID NO: 94), Oxygenase-086481 (SEQ ID NO: 95) and consensus sequence (SEQ ID NO: 44).

In D, HPAH (SEQ ID NO: 96), hydroxylase-Q53657 (SEQ ID NO: 97), monoxygenase-Q9EAM4 (SEQ ID NO: 98), putative oxygenase-Q5471 (SEQ ID NO: 99), MHPA_E-COLI (SEQ ID NO: 100), Oxygenase-086481 (SEQ ID NO: 101) and consensus sequence (SEQ ID NO: 45).

FIG. 9 shows a diagram of plasmid pL1lac2.

Figure 10:
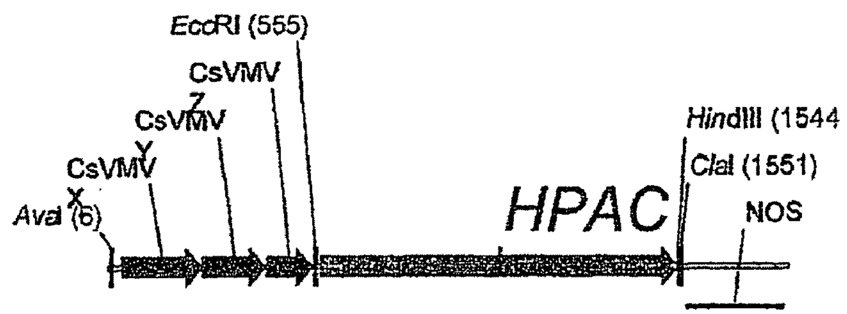

FIG. 10 shows an expression cassette encoding an HPAC.

Figure 11:
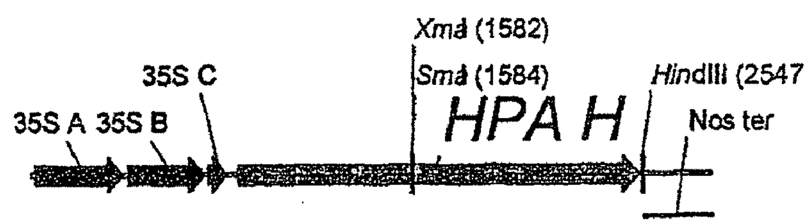

FIG. 11 shows an expression cassette encoding an HPAH.

Figure 12:
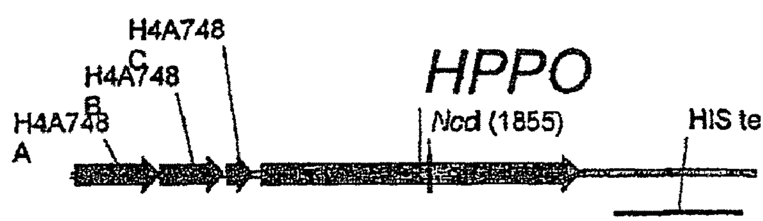

FIG. 12 shows an expression cassette encoding HPP oxidase.

Figure 13:
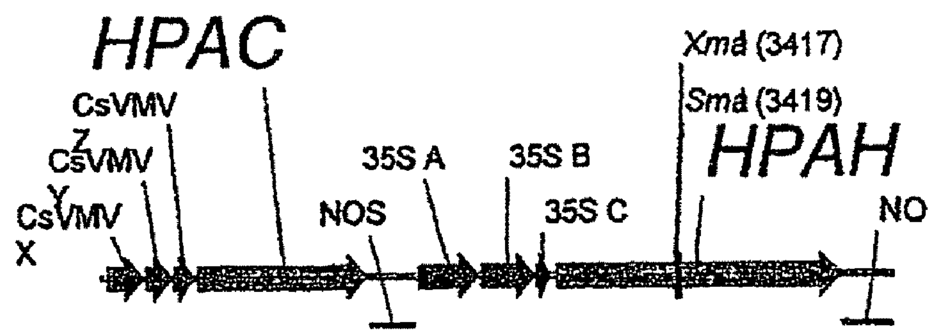

FIG. 13 shows an expression cassette encoding both HPAH and HPAC.

Figure 14:
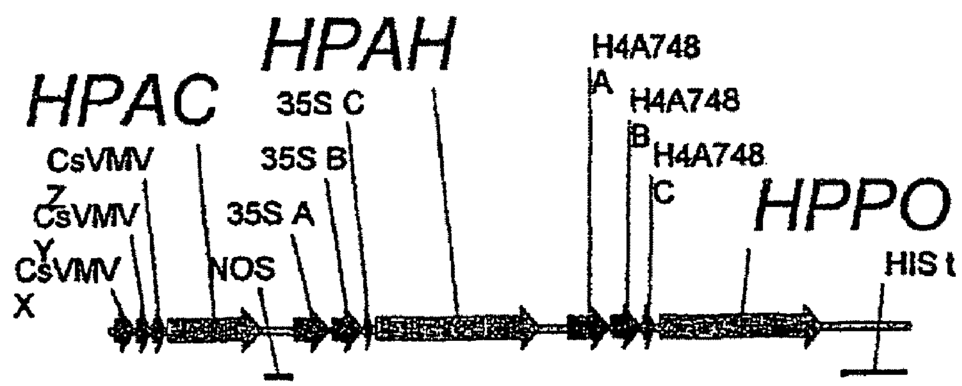

FIG. 14 shows an expression cassette encoding HPP oxidase, HPAH and HPAC.

DETAILED DESCRIPTION OF THE INVENTION

Figure 1:
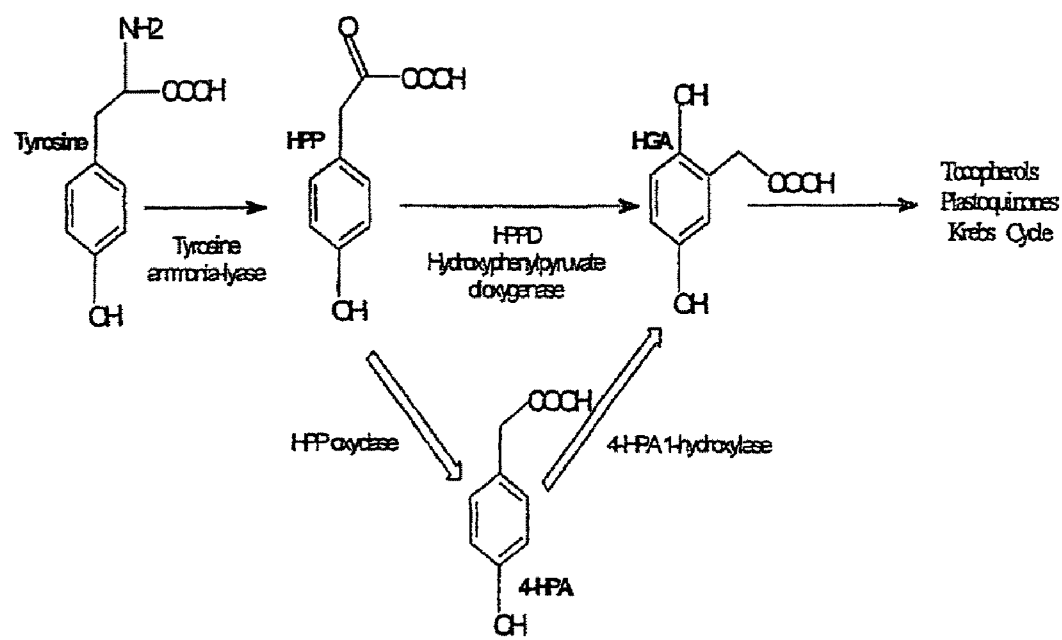
FIG. 1 shows a schematic pathway of conversion of HPP to homogentisate.

It is known from the literature that the conversion of HPP to homogentisate can be obtained by first carrying out conversion of HPP to 4-hydroxyphenylacetic acid (4-HPA) with an enzyme extract exhibiting HPP oxidase activity, followed by conversion of 4-HPA to homogentisate with an enzyme extract exhibiting 4-HPA 1-hydrolase activity (WO 99/34008). This bypassing pathway is represented in FIG. 1.

A bibliographical study reveals that the enzyme activities required to construct the HPPD bypassing pathway were characterized on crude bacterial extracts in the 1970s. Thus, the HPP oxidase (HPPO, E.C. 1.2.3.-) and 4-HPA 1-hydroxylase (HPAH, E.C. 1.14.13.18) activities were identified respectively in *Arthrobacter globiformis* (Blakley, 1977) and in *Pseudomonas acidovarans* (Hareland et al., 1975). Since then, only HPAH has been purified, by Suemori et al., (1996), but neither the protein sequence nor the nucleic acid, sequence are published. It is therefore necessary to identify the genes encoding these enzyme activities.

In the bypassing pathway, the conversion of HPP to HGA takes place via 4-HPA. Now, 4-HPA is a compound rarely identified in plants. It is present in *Astilbe chinensis* (Kindl, 1969), in *Plantago* sp. (Swiatek, 1977) in dandelion (*Taraxacum officinale*; Dey & Harborne, 1997), in *Artemisia* (Swiatek et al., 1998), in the fruit of *Forsythia suspensa* (Liu et al., 1998) and, finally, in the marine alga *Ulva lactuca* (Flodin et al., 1999). There is little data regarding origin. It appears to be able to originate from tyrosine, from shikimate, or from tyramine. There is no more information on this regarding what becomes of it or its role in plants. Kindl (1969) has shown its degradation via 3,4-dihydroxyphenylacetic acid, while Flodin et al. (1999) have demonstrated its conversion via 4-hydroxymandelic acid to 2,4,6-tribromophenol, which accumulates in the green alga *Ulva lactuca*. Gross (1975) suggests that 4-HPA might be a growth regulator in certain higher plants, and Abe et al. (1974) consider it to be an analog of auxin in algae.

In order to implement the pathway of metabolic bypassing of HPPD, it would have been necessary to identify and isolate beforehand the genes and the nucleic acid sequences encoding the enzyme(s) responsible for the two activities above.

DEFINITIONS ACCORDING TO THE INVENTION

"Nucleic acid sequence": a nucleotide or polynucleotide sequence, which can be of the DNA or RNA type, preferably of the DNA type, in particular double stranded. The nucleic acid sequence may be of natural origin, in particular genomic DNA or cDNA, or else a synthetic or semisynthetic sequence, the nucleic acids comprising it having been chosen either to optimize the codons of a coding sequence as a function of the host organism in which it will be expressed, or to introduce or eliminate one or more restriction sites. Methods for preparing synthetic or semisynthetic nucleic acid sequences are well known to those skilled in the art.

"Sequence capable of selectively hybridizing": the nucleic acid sequences which hybridize with a reference nucleic acid sequence at a level significantly greater than the background noise. The background noise may be associated with the hybridization of other DNA sequences present, in particular of other cDNAs present in a cDNA library. The level of the signal generated by the interaction between the sequence capable of selectively hybridizing and the sequences defined by the sequence IDs above according to the invention is generally 10 times, preferably 100 times, greater than that of the interaction of the other DNA sequences generating the background noise. The level of interaction can be measured, for example, by labeling the probe with radioactive elements such as $^{32}P$. The selective hybridization is generally obtained by using very severe conditions for the medium (for example 0.03 M NaCl and 0.03 M sodium citrate at approximately 50° C.-60° C.). The hybridization can of course be carried out according to the usual methods of the state of the art (in particular Sambrook et al., 1989. Molecular Cloning: A Laboratory Manual).

"Homolog of a nucleic acid sequence": nucleic acid sequence exhibiting one or more sequence modifications compared to a reference nucleic acid sequence. These modifications can be obtained according to the usual techniques of mutation, or else by choosing the synthetic oligonucleotides used in the preparation of said sequence by hybridization. With regard to the multiple combinations of nucleic acids which can result in the expression of the same amino acid, the differences between the reference sequence according to the invention and the corresponding homolog may be considerable. Advantageously, the degree of homology will be at least 60% compared to the reference sequence, preferably at least 70%, more preferentially at least 80%, even more preferentially at least 90%. These modifications are generally and preferably neutral, that is to say that, for a coding sequence, they do not affect the primary sequence of the protein or of the peptide encoded. They may, however, introduce nonsilent modifications, or mutations, which do not affect the function of the nucleic acid sequence compared to the reference sequence. The methods for measuring and identifying the homologies between nucleic acid sequences are well known to those skilled in the art. The PILEUP or BLAST programs (in particular Altschul et al., 1993, J. Mol. Evol. 36:290-300; Altschul et al., 1990, J. Mol. Biol. 215:403-10) can for example be used.

"Fragments": fragment of a reference nucleic acid or polypeptide sequence for which portions have been deleted but which conserves the function of said reference sequence.

"Heterolog": nucleic acid sequence different from the nucleic acid sequence having the same function in a natural organism. A heterologous sequence may consist of a nucleic acid sequence modified in situ in its natural environment. It may also be a nucleic acid sequence isolated from its natural organism then reintroduced into this same organism. It may also be a nucleic acid sequence which is heterologous with respect to another nucleic acid sequence, i.e. a sequence associated with another sequence, this association not occurring naturally. This is in particular the case of expression cassettes consisting of various nucleic acid sequences which are not generally associated naturally.

"Homolog of a protein sequence": protein sequences in which the primary sequence is different from the primary sequence of the reference protein, but which performs the same function as this reference sequence. The methods for measuring and identifying homologies between polypeptides or proteins are also known to those skilled in the art. The UWGCG package and the BESTFITT program can for example be used to calculate the homologies (Deverexu et al., 1984, Nucleic Acid Res. 12, 387-395).

"Expression cassette": nucleic acid sequence comprising various functional elements required for the expression of a coding sequence in a host organism. These functional elements comprise, in the direction of transcription, a regulatory promoter sequence, also called promoter, functionally linked to a coding sequence and a regulatory terminator sequence, also called terminator or stop. The expression cassette can also comprise, between the regulatory promoter sequence and the coding sequence, regulatory elements such as transcription activators, or enhancers, and/or introns.

"Host organism": according to the invention this is essentially intended to mean plant cells or plants. For the cloning vectors, the host organisms can also be bacteria, fungi or yeasts.

"Plant cells": cell which is derived from a plant and which can constitute undifferentiated tissues such as calluses, differentiated tissues such as embryos, parts of plants, plants or seeds.

"Plant": differentiated multicellular organism capable of photosynthesis, in particular monocotyledonous or dicotyledonous, more particularly crop plants which may or may not be intended for animal or human food, such as rice, maize, wheat, barley, sugar cane, rapeseed, soybean, beetroot, potato, tobacco, cotton, clover, turf, or ornamental plants such as petunias, or else banana plants, grapevines, raspberries, strawberries, tomatoes, salad plants, etc.

"Regulatory promoter sequence": as a regulatory promoter sequence in plants, use may be made of any regulatory promoter sequence of a gene which is naturally expressed in plants, in particular a promoter which is expressed in particular in the leaves of plants, such as, for example, "constitutive" promoters of bacterial, viral or plant origin, or else "light-dependent" promoters such as that of a gene of the plant ribulose-biscarboxylase/oxygenase (RuBisCO) small subunit, or any known suitable promoter which can be used. Among the promoters of plant origin, mention will be made of the histone promoters as described in application EP 0 507 698, or the rice actin promoter (U.S. Pat. No. 5,641,876). Among the promoters of a plant virus gene, mention will be made of that of the cauliflower mosaic virus (CAMV 19S or 35S), or of CsVMV (US . . . ), or the circovirus promoter (AU 689 311). Use may also be made of a regulatory promoter sequence specific for particular regions or tissues of plants, and more particularly seed-specific promoters ([22] R. Datla et al., Biotechnology Ann. Rev. (1997) 3, 269-296), especially the promoters for napin (EP 255 378), for phaseolin, for glutenin, for heliantinin (WO 92/17580), for albumin (WO 98/45460), for oleosin (WO 98/45461), for ATS1 or for ATS3 (PCT/US98/06978, filed on Oct. 20, 1998, incorporated herein by way of reference). Use may also be made of an inducible promoter advantageously chosen from the, promoters for phenylalanine ammonia lyase (PAL), for HMG-CoA reductase (HMG), for chitinases, for glucanases, for proteinase inhibitors (PI), for PR1 family genes, for nopaline synthase (nos) or for the vspB gene (U.S. Pat. No. 5,670,349, Table 3), the HMG2 promoter (U.S. Pat. No. 5,670,349), the apple beta-galactosidase (ABG1) promoter or the apple aminocyclopropane carboxylate synthase (ACC synthase) promoter (WO 98/45445).

"Transcription activators (enhancers)": mention will be made, for example, of the enhancer of the tobacco mosaic virus (TMV) described in application WO 87/07644, or of the tobacco etch virus (TEV) described by Carrington & Freed.

"Introns": untranslated nucleic acid sequences. Mention will be made, for example, of intron 1 of the *Arabidopsis* histone gene as described in patent application WO 97/04114 for expression in dicotyledonous plants, the rice actin first intron described in patent application WO 99/34005, or the maize adh1 intron for expression in monocotyledonous plants.

"Coding sequence": translated nucleic acid sequence. It comprises a sequence encoding a protein or a peptide of interest, optionally fused in the 5' or in the 3' position, with a sequence encoding a signal peptide or a peptide for addressing to a particular cellular compartment.

"Signal peptide or addressing peptide": peptides fused to a protein or a peptide of interest in their N- or C-terminal portions, recognized by the cellular machinery for addressing of the protein or of the peptide of interest to a particular cellular compartment. They are in particular chloroplast transit peptides for addressing the protein or the peptide of interest into chloroplasts, or signal peptides to various cellular compartments, for example the vacuole, the mitochondria, the endoplastic reticulum, the golgi apparatus, etc. The role of such protein sequences is in particular described in issue 38 of the review Plant molecular Biology (1998) devoted in large part to the transport of proteins into the various compartments of the plant cell (Sorting of proteins to vacuoles in plant cells pp 127-144; the nuclear pore complex pp 145-162; protein translocation into and across the chloroplastic envelope membranes pp 91-207; multiple pathways for the targeting of thylakoid proteins in chloroplasts pp 209-221; mitochondrial protein import in plants pp 311-338).

"Chloroplast transit peptide": the chloroplast transit peptide is encoded by a: nucleic acid sequence positioned 5' of the nucleic acid sequence encoding a protein or a peptide of interest, so as to allow the expression of a transit peptide/protein (peptide) of interest fusion protein. The transit peptide makes it possible to address the protein or the peptide of interest into plasts, more particularly chloroplasts, the fusion protein being cleaved between the transit peptides and the protein or the peptide of interest as it passes through the plast membrane. The transit peptide may be single, such as an EPSPS transit peptide (U.S. Pat. No. 5,188,642) or a transit peptide from the ribulose-biscarboxylase/oxygenase small subunit (RuBisCO ssu) of a plant, optionally comprising some amino acids of the N-terminal portion of the mature RuBisCO ssu (EP 189 707), or else a multiple transit peptide comprising a first plant transit peptide fused to a portion of the N-terminal sequence of a mature protein located in plastids, fused to a second plant transit peptide as described in patent EP 508 909, and more particularly the optimized transit peptide comprising a transit peptide of sunflower RuBisCO ssu fused to 22 amino acids of the N-terminal end of maize RuBisCO ssu fused to the transit peptide of maize RuBisCO ssu as described with its coding sequence in patent EP 508 909.

"Signal peptide": these peptide sequences are in particular described in issue 38 of the review Plant molecular Biology (1998) devoted in large part to the transport of proteins into the various compartments of the plant cell (Sorting of proteins to vacuoles in plant cells pp 127-144; the nuclear pore complex pp 145-162; protein translocation into and across the chloroplastic envelope membranes pp 91-207; multiple pathways for the targeting of thylakoid proteins in chloroplasts pp 209-221; mitochondrial protein import in plants pp 311-338). Peptides for addressing to the vacuole are widely described in the literature (J. M. Neuhaus and J. C. Rogers Sorting of proteins to vacuoles in plant cells Plant molecular Biology 38: 127-144, 1998). Preferably, the vacuole peptide is the vacuole peptide of the protein described in J. M. Ferullo et al. (Plant Molecular Biology 33: 625-15, 633, 1997), fused to the C-terminal portion of the protein or of the peptide of interest.

"Regulatory terminator sequence": also comprising the polyadenylation sequences, this is intended to mean any sequence which is functional in plant cells or plants, whether of bacterial origin, such as, for example, the nos terminator of *Agrobacterium tumefaciens*, of viral origin, such as, for example, the CaMV 35S terminator, or else of plant origin, such as, for example, a histone terminator as described in application EP 0 633 317.

"Vector": cloning and/or expression vector for the transformation of a host organism, containing at least one expression cassette. The vector comprises, beside the expression cassette, at least one origin of replication. The vector may consist of a plasmid, a cosmid, a bacteriophage or a virus, transformed by introducing the expression cassette. Such transformation vectors, as a function of the host organism to be transformed, are well known to those skilled in the art and widely described in the literature. For the transformation of plant cells or plants, it will in particular be a virus which can be used to transform developed plants and which also contains its own elements for replication and for expression.

Preferentially, the vector for transforming plant cells or plants is a plasmid.

HPP Oxidase

A first subject of the invention concerns a nucleic acid sequence encoding an HPP oxidase, and the corresponding polypeptide. Preferentially, the HPP oxidase is insensitive to HPPD inhibitors, in particular to isoxazoles such as isoxaflutole and their diketonitriles, in particular those defined above. The HPP oxidase is in particular an HPP oxidase of bacterial origin, for example from *Arthrobacter*, in particular from *Arthrobacter globiformis*. The HPP oxidase is advantageously a protein the primary amino acid sequence of which is represented by sequence identifier No. 2 (SEQ ID No. 2) the sequences homologous thereto and the fragments thereof.

Protein sequences of HPP oxidases homologous to SEQ ID No. 2 are in particular represented by SEQ ID Nos. 4 and 6, the sequences homologous thereto and the fragments thereof.

The HPP oxidase represented by SEQ ID No. 4 corresponds to the HPP oxidase of SEQ ID No. 2 for which a glycine is replaced with an alanine.

The present invention also relates to a nucleic acid sequence encoding an HPP oxidase as defined above.

Preferentially, the sequence encoding the HPP oxidase is a DNA sequence, especially genomic DNA or cDNA, in particular a heterologous or isolated sequence.

The sequence encoding an HPP oxidase according to the invention is in particular chosen from, the coding sequences of the DNA sequences represented by SEQ ID No. 1, 3, 5 or 15, the sequences homologous thereto, the fragments thereof, and the sequences capable of selectively hybridizing to SEQ ID 1, 3, 5 or 15.

The coding sequence of SEQ ID No. 5 comprises three mutations at positions 463, 602 and 1511 relative to SEQ ID No. 1, which are silent, i.e. which introduce no modification of the corresponding polypeptide.

4-HPA 1-Hydroxylase

A second subject of the invention concerns the means required for the expression of 4-HPA 1-hydroxylase. Contrary to what was expected from the literature regarding the activity of certain protein extracts, it was noted that the 4-HPA 1-hydroxylase activity in the bacteria, in particular *Pseudomonas*, resulted from the sum of the activity of two enzymes, hereinafter referred to HPAH and HPAC.

HPAH

Figure 2:
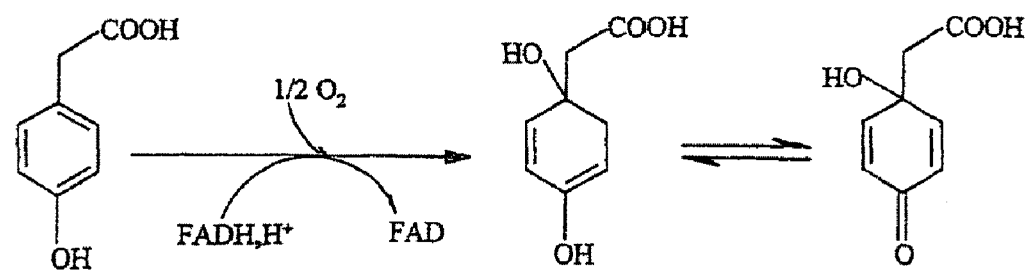
FIG. 2 shows a schematic enzyme pathway starting with HPA.

HPAH allows the conversion of HPA to an intermediate metabolite, hereinafter referred to as metabolite Z, the structure of which remains undetermined. It may be seriously envisaged that HPAH allows hydroxylation of the aromatic ring of HPA, the metabolite Z stabilizing in the form of a ketone. This hypothesis of enzyme activity is represented in FIG. 2.

A second subject of the invention therefore concerns a nucleic acid sequence encoding an HPAH, and the corresponding polypeptide. Preferentially, the HPAH is insensitive to HPPD inhibitors, in particular to isoxazoles such as isoxaflutole and their diketonitriles, especially those defined above. The HPAH is in particular an HPAH of bacterial origin, for example from *Pseudomonas*, in particular from

*Pseudomonas acidovorans*. The HPAH is advantageously a protein the primary amino acid sequence of which is represented by sequence identifiers No. 8 and 18 (SEQ ID No. 8 and SEQ ID No. 18), the sequences homologous thereto and the fragments thereof.

The present invention also relates to a nucleic acid sequence encoding an HPAH as defined above.

Preferentially, the sequence encoding the HPAH is a DNA sequence, especially genomic DNA or cDNA, in particular a heterologous or isolated sequence.

The sequence encoding an HPAH according to the invention is in particular chosen from the coding regions of the sequences represented by SEQ ID No. 7 or 17 the sequences homologous thereto, the fragments thereof, and the sequences capable of selectively hybridizing to SEQ ID No. 7 or 17.

HPAC

HPAC is the second enzyme which allows conversion of the metabolite Z to homogentisate.

A third subject of the invention therefore concerns a nucleic acid sequence encoding an HPAC, and the corresponding polypeptide. Preferentially, the HPAC is insensitive to HPPD inhibitors, in particular to isoxazoles such as isoxaflutole and their diketonitriles, especially those defined above. The HPAC is in particular an HPAC of bacterial origin, for example from *Pseudomonas*, in particular from *Pseudomonas acidovorans*. The HPAC is advantageously a protein the primary amino acid sequence of which is represented by sequence identifier No. 10 (SEQ ID No. 10), the sequences homologous thereto and the fragments thereof.

Protein sequences of HPAC homologous to SEQ ID No. 10 are in particular represented by SEQ ID Nos. 12, 14 and 20, the sequences homologous thereto and the fragments thereof.

The present invention also relates to a nucleic acid sequence encoding an HPAC as defined above.

Preferentially, the sequence encoding the HPAC is a DNA sequence, especially genomic DNA or cDNA, in particular a heterologous or isolated sequence.

The sequence encoding an HPAC according to the invention is in particular chosen from the coding regions of the sequences represented by SEQ ID No. 9, 11, 13 or 19, the sequences homologous thereto, the fragments thereof, and the sequences capable of selectively hybridizing to SEQ ID No. 9, 11, 13 or 19.

Expression Cassettes

The present invention also relates to an expression cassette the coding sequence of which comprises a nucleic acid sequence selected from the nucleic acid sequences encoding an HPP oxidase, an HPAH or HPAC as defined above.

The coding sequence can also comprise, in the 5' or in the 3' position, a sequence encoding a signal peptide or a transit peptide. Advantageously, the coding sequence comprises, positioned 5' of the sequence encoding HPP oxidase, an HPAH or an HPAC, and a sequence encoding a transit peptide for chloroplast addressing, in particular a multiple transit peptide, more particularly the optimized transit peptide.

The present invention therefore also relates to a transit peptide/HPP oxidase, transit peptide/HPAH or transit peptide/HPAC fusion protein, the sequence of the transit peptide being defined above, in particular the sequence of the optimized transit peptide as described in patent application EP 508 909.

Preferentially, the regulatory promoter sequence is chosen from the regulatory promoter sequences allowing constitutive expression of the coding sequence. These are in particular the sequences of the CaMV 35S, CsVMV, rice actin or histone promoters.

It is also possible to choose to express the coding sequences according to the invention at a level of expression close to the level of expression of the gene intended to be bypassed. Use may be made, in the expression cassette according to the invention, of a regulatory promoter sequence chosen from the regulatory promoter sequences of plant HPPDs.

For expression of the three enzymes HPP oxidase, HPAH and HPAC in the same plant, it is possible choose the expression cassettes for the corresponding coding sequences, different regulatory promoter sequences exhibiting different expression profiles, by virtue of their strength and/or their location in the various functional organs of the plant.

Regulatory promoter sequences allowing a gradient of expression HPAC>HPAH>HPP oxidase, or vice versa, may be chosen.

For expression of HPP oxidase, of the HPAH and of the HPAC, the regulatory promoter sequence is advantageously chosen from the group comprising the promoters of plant HPPD, of histone H3 or H4, especially from *Arabidopsis* or from maize, in particular those described in patent application EP 507 698, and of plant RuBisCO SSU, in particular from sunflower or from maize as described in patent application WO 99/25842, the CaMV 35S promoter or the CsVMV promoter, and combinations thereof, in particular the histone/35S hybrid promoters as described in the examples of patent application EP 507 698. For expression in monocotyledonous plants, these regulatory promoter sequences will advantageously be combined with the first intron of rice actin.

According to one embodiment of the invention, the expression cassette encoding an HPP oxidase comprises a histone promoter, a sequence encoding an HPP oxidase and a histone terminator (FIG. 12; SEQ ID No. 15).

According to another embodiment of the invention, the expression cassette encoding an HPAH comprises a CaMV 35S promoter, a sequence encoding an HPAH and a NOS terminator (FIG. 11; SEQ ID No. 17).

According to another embodiment of the invention, the expression cassette encoding an HPAC comprises a CsVMV promoter, a sequence encoding an HPAC and a NOS terminator (FIG. 10; SEQ ID No. 19).

Vectors:

The present invention also relates to a cloning and/or expression vector comprising at least one expression cassette according to the invention.

According to a first embodiment of the invention, the vector comprises just one of the expression cassettes according to the invention, chosen from the cassettes comprising a coding sequence for an HPP oxidase, an HPAH or an HPAC as defined above.

According to a second embodiment of the invention, the vector comprises two expression cassettes according to the invention, chosen from the cassettes comprising a coding sequence for an HPP oxidase, an HPAH or an HPAC as defined above, combined in pairs in the same vector: HPP oxidase and HPAH, HPP oxidase and HPAC, HPAH and HPAC.

A vector comprising an expression cassette encoding the HPAH and another encoding the HPAC can comprise the combination of the two expression cassettes defined above (SEQ ID No. 17 and 19). Such an expression cassette is represented in FIG. 13 and SEQ ID No. 21.

According to a third embodiment of the invention, the vector comprises three expression cassettes according to the invention, a first expression cassette for the HPP oxidase, a second expression cassette for the HPAH and a third expression cassette for the HPAC. Such an expression cassette can comprise the combination of the three cassettes defined above (SEQ ID Nos. 15, 17 and 19). Such a vector is represented in FIG. 14 and SEQ ID No. 22.

The vectors according to the invention as defined above can also comprise expression cassettes for other proteins or peptides of interest.

When the vector comprises several expression cassettes, these cassettes can have various orientations in pairs with respect to one another, colinear, divergent or convergent.

The expression cassettes for other proteins or peptides of interest comprise a nucleic acid sequence encoding proteins or peptides of interest different than the HPP oxidase, the HPAH and the HPAC defined above.

There may be sequences of a gene encoding a selectable marker, such as a gene imparting novel agronomic properties to the transformed plant, or a gene which improves the agronomic quality of the transformed plant.

Selectable Markers

Among the genes encoding selectable markers, mention may be made of the genes for resistance to antibiotics, the genes for tolerance to herbicides, (bialaphos, glyphosate or isoxazoles), genes encoding readily identifiable reporter enzymes such as the GUS enzyme, genes encoding pigments or enzymes regulating the production of pigments in the transformed cells. Such selectable marker genes are in particular described in patent applications EP 242 236, EP 242 246, GB 2 197 653, WO 91/02071, WO 95/06128, WO 96/38567 or WO 97/04103.

Genes of Interest

Among the genes which impart novel agronomic properties to the transformed plants, mention may be made of the genes which impart tolerance to certain herbicides, those which impart resistance to certain insects, those which impart tolerance to certain diseases, etc. Such genes are in particular described in patent applications WO 91/02071 and WO 95/06128.

Herbicide Tolerance

The present invention is particularly suitable for the expression of genes which impart tolerance to certain herbicides to the transformed monocotyledonous plants and plant cells. Among the genes imparting tolerance to certain herbicides, mention may be made of the Bar gene imparting tolerance to bialaphos, the gene encoding a suitable EPSPS imparting resistance to herbicides having EPSPS as the target, such as glyphosate and its salts (U.S. Pat. No. 4,535,060, U.S. Pat. No. 4,769,061, U.S. Pat. No. 5,094,945, U.S. Pat. No. 4,940,835, U.S. Pat. No. 5,188,642, U.S. Pat. No. 4,971,908, U.S. Pat. No. 5,145,783, U.S. Pat. No. 5,310,667, U.S. Pat. No. 5,312,910, U.S. Pat. No. 5,627,061, U.S. Pat. No. 5,633,435, FR 2 736 926), the gene encoding glyphosate oxidoreductase (U.S. Pat. No. 5,463,175), or else a gene encoding an HPPD imparting tolerance to herbicides having HPPD as the target, such as isoxazoles, in particular isoxaflutole (FR 95 06800, FR 95 13570), diketonitriles (EP 496 630, EP 496 631) or triketones, in particular sulcotrione (EP 625 505, EP 625 508, U.S. Pat. No. 5,506,195). Such genes encoding an HPPD imparting tolerance to herbicides having HPPD as the target are described in patent application WO 96/38567.

Among the genes encoding a suitable EPSPS imparting resistance to herbicides having EPSPS as the target, mention will be made more particularly of the gene encoding a plant EPSPS, in particular from maize, exhibiting two mutations, 102 and 106, described in patent application FR 2 736 926, referred to below as EPSPS double mutant, or else the gene encoding an EPSPS isolated from *Agrobacterium* described by sequence ID 2 and ID 3 of U.S. Pat. No. 5,633,435, referred to below as CP4.

Among the genes encoding an HPPD imparting tolerance to herbicides having HPPD as the target, mention will be made more particularly of the HPPD from *Pseudomonas* and that from *Arabidopsis*, described in patent application WO 96/38567.

In the cases of the genes encoding EPSPS or HPPD, and more particularly encoding the genes above, the sequence encoding these enzymes is advantageously preceded by a sequence encoding a transit peptide, in particular encoding the transit peptide termed "optimized transit peptide" described in U.S. Pat. No. 5,510,471 or 5,633,448.

Resistance to Insects

Among the proteins of interest imparting novel properties of resistance to insects, mention will be made more particularly of the Bt proteins widely described in the literature and well known to those skilled in the art. Mention will also be made of the proteins extracted from bacteria such as *Photorabdus* (WO 97/17432 and WO 98/08932).

Resistance to Diseases

Among the proteins or peptides of interest imparting novel properties of resistance to diseases, mention will be made in particular of chitinases, glucanases and oxalate oxidase, all these proteins and their coding sequences being widely described in the literature or else antibacterial and/or antifungal peptides, in particular cysteine-rich peptides of less than 100 amino acids, such as plant thionins or defensins, and more particularly lytic peptides of all origins comprising one or more disulfide bridges between the cysteines and regions comprising basic amino acids, in particular the following lytic peptides: androctonin (WO 97/30082 and PCT/FR98/01814, filed on Aug. 18, 1998) or drosomycin (PCT/FR98/01462, filed on Jul. 8, 1998).

According to a particular embodiment of the invention, the protein or peptide of interest is chosen from fungal elicital peptides, in particular elicitins (Kamoun et al., 1993; Panabires et al., 1995).

Modification of the Quality

Mention may also be made of the genes which modify the constitution of the modified plants, in particular the content and the quality of certain essential fatty acids (EP 666 918) or else the content and the quality of the proteins, in particular in the leaves and/or the seeds of said plants. Mention will in particular be made of the genes encoding proteins enriched in sulfur-containing amino acids (A. A. Korit et al., Eur. J. Biochem. (1991) 195, 329-334; WO 98/20133; WO 97/41239; WO 95/31554; WO 94/20828; WO 92/14822). These proteins enriched in sulfur-containing amino acids will also have the function of trapping and storing excess cysteine and/or methionine, making it possible to avoid possible problems of toxicity associated with overproduction of these sulfur-containing amino acids by trapping them. Mention may also be made of genes encoding peptides rich in sulfur-containing amino acids, and more particularly in cysteines, said peptides also having an antibacterial and/or antifungal activity. Mention will more particularly be made of plant defensins, along with lytic peptides of any origin, and more particularly the following lytic peptides: androctonin (WO 97/30082 and PCT/FR98/01814, filed on Aug. 18, 1998) or drosomycin (PCT/FR98/01462, filed on Jul. 8, 1998).

Plant Cells and Transgenic Plants

The present invention also relates to transformed plant cells and plants comprising at least one expression cassette for an HPP oxidase, for an HPAH or for an HPAC as defined above.

According to a first embodiment of the invention, the plant cells or the plants comprise just one of the expression cassettes according to the invention, chosen from the cassettes comprising a coding sequence for an HPP oxidase, an HPAH or an HPAC as defined above.

According to a second embodiment of the invention, the plant cells or the plants comprise two expression cassettes according to the invention, chosen from the cassettes comprising a coding sequence for an HPP oxidase, an HPAH or an HPAC as defined above, combined in pairs in the same vector: HPP oxidase and HPAH, HPP oxidase and HPAC, HPAH and HPAC.

According to a third embodiment of the invention, the plant cells or the plants comprise three expression cassettes according to the invention, a first expression cassette for HPP oxidase, a second expression cassette for HPAH and a third expression cassette for HPAC.

The plant cells or the plants according to the invention as defined above can also comprise expression cassettes for other proteins or peptides of interest defined above.

Preferentially, the expression cassettes are stably integrated into the genome of the plant cells or of the plants. More preferentially, the plants according to the invention are fertile, the expression cassettes according to the invention being transferred to their descendance.

The present invention also relates to seeds of transgenic plants above, which seeds comprise an expression cassette according to the invention encoding an HPP oxidase, an HPAH or an HPAC.

The various expression cassettes in the transformed plants according to the invention can originate either from the same transformed parent plant, and in this case, the plant is derived from a single process of transformation/regeneration with the various expression cassettes contained in the same vector or by cotransformation using several vectors. It may also be obtained by crossing parent plants each containing at least one expression cassette according to the invention.

Transformation of the Plant Cells and of the Plants

A subject of the invention is also a method of transforming the plant cells and the plants by introducing at least one nucleic acid sequence or an expression cassette according to the invention as defined above, which transformation can be obtained by any suitable known means, widely described in the specialized literature and in particular the references cited in the present application, more particularly with the vector according to the invention.

A series of methods consists in bombarding cells, protoplasts or tissues with particles to which the DNA sequences are attached. Another series of methods consists in using, as means for transfer into the plant, a chimeric gene inserted into an *Agrobacterium tumefaciens* Ti plasmid or an *Agrobacterium rhizogenes* Ri plasmid. Other methods can be used, such as microinjection or electroporation, or else direct precipitation using PEG. Those skilled in the art will choose the appropriate method as a function of the nature of the host organism, in particular of the plant cell or of the plant.

When the desire is to introduce several nucleic acid sequences or expression cassettes, it can be done using a single vector according to the invention comprising the various expression cassettes. They may also be introduced into the host organism by cotransformation using several vectors, each one comprising at least one expression cassette.

In general, the transgenic plants according to the invention are obtained by transformation of plant cells and then regeneration of a plant, preferably fertile, from the transformed cell. The regeneration is obtained by any suitable method, which depends on the nature of the species, such as for example described in the references above. For the methods of transforming the plant cells and of regenerating the plants, mention will in particular be made of the following patents and patent applications: U.S. Pat. No. 4,459,355, U.S. Pat. No. 4,536,475, U.S. Pat. No. 5,464,763, U.S. Pat. No. 5,177,010, U.S. Pat. No. 5,187,073, EP 267,159, EP 604 662, EP 672 752, U.S. Pat. No. 4,945,050, U.S. Pat. No. 5,036,006, U.S. Pat. No. 5,100,792, U.S. Pat. No. 5,371,014, U.S. Pat. No. 5,478,744, U.S. Pat. No. 5,179,022, U.S. Pat. No. 5,565,346, U.S. Pat. No. 5,484,956, U.S. Pat. No. 5,508,468, U.S. Pat. No. 5,538,877, U.S. Pat. No. 5,554,798, U.S. Pat. No. 5,489,520, U.S. Pat. No. 5,510,318, U.S. Pat. No. 5,204,253, U.S. Pat. No. 5,405,765, EP 442 174, EP 486 233, EP 486 234, EP 539 563, EP 674 725, WO 91/02071 and WO 95/06128.

Selective Weeding

A subject of the invention is also a method for selective weeding of plants, in particular crops, using an HPPD inhibitor, in particular a herbicide defined above, characterized in that this herbicide is applied to transformed plants according to the invention, equally in pre-sowing, in pre-emergence and in post-emergence of the crop.

The present invention also relates to a method of weed killing in an area of a field comprising seeds or transformed plants according to the invention, which method comprises the application, in said area of the field, of a dose, which is toxic for said weeds, of an HPPD-inhibiting herbicide, without however substantially affecting the seeds or transformed plants according to the invention.

The present invention also relates to a method of growing the transformed plants according to the invention, which method comprises sowing the seeds of said transformed plants in an area of a field suitable for growing said plants, applying to said area of said field a dose, which is toxic for the weeds, of a herbicide having HPPD as the target, defined above, in the event of weeds being present, without substantially affecting said seeds or said transformed plants, then harvesting the plants grown, when they have reached the desired maturity and, optionally, separating the seeds from the harvested plants.

According to the invention, the expression "without substantially affecting said seeds or said transformed plants" is intended to mean that the transformed plants according to the invention, subjected to application of a dose of herbicide which is toxic for the weeds, exhibit slight or zero phytotoxicity. According to the invention, the expression "dose which is toxic for the weeds" is intended to mean an applied dose of the herbicide for which the weeds are killed. According to the invention, the, term "slight phytotoxicity" is intended to mean a percentage of bleached leaves of less than 25%, preferentially less than 10%, more preferentially less than 5%. It is also understood according to the present invention that application of the same toxic dose to a plant which is otherwise comparable but not transformed, i.e. which does not comprise at least one expression cassette according to the invention, would lead to the observation on said plant of phytoxicity symptoms greater than those observed for the transformed plant according to the invention.

In the two methods above, the application of the herbicide having HPPD as the target can be carried out according to the invention, equally in pre-sowing, in pre-emergence and in post-emergence of the crop.

For the purpose of the present invention, the term "herbicide" is intended to mean a herbicidal active material alone or combined with an additive which modifies its effectiveness, such as, for example, an agent which increases the activity (synergist) or which limits the activity (safener). The HPPD-inhibiting herbicides are in particular defined previously. Of course, for their practical application, the herbicides above are combined, in a manner known per se, with the adjuvants of formulations conventionally used in agrochemistry.

When the transformed plant according to the invention comprises another gene for tolerance to another herbicide (such as, for example, a gene encoding an EPSPS, which may or may not be mutated, imparting to the plant tolerance to glyphosate), or when the transformed plant is naturally insensitive to another herbicide, the method according to the invention may comprise the simultaneous application or the application at a different time of an HPPD inhibitor in combination with said herbicide, for example glyphosate.

The various aspects of the invention will be understood more clearly through the experimental examples below.

All the methods or operations described below in these examples are given by way of examples and correspond to a choice, made from the various methods available to achieve the same result. This choice has no bearing on the quality of the result and, consequently, any suitable method can be used by those skilled in the art to achieve the same result. Most of the methods for engineering DNA fragments are described in Coligan et al., (1995), Ausubel et al., (1995); Maniatis et al., (1982) and Sambrook et al.

The bibliographical references cited above are integrated into the present patent application by way of reference, in particular the bibliographical references defining the nucleic acid sequences encoding native, chimeric or mutated HPPDs, optionally combined with a signal peptide or a transit peptide.

Example I

Identification of the Gene Encoding the HPP Oxidase from *Arthrobacter globiformis*

HPP oxidase (HPPO) converts HPP to 4-HPA via a decarboxylation reaction. This enzyme therefore catalyzes the first enzyme activity required to construct the metabolic pathway bypassing HPPD. HPP oxidase activity has been characterized in crude extracts of *Rhodococcus erythropolis* S1 (Suemori et al., 1995) or in a partially purified extract of *Arthrobacter globiformis* (Blakley, 1977). To our knowledge, the protein has not been purified. In order to be able to introduce this enzyme activity into the plant, it is necessary to identify the gene thereof. Various approaches can be envisaged: (1) insertional mutagenesis and therefore identification of the gene through the loss of the enzyme activity, (2) functional complementation of a microorganism using a genomic library, (3) purification of the protein in order to work back to the nucleic acid sequence.

The three approaches were used. The functional complementation and the insertional mutagenesis will be developed relatively little, since these techniques do not make it possible to identify the HPPO gene.

I.1 Materials and Methods

I.1.1—Culturing Conditions

I.1.1.1—Rich Media

Luria-Bertani (LB; sold by Bio101) medium is used to culture the bacteria (*E. coli, P. fluorescens*) in the molecular biology experiments. For culturing *A. globiformis* Columbia-ANC medium enriched with 5% of sheep blood (BioMérieux) will be preferred. This rich medium contains two antibiotics (nalidixic acid and colimycin) which inhibit Gram-negative microorganisms. Although the three bacteria grow on rich medium at 37.degree. C., *A. globiformis* and *P. fluorescens* are generally cultured at 29° C.

I.1.1.2—$M^{Ag}$ Culture Medium

The culture medium described by Blakley (1977) precipitates, and it is therefore necessary to filter it before use. We gradually changed the medium in order to achieve an optimal "minimal" medium. The factors considered are the growth rate of *A. globiformis* and the enzyme activity of HPPO. The medium selected ($M^{Ag}$) is an M9 medium (Maniatis et al., 1982) which is slightly modified: $Na_2HPO_4$, $12H_2O$ (6 g/L); $KH_2PO_4$ (3 g/L); $NH_4Cl$ (1 g/L); NaCl (0.5 g/L); $CaCl_2$ (6 mg/L); $FeSO_4$ $7H_2O$ (6 mg/L); yeast extract (20 mg/L); and, finally, the substrate (HPP or tyrosine or citrate) at a concentration of 1 g/L. The medium is autoclaved. Before use, 1 mL of sterile 1 M $MgSO_4$ is added per liter of medium.

This minimum medium is also used to culture *P. fluorescens*

I.1.2—Construction of an *Arthrobacter globiformis* Genomic Library

There is no reliable technique for making a complete bacterial cDNA library. We therefore decided to create an *Arthrobacter globiformis* genomic library. To produce this, we chose the cosmid system. The cosmid library was prepared for the functional complementation experiments and was then used later to search for the cosmid(s) containing the hppO gene.

I.1.2.1—The Cosmid Vector pLAFR5

I.1.2.1.1—Description of the Vector

We choose the conjugated cosmid vector pLAFR-5 (Keen et al., 1988) which can accept an insert of approximately 20 kb. Equipped with an origin of transfer and an origin of replication with a broad Gram-negative-host spectrum, it can be transmitted to other bacterial genera by tri-parenteral conjugation, which can be useful for testing functional complementation in various bacterial genera. It imparts resistance to tetracycline.

I.1.2.1.2—Preparation of the Vector

The plasmid pLAFR-5 is purified using an alkaline lysis protocol (Maniatis et al., 1982), treated with RNAse and then digested with Bam HI and Sca I. The digestion with Bam HI makes it possible to open the site into which the inserts of genomic DNA digested with Sau3A will be "ligated". The digestion with Sca I makes it possible to release the cos sites which allow the encapsidation. After extraction with phenol then chloroform, the DNA is precipitated with ethanol. The dry DNA is dissolved in water. The vector thus prepared is stored at −20° C.

I.1.2.1—Preparation of the *A. globiformis* Genomic DNA

A 24-hour culture (200 mL, 180 rpm, 29° C.) prepared in the medium (200 mL) described by Blakley (1977) is centrifuged at 3000 g at 4° C. for 15 minutes. The cell pellet, taken up with 10 mL of lysis solution (TE pH 8; 0.5% SDS; 1 mg proteinase K), is incubated at 37° C. in a waterbath with gentle agitation every 20 minutes. After 90 minutes, the suspension of lysed cells is poured into a polypropylene JA-20 tube. 10 mL of phenol/chloroform/isoamyl alcohol (25/24/1) are then added, followed by centrifugation at 6000 g for 15 minutes at 4° C. The supernatant is then transferred into a new JA20 tube, to which 1.8 mL of 10 M ammonium acetate and 10 mL of isopropanol are added. After centrifugation at 20 000 g for 20 minutes at 4° C., the pellet is rinsed with 70% ethanol. The dry pellet is taken up with 1 mL of TE, pH 8, and then transferred into a 2 mL Eppendorf tube to which 10 μl of RNAse (10 mg.mL$^{-1}$) are added. After 30 min at 37° C., 800 μL of phenol/chloroform/isoamyl alcohol are added. After centrifugation, the supernatant is transferred to a new Eppendorf tube and extracted with 0.8 mL of chloroform. The supernatant is then transferred into a final Eppendorf tube, to which 200 μL of 10 M ammonium acetate and 800 μL of isopropanol are added. After centrifugation, the pellet is rinsed with 70% ethanol and then, once dry, taken up in 500 μL of water. The genomic DNA is then stored at −20° C.

I.1.2.3—Controlled Digestion of the *A. globiformis* Genomic DNA

Only cosmids of 40-45 kb can be encapsidated. Since the vector is 21.5 kb, the inserts of *A. globiformis* genomic DNA should be between 19 and 22 kb in size. These fragments are obtained by performing a controlled digestion of the *Arthrobacter globiformis* genomic DNA. In order to define the optimal conditions for the controlled digestion, digestion of the *A. globiformis* genomic DNA are carried out with varying amounts of Sau 3A restriction enzyme. It appears that the best digestion condition uses 0.08 Sau 3A enzyme units for 30 minutes at 37° C. The genomic DNA thus digested is between 15 and 22 kb in size. The genomic DNA thus digested is extracted with phenol, then with chloroform and, finally, precipitated with ethanol.

I.1.2.4—Ligation of *A. globiformis* Genomic DNA into the Cosmid Vector

The ligation reaction is carried out in a final volume of 10 μL, containing 500 ng of pLAFR-5 digested with Bam HI and Sca I, 650 ng of genomic DNA digested with Sau 3A, 320 units of $T_4$ DNA ligase (N.E.B.) and 5 mM of ATP. The ligation takes place at 12° C. overnight (approximately 16 hours). The 5 mM of ATP makes it possible to avoid ligations between blunt ends (Sca I) (Feretti & Sgaramella, 1981) such that the dimers of vectors having no insert cannot become encapsidated in the head of the k phages.

I.1.2.5—Encapsidation of the Cosmids and Amplification of the Cosmid Library

The encapsidation of the cosmids, carried out using the GIGAPACK II XL kit (Stratagene) respecting the supplier's instructions, provides an efficiency of transfection greater than those obtained with conventional transformation techniques. To amplify the cosmid library, Keen et al. (1988) advise using *Escherichia coli* DH-1 and HB101. Specifically, when the strains are cultured on maltose, they produce a membrane-bound protein which enables better attachment of the phage and therefore more efficient transfection of the cosmids. The library, amplified according to Stratagene's recommendations, is stored at −80° C. To evaluate the cosmid library, the plasmid DNA isolated from about thirty clones is digested with Apa I or Eco RI. The restriction profiles are reserved on a 0.8% agarose gel.

I.1.3—Purification of the HPP Oxidase

I.1.3.1—Colorimetric Assay for the HPP Oxidase Activity

In order to be able to control the purification steps, the HPP oxidase activity is followed using the colorimetric assay described by Blakley (1977). The enzyme reaction is stopped by adding 2,4-dinitrophenylhydrazine (2,4-DNPH), in solution in 2 M HCl. The 2, 4-DNPH reacts with the ketone function in the alpha position of a carboxylic function (example: HPP). A hydrazone thus forms, which can be revealed by basifying the medium. When the HPP is completely converted to 4-HPA during the enzyme reaction, the hydrazone cannot form, and the characteristic yellow color of 2,4-DHPA is therefore obtained in basic medium. If the HPP is not completely converted to 4-HPA during the enzyme reaction, the formation of hydrazone is possible. These hydrazones are brown in color in basic medium. A variation in color between these two extremes is obtained as a function of the amount of HPP consumed. The absorption measurements are carried out at 445 or 450 nm. In order to make this assay more easy to handle, we adapted it to the 96-well microplate format. The reaction mixture comprises GSH (900 μM); HPP (135 μM); TPP (1.8 mM); $MgCl_2$ (4.5 mM); FAD (4 μM); potassium phosphate buffer (90 mM) pH 7.4. The mixture is kept on ice. 50 μL of the test fraction and 150 μL of reaction mixture are placed in each well. After 20 min at 30° C., the enzyme reaction is stopped with 13 μL of 2,4-DNPH solution (0.1% in 2 M HCl). The mixture is left to react for 20 min at ambient temperature. The formation of hydrazone is revealed by adding 13 μL of 10 M NaOH solution. To prepare the standard range, reaction mixtures with varying concentrations of HPP are prepared. The 50 μL protein fractions are replaced with 50 μL of protein extraction buffer. The standard curve is produced for each new solution of 2,4-DNPH (the 2,4-DNPH solution is stable for 6 months in the dark). The advantage of this assay is its rapidity and simplicity, but it has the defect of measuring the disappearance of substrate and not the appearance of product. In addition, the possibility of having false positives exists: a tyrosine amino transferase activity will give the same result as the, HPPO activity. Specifically, in both cases, the ketone function has disappeared. We therefore developed a rapid and sensitive HPLC method which makes it possible to confirm the production of 4-HPA.

I.1.3.2—Activity Assay Analyzed by HPLC

An HPLC method was developed using a small Spherisorb ODS2 column, 50×4.6 mm and particle size 3 μm. The chromatography is carried out under isocratic conditions A: 90%; B: 10% (where buffer A: $H_2O$, 0.1% TFA and buffer B: acetonitrile), flow rate 0.8 $mL.min^{-1}$ and the elution is followed at 230 nm. Under these conditions, it is possible to separate the 4-HPA, HGA, 3,4-DHPA and HPP in 5 minutes after injection. The column was custom made by Merck.

I.1.3.3—Purification of the Protein

The interests of simplicity were sought during the setting up of this protocol.

I.1.3.3.1—Preliminary Assays

The aim of the preliminary assays is to determine the influence of compounds (NaCl, KCl, 1-propanol, ethylene glycol, etc.) and of the pH on the enzyme activity. The reactions are carried out with crude extracts of *A. globiformis* cultured on $M^{Ag}$ medium containing tyrosine as the only carbon source ($M^{Ag}$-tyrosine). The test compound is added to the reaction medium. To measure the influence of pH on the enzyme activity of HPPO, various phosphate buffers are prepared.

I.1.3.3.2—Purification Protocol

The *Arthrobacter globiformis* strain is plated out on LB agar medium or on Columbia-ANC agar medium. After culturing for 16 hours at 29° C., a colony is removed and seeded in 5 mL of LB medium, under growth conditions for 8 hours at 29° C., 180 rpm. 50 μL of this preculture are then inoculated into 1.5 L of $M^{Ag}$-tyrosine or $M^{Ag}$-HPP medium, and the culturing is then carried out at 29° C., 180 rpm in Erlenmeyer flasks with thin rods (Belco). After culturing for 48 hours, the cells are collected by centrifugation at 5000 g for 15 minutes at 4° C. The cells are then resuspended in 50 mM Tris-HCl buffer, pH 7.4, and then centrifuged as previously. The pellet is taken up in 2 mL of 50 mM Tris-HCl buffer, pH 7.4. The cells are sonicated (Vibra Cell, Sonic Materials INC., Connecticut, USA) for 15 minutes, power 4, 30% pulse, in melting ice. The insoluble debris are eliminated by centrifugation for 25 min at 20 000 g, 4° C. The supernatant is recovered; it constitutes the "crude extract". It can be frozen in liquid nitrogen and then stored at −80° C. (for 6 months without apparent loss of activity). The crude extract is loaded, without prior desalting, onto an "EMD/DEAE 650 S" weak anion exchange column (Merck) equilibrated in 50 mM phosphate buffer, pH 7.4. Elution of the enzyme activity is obtained by applying an NaCl concentration gradient (in solution in a 50 mM phosphate buffer, pH 7.4). The fractions containing the enzyme activity are pooled. The protein solution obtained is diluted 2.7-fold with 50 mM phosphate buffer, pH 7.4. The proteins are then loaded onto a "source Q" strong anion exchange column (XK16, Pharmacia) (30 mL, Pharmacia) pre-equilibrated with a 50 mM phosphate buffer, pH 7.4. The protein fractions of value, identified by the enzyme activity, are pooled and then concentrated through UVIKON 10 kDa membrane. The resulting protein extract is then desalted by the gel filtration technique using a "PD10" column (Pharmacia) equilibrated in 10 mM phosphate buffer pH 7.4, and eluted with this same buffer. The proteins are then loaded onto a hydroxyapatite column (XK9/15, Pharmacia) (2 mL; hydroxyapatite DNA grade Bio-Gel® HTP gel; Bio-Rad) equilibrated with 10 mM phosphate buffer, pH 7.4. The enzyme activity is eluted by applying a phosphate gradient. The fractions containing the enzyme activity are pooled and concentrated. The active proteins are conserved when the protein concentration is greater than 1 mg/mL by adding FAD, GSH and glycerol in order to obtain the following final concentrations: 27 μM FAD, 110 μM GSH, 0.8% glycerol. The proteins thus prepared can be frozen at −80° C. for at least 6 months.

I.1.3.3.3—Assaying of Proteins

The proteins are assayed according to the Bradford method (1976) using γ-globulin for the standard.

I.1.3.3.4—Staining of Protein Gels

The protein fractions are analyzed on 10% polyacrylamide gel according to the Laemmli method (1970). After migration, the proteins in the gel are stained either using the Coomassie Blue method (Chua, 1980) or using the silver nitrate method (Schoenle et al., 1984).

I.1.4—Protein Microsequencing of the N-Terminal End and of Internal Peptides

The microsequencing of the protein is carried out using the Edman method (Laursen, 1971). To obtain the best results in the sequencing, the gel is prepared on the same day.

I.1.4.1—Preparation of the Acrylamide Gel and Electrophoresis Thereof.

The gels (8.5%, 10% or 12%) are prepared according to the Laemmli method (1970) using the Hoefer® minigel system. The proteins are diluted to one third with a "denaturing loading blue" solution (150 mM Tris-HCl, pH 6.8; 4% SDS; 2% (v/v) β-mercaptoethanol; 3.3% (v/v) glycerol; 0.03% bromophenol blue; qs 10 mL of milliQ water). After having been boiled for 5 minutes, the proteins are loaded onto the acrylamide gel. The migration is carried out at ambient temperature using a denaturing migration buffer (25 mM Tris base; 250 mM glycine; 0.014% (v/v) β-mercaptoethanol; 0.1% SDS) and applying a strength of 15 mA per gel.

I.1.4.2—Preparations for the Sequencing of the N-Terminal End

In order to be able to carry out the sequencing of the N-terminal end, the gel is transferred onto a PVDF membrane (PROBLOTT®—Applied Biosystems) using the semi-dry transfer technique. The electrotransfer of the polypeptides is carried out in 30 minutes at 300 mA with the "Semy Dry Electroblotter" device (Bio-Rad) and in a CAPS-based medium (transfer buffer: 10 mM CAPS, pH 11.0; 10% (v/v) methanol). The transfer buffer contains no glycine which would risk "polluting" the sequencing. After the transfer, the membrane is rinsed for a few seconds with milliQ water. It is then immersed for a few seconds in a staining solution based on amido-black (Aldrich; ref.: 19.524-3). The solution consists of 45% (v/v) methanol, 1% (v/v)-acetic acid, 0.1% (m/v) amido-black and 63.9% (v/v) water. When the band corresponding to the protein of interest is visible, the membrane is thoroughly rinsed with milliQ water and is then air-dried. The part of the membrane containing the protein of interest (60 kDa) is cut out and sent for sequencing.

I.1.4.3—Preparations in View of Sequencing the Internal Peptides

In order to visualize the proteins in the gel, an amido-black staining protocol is used which is slightly different from that used to stain the PVDF membrane. After migration, the gel is fixed for two times thirty minutes with a solution consisting of 50% methanol, 10% acetic acid, 40% milliQ water. The staining is carried out with a solution containing 45% methanol, 10% acetic acid, 45% water and 0.003% (w/v) amido-black. The proteins appear gradually. When the staining is sufficient to locate the protein, the gel is thoroughly rinsed with milliQ water. The band of interest is cut out and then dehydrated in a speed-vac (Savant). The gel band, having lost approximately a third of its length, is sent for sequencing. The internal peptides are obtained after digestion with the protein with Lys-C endoprotease (sequencing grade, Boehringer). The protein in the polyacrylamide gel is digested in 150 μL of Tris-HCl buffer, pH 8.6 (0.1 M), containing 0.03% of SDS, at 35° C. for 18 hours in the presence of 0.4 μg of Lys-C endoprotease. The digested protein is injected onto a DEAE-C18 HPLC column (diameter 1 mm); the peptides are eluted using a gradient of acetonitrile (from 2 to 75%) containing 0.1% TFA. The Lys-C endoprotease specifically cleaves the polypeptides on the carboxylic side of the lysines.

I.1.5.1—Theoretical Validation Using the *Arthrobacter globiformis* MndD Gene

A portion (867 bp) of the MndD gene is amplified by PCR using the primers "OZ-MndD-S711": ACGTCACCGA AGAGGATGAA AAC (SEQ ID NO: 23) and "OZ-MndD-AS1578": ACGGCCATTT CGGACTTTTC (SEQ ID NO: 24). The PCR is carried out using the following program: 95° C. 5 min; 25 cycles: 95° C. 45 sec, 56° C. 45 sec; 72° C. 1 min; 72° C. 5 min; 4° C. on hold. The reaction mixture comprises 200 to 500 μL of dNTP, 20 to 200 ng of cosmid or genomic DNA and 100 pmol of each primer in a final volume of 50 μL.

I.1.5.2—Identification by PCR of a Portion of the Gene Encoding the HPP Oxidase

The PCR is carried out using the "Advantage®-GC-Genomic PCR" kit, (Clontech). This kit comprises, inter alia, a "GC melt" betaine-based adjuvant and a mixture of thermoresistant polymerases—mainly with *Thermus thermophilus* (Tth)-. The amplification is carried out on the *Arthrobacter globiformis* genomic DNA, using the following program: 94° C. 5 min; 30 cycles: 94° C. 20 sec, 60° C. 30 sec, 72° C. 3 min; 72° C. 6 min; 4° C. on hold. The reaction conditions are 400 μM of dNTP, 50 ng of genomic DNA, 100 pmol of each primer and 1× "GC melt", for a reaction volume of 50 μL. Under these conditions, we amplify a band of 937 bp which we refer to as Z2.

The PCR amplification can also be carried out using Epicentre Tth or Tbr (*Thermus brockianus*—Finnzyme). Tbr is the only thermoresistant polymerase tested to be able to carry out the PCR without additives (DMSO, glycerol, betaine); it is also a high-fidelity enzyme.

I.1.6—Screening of the Cosmid Library

The cosmid library is screened using the digoxigenin-labeled cold probe technique (Boehringer Mannheim, 1995).

I.1.6.1—Preparation of the Z2-Dig Probe

The probe is labeled with digoxigenin by PCR in a final volume of 50 μL, under the conditions defined in paragraph II.5.2, except for the mixture of dNTP consisting of: 90 μM dUTP-Dig; 135 μM dTTP; 225 μM dATP; 225 μM dCTP; 225 μM dGTP. The amplified probe is quantified by loading 3 μL of the reaction onto a 0.8% agarose gel. A slight background noise appears, i.e. the PCR is not sufficiently specific. In order to avoid all subsequent problems, the entire PCR is loaded onto a gel and the band of interest is extracted using the Qiaex II kit (Qiagen).

I.1.6.2—Transfer of the Cosmid Library onto Hybond N Membrane

The glycerol stock of the cosmid library prepared in *E. coli* HB101 is used to inoculate 2 mL of $LBT^{15}$ medium. After growth for 8 hours, the $OD_{600}$ is estimated; sera dilutions are prepared in order to plate out approximately 1000 clones per dish (144 $cm^2$). After growth for 16 hours at 37° C., the bacteria are transferred to Hybond N membranes (Amersham) and lysed according to Boehringer Mannheim's recommendations (1995). The DNA released is fixed to the membrane by exposure to U.V. (120 mJ delivered in 45 sec—Stratalinker; Stratagene). The cell debris are removed from the membranes by carrying out the proteinase K treatment as recommended by Boehringer Mannheim (1995).

I.1.6.3—Prehybridization—Hybridization—Detection

The steps of prehybridization and hybridization are carried out in a bag placed on a rocking platform, using the technique of hybridization with the digoxigenin-labeled probe (Boehringer Mannheim, 1995). The prehybridization (5×SSC; 0.5% SDS; 0.1% N-laurylsarcosine; 1% blocking agents (Boehringer Mannheim, ref.: 1096 176); 100 $\mu g.mL^{-1}$ sonicated and denatured salmon sperm) is carried out for 0.4 hours at 65° C. Hybridization of the membrane is carried out overnight at 68° C. (fresh prehybridization medium containing 20 $ng.mL^{-1}$ of digoxigenin-labeled probe denatured for 5 min at 100° C.). The following day, the excess probe and the aspecific hybridizations are removed with four washes with buffer A (0.5×SSC; 0.1% SDS, 65° C.). The membranes are then equilibrated for 5 min at ambient temperature in buffer B (138 mM malic acid, 142 mM NaCl, adjusted to pH 7.5 with sodium hydroxide pellets, 0.3% tween 20). They are then saturated with blocking agents (Boehringer Mannheim) for 30 minutes, before being hybridized with the alkaline phosphatase-coupled anti-digoxigenin antibody ("anti-digoxigenin-AP, Fab fragments"; Boehringer Mannheim) diluted to {fraction (1/10000)} in a fresh solution of blocking agents. After 30 minutes the membranes are rinsed for two times 15 minutes in buffer B, and then equilibrated for 5 minutes in the alkaline phosphatase reaction buffer (0.1 M Tris; 0.1 M NaCl; 0.05 M $MgCl_2$, pH 9.5). The membranes are covered with 1 ml of ready-to-use CSPD and are then incubated for 15 min at 37° C. This step at 37° C. allows rapid activation of the alkaline phosphatase coupled to the antibody. The membranes are developed by exposing Hyperfilm® ECL (Amersham) for 1 to 15 minutes.

I.1.6.4—Analysis of the Positive Cosmids by Southern and PCR

The cosmids identified in the hybridization on membrane are confirmed by PCR and by the Southern technique. In this case, the cosmid DNA, purified by alkaline lysis (Maniatis et al., 1982), is digested with restriction enzymes and then separated on a 0.8% agarose gel. The gels are transferred onto Hybond $N^+$ membrane (Amersham) by the Southern technique in 20×SSC (Ausubel et al., 1995). After transfer, the membrane is rinsed with 2×SSC and the DNA is then fixed to the membrane using U.V. (120 mJ delivered in 45 sec-Stratalinker; Stratagene). The membrane is then developed using the cold probe technique previously described.

I.1.7—Cloning Vectors and Host Bacteria

The PCR-amplified DNA sequences are generally cloned into the plasmid p-GEMT-easy (Promega), which allows screening using the "blue-white" technique. For overexpression, the plasmid pKK223-3 (Pharmacia) is used, which places the gene under the control of a tac promoter. The clonings are generally carried out using *E. coli* DH5α (New England Biolabs) or *E. coli* XL1 Blue (Stratagene). For overexpression, *E. coli* BL21 (DE3) will be preferred.

I.1.8—Enzyme Activity of Acetolactate Synthase (ALS)

The acetolactate synthase (ALS) activity is measured using the clorimetric method described by Chang and Duggleby (1997). The reactions are carried out in microplates with a total volume of 250 μL. For each reaction, 25 μL of enzyme are incubated for 30 min at 37° C. in 225 μL of reaction medium consisting of 50 mM KPi, pH 7.0; 50 mM sodium pyruvate; 1 mM TPP; 10 mM $MgCl_2$; 10 μM FAD. The reaction is stopped by adding 25 μL of 10% $H_2SO_4$. The microplates are then incubated at 60° C. for 15 min. 250 μL of 0.5% creatine and 250 μL of 5% α-naphthol in 4M NaOH (the α-naphthol solution should be prepared less than 10 min before use) are then added. The microplate is then incubated for 15 minutes at 60° C. and then 15 minutes at ambient temperature. A cherry red color appears. The reading is carried out at 525 nm ($\epsilon_m$=22 700 $M^{-1}$ $cm^{-1}$).

I.2—Results—Discussion

HPP oxidase is the first enzyme activity which we wish to introduce into the plant in the context of creating the metabolic pathway bypassing HPPD. In order to be able to identify the gene encoding the HPP oxidase activity, various approaches were developed: (1) insertional mutagenesis and therefore identification of the gene through the loss of the enzyme activity, (2) functional complementation of a microorganism using a genomic library, (3) purification of the protein in order to work back to the nucleic acid sequence. It is the third approach which was preferred.

I.2.1—Purification of the HPPO

I.2.1.1—Optimization of the Culture Conditions

Before beginning to purify the protein, it is useful to determine which culture conditions allow its expression in the bacterium. The results of optimization of the culture conditions show that the HPP oxidase activity is not detectable when the growth of *A. globiformis* depends on a carbon source such as succinate, fumarate or glucose. On the other hand, the HPP oxidase activity is detected when *A. globiformis* is cultured using HPP, tyrosine or phenylalanine as the only carbon source. If the amount of yeast extract is increased (for example 200 $mg.L^{-1}$ instead of 20 $mg.L^{-1}$), a decrease in the enzyme activity produced is observed. The $M^{Ag}$ medium is defined on the basis of these observations. Finally, it is observed that a high-density culture (at the beginning of the stationary phase; $OD_{600}$~1) exhibits a weaker HPP oxidase enzyme activity than in the case of a culture in the exponential growth phase ($OD_{600}$~0.4).

I.2.1.2—Preliminary Assays

We have just defined the optimal medium for the production of the HPPO, we now search for the conditions which do not impair the stability of the HPP oxidase during the purification processes. For the chromatographies involving anion exchange resins and the chromatographies as a function of pH, it is important to know the sensitivity of the enzyme to pH and to salts. We observe that the optimum pH is between pH 7.0 and 7.8, as has been demonstrated by Blakley (1977). The enzyme appears to be relatively insensitive to salts (NaCl and KCl) since concentrations of greater than 750 mM are necessary to observe a decrease in enzyme activity. We now know the conditions for good expression of the enzyme activity and we have determined the sensitivity of the HPP oxidase activity to factors possibly intervening during the purification. The purification of the HPPO can therefore begin.

I.2.2.3—Purification of the HPPO

To purify the HPPO, the protocol described above is applied. The enzyme activity is eluted from the DEAE EMD 650S with 150 to 200 mM of NaCl in solution in a 50 mM phosphate buffer, pH 7.4. The fractions containing the enzyme activity are pooled and conserved overnight at 4° C. Freezing at this step in fact leads to a loss of activity. The proteins are then loaded onto a Source Q resin. The enzyme activity is then eluted with an NaCl concentration of between 150 and 0.200 mM in solution in a 50 mM phosphate buffer, pH 7.4. The fractions containing the enzyme activity are pooled and then concentrated on UVIKON 10 kDa membrane, and stored at 4° C. overnight. Finally, the HPPO is purified in a third step by applying a phosphate gradient to a hydroxyapatite column. The activity is eluted with a concentration of phosphate in the region of 30 mM. The fractions containing the HPP oxidase enzyme activity, at the hydroxyapatite column outlet, are then analyzed on an SDS-8.5% PAGE gel stained with silver nitrate. The gel exhibits the development of two protein bands. By comparison between the enzyme activity profile and the protein elution profile, we consider that the HPPO corresponds to the high molecular protein (approximately 60 kDa). In the attempt presented, the purification is initiated with 1.5 g of soluble proteins extracted from *A. globiformis*, and we recovered 150 μg of a mixture of proteins (including approximately 70 μg of HPPO). The purification factor in terms of specific activity was not determined. As a result, we used total reaction conditions to follow the elution of the enzyme activity. In addition, the problem was more the identification of the protein than the development of a purification protocol. The HPLC analysis, of the reactions carried out at the end of each purification step, shows the appearance of a product which has the same retention time as the 4-HPA standard (SIGMA). Forty picomoles of the HPPO protein (60 kDa) are transferred onto a PVDF membrane and are sent for sequencing at the same time as 40 pmol of the protein included in the acrylamide gel. The proteins transferred onto membranes serve to determine the N-terminal sequence, whereas the proteins included in the gel are used to determine the sequence of internal peptides.

I.2.2.4—Results of Sequencing the HPPO

Few internal peptides are obtained on exiting HPLC, after digestion of the HPPO with Lys-C endoprotease. This result suggests that the protein contains little lysine; specifically, Lys-C endopeptidase cleaves after lysines. If lysine is relatively infrequent, digestion with endopeptidase K generates long peptide fragments which remain adsorbed in the column and cannot be eluted, even using very hydrophobic conditions. Based on the shape of the chromatographic peaks and also on the apparent amount, three peptides were selected and then sequenced. They are named as a function of their order of leaving the HPLC column: peptide No. 4, peptide No. 6, peptide No. 11. Their sequence is respectively: (A)WWAEALK (SEQ ID NO: 25), AAAGRILRLL DDAAGANASK (SEQ ID NO: 26), XDNRFTAVDF XT (where X is an undetermined amino acid) (SEQ ID NO: 27). The sequence of the first 30 N-terminal amino acids is obtained with an initial yield of 40%: TSLTVSGRVA QVLSSYVSD VFGVMGNGNV Y (SEQ ID NO: 28). The amino acid (methionine or valine) corresponding to the initiation codon (ATG or GTG) is not found. The initial yield obtained (15 pmol BSA equivalent), compared with that obtained for the internal peptides (30 to 35 pmol BSA equivalent), suggests that some of the proteins were blocked at the N-terminal. The N-terminal sequence and the internal sequences obtained show no homology in the databases. Based on the peptide sequences obtained, degenerate oligonucleotides are synthesized in order to identify the HPPO gene by PCR.

I.2.3—Validation of the PCR Techniques and Identification of a Portion of the hppO Gene I.2.3.1—Validation of the PCR Techniques The content of guanine and cytosine base (SC %) of the majority of *Arthrobacter* sp. genomic DNAs is between 59 and 66%; however, it is 67 to 69% for *A. agilis* (formerly *Micrococcus agilis*) (Koch et al., 1995), 70% for *A. atrocyaneus* (Jones et al., 1991) and 73% for an *Arthrobacter* sp. identified in arctic ices (Junge et al., 1998). These high contents of guanine and cytosine can make it more difficult to carry out PCR. For this reason, we validated our PCR methods (genomic DNA, polymerases, etc) using the gene encoding *Arthrobacter globiformis* "Manganese dependent Dioxigenase" (MndD) (Boldt et al., 1995). This enzyme of the HPP degradation pathway catalyzes the opening of the aromatic ring of 3,4-dihydroxyphenyl acetate. For the control amplification of the MndD gene, we tested *thermophilus aquaticus* (Taq) thermoresistant polymerases marketed by various suppliers (Perkin Elmer, ATGC, Appligne, Qiagen, Sigma). In all cases, amplification of the MndD gene is obtained. However, under equivalent conditions, using the degenerate primers encoding the HPPO peptides, amplification of the hppO gene is not obtained even using additives (DMSO, glycerol).

I.2.3.2—Identification by PCR of the N-Terminal Portion of the hppO Gene

We specifically amplified a 936 bp DNA sequence which might correspond to the N-terminal portion of the hppO gene. The amplification was obtained using, firstly, the degenerate primers Ox3: TTNGCNCCNG CNGCRTCRTC (SEQ ID NO: 29) and OZ10N: GAYGTNTTYG GNGTNATGGG NAAYGG (SEQ ID NO: 30) corresponding, respectively, to a portion of peptide No. 6 and to a portion of the N-terminal peptide sequence and, secondly, the "Advantage GC Genomic PCR" kit (Clontech). The Clontech kit is designed to carry out PCRs on GC-base-rich genomes. It contains a mixture of thermoresistant polymerases (including Tth) and a betaine-based additive. Tth is a thermoresistant polymerase purified from *Thermus thermophilus*. The degeneracy of each primer is 1024, i.e. one primer out of 1024 exhibits the exact nucleic acid sequence of the gene being sought. The degeneracy originates from the fact that an amino acid can be encoded by several codons; for example, alanine is encoded by four codons (GCA, GCC, GCG, CGT). The degeneracy code used for the primers is defined as follows: N=A or T or G or C; R=A or G; Y=T or C. The theoretical hybridization temperatures are, respectively, 55.4° C. and 57.6° C. Despite a hybridization temperature of 60° C. used in the PCR, the OX3 primer alone allows nonspecific amplifications. We specifically amplified, by PCR, a 936 bp DNA fragment, using two degenerate primers. We must be sure that this amplified DNA corresponds correctly to the hppO gene being sought.

I.2.4—Characteristic of the 936 bp DNA Fragment

The 936 bp DNA fragment amplified by PCR is purified on agarose gel. It is then cloned into pGEM-T easy, according to the supplier's instructions, and then sequenced. When the nucleic acid sequence obtained is translated, it is observed that it encodes, at the two ends, for the entire peptide No. 6 and for a large part of the N-terminal sequence. We are therefore sure to have amplified a portion of the gene encoding the purified and microsequenced protein, the HPPO. The nucleic acid sequence contains 73% of guanine (G) and cytosine (C) bases; the possible formation of secondary "stem-loop" structures is also noted in the first 250 bases of the messenger RNA. This high content of G and C bases and also the existence of the secondary structures may partly explain the difficulties encountered in achieving the PCR amplification of part of this gene. The 936 bp nucleic acid sequence and also the corresponding protein sequence exhibit no homologies with the sequences recorded in the databases. We now have a 936 bp sequence oriented from the N-terminal toward internal peptide No. 6. Since the protein is approximately 60 kDa, a gene of approximately 1650 bp is sought. There remains therefore approximately 700 bp to be identified. For this, we will screen the *A. globiformis* genomic library produced in the cosmid pLAFR5 and amplified in *E. coli* HB101.

I.2.5—Screening of the *A. globiformis* Cosmid Library

The genomic library prepared is transferred onto membranes and is then screened using, as probe, the 936 bp DNA fragment labeled with digoxigenin. The standard protocol is adapted for a "conventional" DNA (60% AT), while the 936 bp fragment exhibits an estimated proportion of 23% AT. If we keep the same dUTP-Dig/dTTP ratio as in the case of a conventional DNA, we obtain a weakly labeled probe and therefore a less sensitive detection. We therefore optimize the dUTP-Dig/dTTP proportion necessary for labeling the probe (paragraph II.7.1). Screening of the genomic library made it possible to identify four cosmids (Cos1A, Cos2A, Cos4A, Cos17A1) having different restriction profiles. By comparing the results of Southern hybridization obtained using the cosmids with those obtained using the *Arthrobacter globiformis* genomic DNA, we selected the cosmid 2A. FIG. No. 14 illustrates the approach used taking as an example digestion of the cosmids with the Not I restriction enzyme. It is observed first of all that the cosmid vector pLAFR5, digested with Not I, does not hybridize with the Z2-Dig probe. On the other hand, it is observed that the cosmid 1A exhibits a single hybridization band at 2.3 kb while, the cosmids 2A, 4A and 17A exhibit two hybridization bands at 4.3 and 2.3 kb. Now, digestion of the *A. globiformis* genome with Not I produces two bands of 4.3 and 2.3 kb; as a result, we consider that the cosmid 1A does not contain all the information sought. Based on other restrictions and using an equivalent approach, the cosmids 4A and 17A, are eliminated. The cosmid 2A is then sequenced over a distance of approximately 3 kb on either side of the Not I site identified in the middle of the Z2-Dig probe. The results of hybridization of the genomic DNA also show that the gene is present in a single copy. We have identified the cosmid 2A which we have sequenced over 6.2 kb. We will now be able to analyze this DNA sequence derived from the *Arthrobacter globiformis* genome.

I.2.6—Overall Analysis of the 6.2 kb of *Arthrobacter globiformis* Genomic DNA

Using Vector Nti software, the position of the potential genes is defined from the nucleic acid sequence of 6255 bp obtained by sequencing the cosmid 2A. The 936 bp sequence, identified by PCR, is found to be part of a potential gene. This potential gene therefore probably corresponds to the hppO gene. Four other genes (A, B, C, D) are potentially identified (FIG. 3) by carrying out a search by homology using the BLASTX algorithm. Gene A will encode an amino acid transporter, Gene B will encode a histidinol-phosphate amino transferase; however, previous studies show that this enzyme has tyrosine amino transferase activity in the Gram-positive bacterium *Bacillus subtilis* (Nester & Montoya, 1976) gene C will encode a transcription regulator, while gene D will encode an operon regulator.

I.2.7—Analysis of the hppO Gene

I.2.7.1—General Description

Over the 6256 bp sequence obtained, the hppO gene (in green) is delimited in 5' by the ATG initiation codon at position 3143 and in 3' by the stop codon TAG (in red) at position 4823. The gene therefore has a real length of 1680 bp. It exhibits a high content of G and C bases (71.4%, GC). The search for homologies in the nucleic acid sequences (BLASTN) gives no identification. In order to more thoroughly characterize the gene, the specific elements of transcription and of translation are sought.

I.2.7.2—Elements Characterizing the Transcription and Translation of the hppO Gene The potential transcription promoter boxes are identified (FIG. 4). Box "−10", termed "Pribnow box" is located between 3082 to 3088 (AAAAATA) and box "−35" is located at position 3055 to 3059 (TTGCA). These boxes thus defined are slightly different from the canonic sequences (respectively TATAAT and TTGACA; Singer & Berg, 1992). This may reflect a weak interaction with the factors allowing constitutive transcription or else the necessary interaction with different transcription factors. The adenine at position 3096 might be the transcription initiation base. Finally, a sequence corresponding to the binding site for the CAP protein (catabolic gene activator protein) is identified between positions 3068 to 3072 (TGTGA). Finding this CAP protein-binding site is in agreement with the results obtained in the optimization of the culture conditions. In conclusion, the transcription of the hppO gene is probably under the control of a weak promoter, in particular regulated by glucose. The Shine-Dalgarno sequence (Singer & Berg, 1992) allows binding of the ribosomal small subunit. It is identified (GACGAT; at positions 3131 to 3136) 12 bases upstream of the translation initiation codon (ATG), by analogy with the AGGA consensus sequence. It is also observed that the 5' terminal portion (approximately 250 bases) of the messenger RNA is capable of forming a stem-loop structure. Now, the secondary structure of the region of the mRNA which is in the region of the initiator ATG influences the translation initiation step. Thus, the initiation is zero or relatively inefficient when the initiator ATG or the Shine-Dalgarno sequence is involved in intramolecular pairing. The question may therefore be posed of whether the step-loop structures observed have a possible role in regulating the translation.

I.1.2.7.3—Expression of the HPPO Under the Control of the tac Promoter

Overexpression of the HPPO is advantageous for defining the kinetic characteristics, to allow the production of antibodies, but also for the purpose of structural analysis. The gene is cloned into a vector pKK223-3 in two stages. The gene, amplified by PCR under the conditions defined for the identification of the hppO gene and using the primers HPP-N-sense (CATGACTTCA CTTACAGTGT CC) (SEQ ID NO: 31) and HPP-C-term (CAAACTGAGT AGCAGCTCAG G) (SEQ ID NO: 32), is cloned into the vector pGEMT-easy. The clone exhibiting the hppO gene in the antisense direction with respect to the lac promoter is selected. It is then digested with Eco RI. By doing this, the hppO gene is recovered, and is inserted into the vector pKK223-3 digested with Eco RI. The clone pKK3-2, exhibiting the hppO gene under the control of the tac promoter is selected. When the expression of the clone pKK3-2 is induced by adding IPTG, HPP oxidase activity can be detected. However, the overexpressed protein (57.4 kDa) cannot be detected in a crude extract separated on denaturing acrylamide gel. The overexpression protocol therefore remains to be improved. We also envision cloning the HPPO as a fusion with a Tag sequence (GST, polyhistidine, protein A, etc) in order to facilitate purification of the overexpressed protein. We have just definitively shown that the identified gene encodes an HPP oxidase activity. However, in carrying out homology searches at the protein sequence level (BLASTX or BLASTP), it is observed that the HPPO protein exhibits up to 25% identity with acetolactate synthases (ALSs), pyruvate oxidases (POXs) and pyruvate dehydrogenases (PDHs). It is thus possible to identify very conserved motifs such as those regarding TPP cofactor binding (FIG. 5). In addition, the hydrophobicity profile of the HPPO is very close to that obtained for ALSs (not shown). In order to be sure that the identified gene really encodes the HPPO and not an ALS, a POX or a PDH having a secondary activity of the HPP oxidase type, we decided to test the HPPO for a possible secondary activity.

I.2.8 HPPO Versus ALS

The protein homology searches show that HPPO exhibits up to 25% identity with ALSs. This result, although initially surprising, has a certain logic. Specifically, these two enzymes use FAD and TPP as reaction cofactors. They both carry out a decarboxylation. Moreover, one of the substrates of ALS is pyruvate; now, our substrate is a β-substituted pyruvate: hydroxyphenyl pyruvate. It is therefore possible that the structure of the active site is close and that, consequently, these proteins share common enzyme activities. We used the recombinant large subunit and purified ALSs from *Arabidopsis thaliana* (Chang & Duggleby, 1997) and from *E. coli* (Hill & Duggleby, 1998) to serve as a positive control in our experiments carried out in order to search for ALS activity in the HPPO. The results obtained show that the HPPO does not exhibit any ALS activity. We show on this occasion that the two ALSs tested have no HPP oxidase activity. Finally, we observe that the HPPO is not inhibited by 115 ppm of imazapyr (ALS inhibitor, cyanamid). These results clearly show that, despite common points (protein sequence and hydrophobicity), ALSs and the HPPO are clearly different enzymes which do not have secondary enzyme activities.

Example 2

Identification of the Genes Encoding 4-HPA 1-hydroxylase

4-HPA 1-hydroxylase (HPAH) converts 4-HPA to HGA via a hydroxylation reaction accompanied by displacement of the acetyl chain. Its activity has been characterized on crude extracts of *Rhodococcus erythropolis* S1 (Suembri et al., 1995) or on partially purified extracts of *P. acidovorans* (Hareland, 1975). It was purified by Suemori et al. (1996), but the protein and gene sequences are not published. In order to be able to introduce this enzyme activity into the plant, it is necessary to identify the gene.

Various approaches can be envisioned: (1) phenotypic and/or functional complementation using a genomic library, (2) insertional mutation and therefore identification of the gene through the loss of the enzyme activity, (3) purification of the protein in order to work back to the nucleic acid sequence. We chose to develop these three approaches with *Pseudomonas acidovorans* because there are many molecular biology tools whose effectiveness has been demonstrated on various species and strains of *Pseudomonas*. By way of examples, mention may be made of the mini-Tn5 transposon (De Lorenzo et al., 1990), the broad host spectrum vectors such as pBBR1MCS (Kovach et al., 1994, 1995; D'Souza et al., 2000), and the techniques for transfer by conjugation. The mini-Tn5 transposon can be used either to disturb a gene (de Lorenzo et al., 1990; Fedi et al., 1996; Campos-Garcia et al., 2000) or to introduce a gene into the bacterial genome (Prieto et al., 1999). We began with the approach by phenotypic, complementation because this appeared to be the most rapid and the most simple. This approach was followed by the two other simultaneously. However, we will not tackle the approach by insertional mutagenesis here since this approach was not subsequently exploited.

II.1—Materials and Methods

II.1.1—Construction of a *P. acidovorans* Genomic Library in *E. coli*

To construct the library we used the cosmid pLAFR5 and the genomic DNA of *P. acidovorans*. We used the host strain *E. coli* HB101.

II.1.2—Purification of the 4-HPA 1-hydroxylase

II.1.2.1—Spectrophotometric Activity Assay

In the reaction catalyzed by 4-HPA 1-hydroxylase, described by Hareland et al. (1975), molecular oxygen and NADH,$H^+$ are consumed. We chose to measure the enzyme activity by following the oxidation of NADH,$H^+$ to $NAD^+$. The reaction medium comprises: 300 μM NADH,$H^+$; 6.7 μM FAD; 100 mM KPi; 1 mM DDT; 10 to 50 μg of proteins. The reaction is triggered by adding the substrate: 1 mM 4-HPA. The reaction is followed at 340 nm or at 292 nm, for 2 to 10 min. Specifically, the consumption of NADH,$H^+$ results in a decrease in absorbance at 340 nm, while the production of homogentisate results in an increase in absorbance at 292 nm. The spectrophotometric assay is very rapid, it is used routinely to follow protein elution in purification steps.

II.1.2.1—HPLC Activity Assay

Analysis of the enzyme reactions by HPLC makes it possible to confirm the production of HGA (retention time, UV spectrum). The enzyme assay is carried out under the same conditions as above. However, the reaction is stopped by adding a third of a volume of 20% perchloric acid. The reactions are then analyzed by HPLC using isocratic elution with 90% of phase A and 10% of phase B or 92% of phase A and 8% of phase B. Phase A is milliQ water containing 0.1% of trifluoroacetic acid (TFA) and phase B corresponds to acetonitrile. In the 90%-10% isocratic elution, the HGA is eluted in 1.2 min whereas in the 92%-8% isocratic system, it is eluted in 1.4 min. The elution is generally recorded at 230 nm. Van den Tweel et al. (1986) used 2,2'-bipyridyl (non-heme iron protein inhibitor) to inhibit the homogentisate dioxygenase and thus allow accumulation of the HGA. For this reason, 2 mM of 2,2-bipyridyl is added to certain reaction media. Under these chromatographic conditions, it is possible to identify the 4-HPA and the HGA. The HPLC system consists of an Alliance 2690 HPLC (Waters) and a 996 diode array detector (Waters).

II.1.2.3—Purification of the HPAH Protein

*Pseudomonas acidovorans* is cultured for 48 hours on M63 medium containing 4-HPA as the only carbon source, at 29° C. 220 rpm. The bacteria are centrifuged at 3000 g for 15 min at 6° C. (Beckmann J2/21 M/E centrifuge). The bacterial pellet is taken up in the sonication buffer (0.1 M KPi, pH 7.2; 1 mM $MgSO_4$; 1 mM DTT; 1 mM benzamidine hydrochloride; 5 mM caproic acid). Benzamidine hydrochloride and caproic acid are protease inhibitors. The sonication is carried out for 9 minutes, sonicating every forty seconds for twenty seconds at power 5 (Vibra Cell, Sonic Materials INC., Connecticut, USA). During the sonication, the sample is kept at the temperature of melting ice. The sonicated extract is centrifuged at 15 000 g for 15 min at 4° C. The supernatant recovered is precipitated with 1% of streptomycin sulfate. The precipitate is eliminated by centrifugation at 15 000 g for 15 min at 4° C. The supernatant is desalified on a PD10 column (Pharmacia) and then loaded onto a DEAE/EMD 650 S column equilibrated in buffer A (20 mM KPi, pH 7.2, 10% glycerol, 1 mM $MgSO_4$, 1 mM DTT). The elution is carried out using a buffer B (buffer A; 1 M KCl; 100 μM FAD). The 4-HPA 1-hydroxylase activity is eluted for a KCl concentration in the region of 150 mM. The active fractions, concentrated through UVIKON 10 kDa membrane and then desalified on a PD10 column, are then loaded onto a Red affinity column (Red 120 Agarose type 3000 CL, SIGMA Ref R-0503) equilibrated in buffer A (above). The elution is carried out in two stages. The first is washing of the Red column using buffer A enriched with FAD at a final concentration of 50 μM. The second allows elution of the protein; for this, buffer A is enriched in FAD (3 mM) and in NADH,$H^+$ (10 mM). The fractions, containing the protein of interest, are pooled, concentrated and frozen at −80° C.

II.1.3—Protein Microsequencing of the N-Terminal End and of Internal Peptides

The same protocol as that described in the case of the HPP oxidase was used to carry out the sequencing of the purified protein. However, in order to produce the internal peptides, the protein was digested with trypsin instead of Lys-C endopeptidase. Trypsin cleaves after arginines and lysins. Digestion with trypsin generally leads to the production of fragments which are smaller than those obtained in a digestion with Lys-C endopeptidase. In order to be able to sequence with precision the recovered peptides, it is sometimes necessary to repurify the recovered peptides by HPLC.

II.1.4—Identification of a Portion of the Gene Encoding the HPAH by Degenerate PCR The degeneracy code given on page 43 [of the original] is used for the synthesis of the degenerate primers. The PCR is carried out in a final volume of 50 μL, in 200 μL tubes. The reaction solution contains the Perkin Elmer buffer, 250 μM dNTP, 50 ng of *P. acidovorans* genomic DNA, and 2 enzyme units of AmpliTaq (Perkin Elmer). The reaction is carried out using a “Hybaid Touchdown” thermocycler: 3 min at 94° C., then forty five cycles: 30 sec at 94° C., 1 min at 50° C., 1 min 30 sec at 72° C., followed by a final elongation of 5 min at 72° C. before returning to 4° C., The PCR is evaluated after loading 10 μL onto a 1% agarose gel. Under these conditions, a 536 bp band is identified.

II.1.5—Screening of the *P. acidovorans* Cosmid Library

The cosmid library is plated out on $LBT^{15}$ medium and allowed to grow for 16 h at 37° C. The dishes are then transferred to 4° C. After one hour, the colonies are transferred to Hybond N membranes (Amersham) according to the method of Grunstein & Hogness (1975). The membranes are hybridized using the 536 bp PCR fragment previously identified and purified. Detection is carried out with $^{32}P$. The probe is labeled using the “DNA Ready to Go” kit (Pharmacia). The prehybridization, hybridization and washing are carried out in vials. The membranes are prehybridized in a solution composed of 5×SSC, 6% Denhardt’s and 0.5% SDS, for 4 hours at 68° C. The hybridization is carried out for 16 hours at 68° C. The washes are carried out at 65° C. in 2×SSC, 0.1% SDS. The membranes are developed by exposing Kodak or Amersham films.

II.1.6—*P. putida* Growth Media

*Pseudomonas putida* is cultured on Luria-Bertani (LB) or 2YT rich medium containing 100 $\mu g.mL^{-1}$ of rifampicin. Other antibiotics are added as needed (example: tetracyclin at 15 $\mu g.mL^{-1}$). The minimum medium M63 containing 1.5 $g.L^{-1}$ of 4-HPA as the only carbon source is used to test the functional complementation. In this case, the antibiotics are omitted. All the cultures are prepared at 29° C.

II.1.7—Transformation of *P. putida* by Electroporation 1 liter of LB Rifampicin (100 $\mu g.mL^{-1}$) medium is inoculated with a culture of *P. putida* grown at 29° C. for approximately 16 hours with shaking at. 180 rpm. When the $OD_{600\ nm}$ is in the region of 1.2, the cells are collected by centrifugation for 15 min at 3000 g, 4° C. The culture medium is removed and the cells are taken up with 400 mL of 10% glycerol at 4° C. The cells are centrifuged once again at 3000 g for 20 min at 4° C. Two further washing steps are carried out with, respectively, 200 then 100 mL of 10% glycerol at 4° C. Finally, the bacteria are taken up with 3 to 10 mL of 10% glycerol and then distributed into 100 μL aliquots which are immediately frozen in liquid nitrogen. The bacteria thus prepared are conserved for at least six months at −80° C. During the preparation, a loss of bacteria due to lysis is observed. The cosmid ($Tet^R$) DNA is introduced into the *P. putida* ($Rif^R$) by electroporation. The electroporation (Bio-Rad Gene Pulser™) of 80 ng of cosmid DNA into 100 μL of electrocompetent *P. putida* is carried out in a 2 mm electroporation cuvette under a voltage of 0.9 volts with an electroporator resistance of 200Ω. Under these conditions, the time constant τ is approximately 4.5 msec. After the electric shock, the cells are taken up with 900 μL of LB and cultured for 1 h 30 at 29° C., 180 rpm. The transformed *P. putida* are selected on LB $Rif^{100}$ $Tet^{15}$ agar medium.

II.1.8—Modification of the Broad Host Spectrum Vector pBBR1MCS-$Gm^R$

We used the broad Gram-negative host spectrum vectors of the pBBR1MCS series (Kovach et al., 1994, 1995). These plasmids, which have a *Bordetella bronchiseptica* origin of replication replicate at approximately 20-30 copies per cell in *E. coli*. They contain two Not I sites. In order to facilitate the subsequent clonings, the Not I site present outside the multiple cloning site (MCS) on the plasmid pBBR1MCS-$Gm^R$ is deleted. For this, the plasmid is cleaved with Sfi I (50° C.) and then treated with T4 DNA polymerase in order to obtain blunt ends. The plasmid is religated on itself (T4 DNA Ligase—New England Biolabs). After ligation (16 hours, 16° C.), a digestion with Sfi I is carried out in order to eliminate the possible “wild-type” plasmids, and then *E. coli* DH5α are electroporated. The plasmid DNA is isolated from the clones selected on LB $Gm^{20}$ medium. The plasmid DNAs are characterized with two digestions: Not I and Not I/Bgl II. A clone is selected: pBBR1MCS-Gm-Not-U.

II.1.9—Subcloning of Ccos8 in pBBR1MCS-Gm-U

The cosmid Ccos8 is restricted with Not I and then loaded onto an agarose gel. After migration, 6 DNA bands are visualized: 1.7; 3; 4; 5; 8; 10 kbp. The bands are purified with Quiaex II. Moreover, pBBR1MCS-Gm-Not-U is restricted with Not I, and dephosphorylated using shrimp alkaline phosphatase (SAP). The various bands are then ligated (T4 DNA ligase, 16 hours, 16° C.) into the vector using varying “insert/vector” ratios. *E. coli* DH5α are transformed with the ligation products.

II.1.10—Triparental Conjugation Between *E. coli* and *P. putida*

In order to transfer the various Ccos8 ($Gm^R$) subclones from *E. coli* DH5α to *P. putida* ($Rif^R$), tripartenteral conjugation is carried out on a filter using the protocol described by De Lorenzo et al. (1990). The bacteria recovered are plated out on LB $Rif^{100}$ $Gm^{20}$ and on M63 having 4-HPA as the only carbon source.

II.1.11—Elimination of the Plasmid p5kbC

In order to rapidly eliminate the plasmid p5kbC of *P. putida*, the incompatible origins of replication strategy is used, and the loss of p5kbC is forced using antibiotics. *P. putida* ($Rif^{100}$) complemented with the plasmid p5kbC ($Gm^R$) is transformed with pBBR1MCS $Kn^R$. The clones obtained ($Rif^{100}$ $Gm^R$ $Kn^R$) are verified for their complementation activity. The clones are then cultured on two media: LB $Rif^{100}$ $Kn^{150}$ $Gm^{20}$ and LB $Rif^{100}$ $Kn^{150}$. In doing this, the selection pressure for p5kbC and pBBR1MCS KnR or else only for pBBR1MCS $Kn^R$ is maintained. Growth is carried out at 29° C. The subculturing is carried out every three days. At the eighth subculturing, the colonies are subcultured on 4 different media (M63, M63+4-HPA, LB $Rif^{100}$ $Kn^{150}$ $Gm^{20}$ and LB $Rif^{100}$ $Kn^{150}$) whatever the dish of origin. The state growth is then recorded after 2 and 7 days.

II.1.12—Identification of the Proteins Contributing to the Enzyme Activity

II.1.12.1—Preparation of Crude Extracts of *P. putida*

Two *P. putida* clones are cultured on LB $Gm^{20}$ for 24 hours. The first comprises the plasmid pBBR1MCS-Gm-Not-U, while the second contains the complementation plasmid p5kbC. After sonication in a buffer (0.1 M KPi; 1 mM $MgSO_4$; 1 mM DTT; 1 mM benzamidine hydrochloride; 5 mM caproic acid), then centrifugation at 20 000 g for 10 min at 4° C., the supernatant is tested for its 4-HPA 1-hydroxylase activity using the two methods for measuring enzyme activity. The crude extracts are also analyzed by SDS-10% PAGE.

II.1.12.2—Transfer onto Membrane, N-Terminal Sequencing

The sequencing is carried out as in Example I.

II.1.12.3—S75 Gel Filtration

The eluate (5 mL) is concentrated 10-fold using a 10 K Macrosep™ (Pall Filtron) for two hours at 4° C. The concentrated 500 µL are injected onto a Superdex™ 75 prep grade gel filtration column (HiLoad 16/60, Pharmacia) pre-equilibrated with 700 mL of buffer (0.02 M KPi, pH 7.2; 10% glycerol; 1 mM $MgSO_4$; 1 mM DTT; 4° C.) at a flow rate of 0.7 $mL.min^{-1}$. The chromatography is carried out at 4° C. with a flow rate of 1 $mL.min^{-1}$. The fractions are collected every minute and stored at 4° C.

II.1.12.4—Construction of pBBR1MCS FT12Δ1

Figure 6:
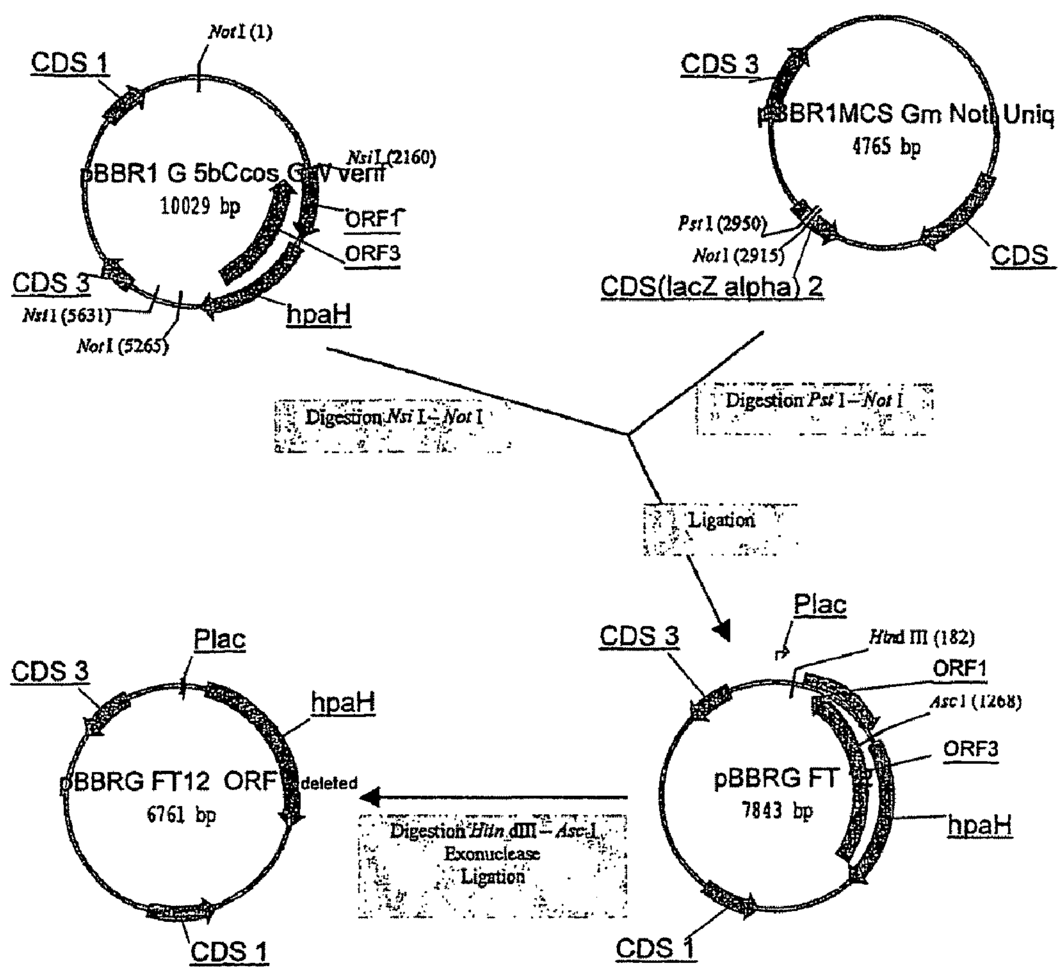
FIG. 6 shows the construction of plasmid pBBR1MCS FT12Δ1.

To construct the plasmid pBBR1MCS FT12Δ1, a two-step cloning strategy is used. The plasmid p5kbC is digested with Nsi I and Not I. The insert obtained, encoding genes 1, hpaH and 3, is then cloned into pBBR1MCS-Gm-Not-U digested with Pst I and Not I. The resulting clone, named pBBR1MCS FT12, is restricted with Hind III and Asc I, then blunt-ended and, finally, religated. In doing this, genes 1 and 3 are destroyed and the hpaH gene is under the control of the lac promoter of the original vector. The plasmid pBBR1MCS FT12Δ1 is thus obtained (FIG. 6).

II.1.12.5—Construction of pL1lac2

The laboratory possesses a plasmid named "Clone L". This construct corresponds to the cloning of the *P. fluorescens* HPPD gene promoter into the vector pBBR1MCS-$Kn^R$. The HPPD gene promoter is functional in *P. putida* and in *E. coli*. The plasmid "Clone L" is digested with Bam HI and Hin dIII, which makes it possible to recover the insert containing the promoter and the HPPD gene of *P. fluorescens*. This insert is then ligated into the vector pBBR1MCS-$Gm^R$ digested with Bam HI and Hin dIII. The resulting clone is named pBBRG-L-HPPD. The plasmid obtained, digested with Nco I to remove the gene encoding HPPD, is ligated with the hpaC gene amplified by PCR and digested with Afl III. The construct obtained is called pBBRG-L-ORF1. To amplify the hpaC gene by PCR, primers which make it possible to introduce an Afl III site at the beginning and at the end of the gene (the Afl III site is compatible with the Not I site) are used. The primers used are: positioned 5' of the gene: GCAGGATGCA CATGTCCACC AAGAC (SEQ ID NO: 33) and positioned 3' of the gene: CGGACGCCGA CATGTATCAG CCTTC (SEQ ID NO: 34). The PCR is carried out using 1 unit of KlenTaq polymerase (Sigma), 250 µM of dNTP, 200 nM of each primer and 50 ng of the plasmid p5kbC. The PCR program is defined as follows, on a Perkin Elmer 9600: 3 min at 95° C.; then 20 cycles: 94° C. for 1 min, 60° C. for 30 sec, 68° C. for 3 min; finally, a last step of 10 min at 68° C. is carried out. The plasmid pBBR1MCS FT12Δ1 previously obtained is restricted with Ssp I and Not I. The Not I site is blunt-ended by treatment with Pfu. The fragment recovered (2468 bp), containing the hpaH gene under the control of the lac promoter, is ligated into pBBRG-L-ORF1 digested with Ssp I. The clone containing the hpaC gene and hpaH gene in the antisense direction is selected and is named pL1lac2. All this cloning is carried out in *E. coli* DH5α.

II.2—Results

Various approaches can be envisioned for identifying the gene encoding the 4-HPA 1-hydroxylase activity of *P. acidovorans*. We decided initially to use an approach by phenotypic coloration. This approach appears to be simple and rapid. We in fact possess in the laboratory a phenotypic screening tool for detecting the production of HGA. Now, the enzyme being sought converts 4-HPA to HGA.

II.2.1—Approach by Phenotypic Coloration

We have observed in the laboratory that *E. coli* K12 cannot grow using tyrosine or 4-HPA as the only carbon source. In addition, we know that *E. coli* K12 has tyrosine aminotransferase activity which allows synthesis of tyrosine from HPP. This enzyme activity is reversible, and the cell can therefore produce HPP from tyrosine. If the rich culture medium is enriched in tyrosine (1 $g.L^{-1}$), the tyrosine is imported into the bacteria, which accumulate it and then convert it to HPP, according to the equilibrium constant for the conversion reaction between HPP and tyrosine. In the laboratory, we have already observed that, if we introduce the *P. fluorescens* HPPD into *E. coli* K12, then the HPP produced during the deamination of tyrosine is converted into homogentisate (HGA). Since the reaction catalyzed by the HPPD is irreversible, the HGA accumulates in the cell, where it is oxidized then polymerizes spontaneously to form an ochronotic pigment which is brown in color. This therefore gives us a means of detecting the production of HGA. The 4-HPA 1-hydroxylase being sought converts 4-HPA to HGA. The *E. coli* HB101 containing the *Pseudomonas* acidovorans genomic library are therefore plated out on 2YT agar medium enriched in 4-HPA. After two days, two colonies become brown: they therefore produce homogentisate. However, the enzyme activities detected on the crude extracts of these two clones reveal enzyme activity of the HPPD type whereas the 4-HPA 1-hydroxylase activity sought is discrete, or even nonexistent. A priori, this approach made it possible to select the clones for which the cosmid contains the gene encoding a *P. acidovorans* HPPD and not the 4-HPA 1-hydroxylase. In the in vitro preliminary study on the crude extracts of *P. acidovorans*, the HPPD activity was not identified. It may be presumed that the *P. acidovorans* HPPD activity would be expressed when the bacterium is cultured on rich medium, whereas the 4-HPA 1-hydroxylase activity would be expressed when 4-HPA is the only carbon source. Since this approach did not make it possible to identify the 4-HPA 1-hydroxylase, we decided to purify the enzyme. Once the protein is identified, it is possible to work back to the corresponding gene.

II.2.2—Purification of the 4-HPA 1-hydroxylase

In order to follow the purification of the protein, its 4-HPA-dependent NADH,$H^+$ oxidase activity is assayed. The protein is thus purified to virtual homogeneity by applying the purification protocol described above. The enrichment factor for the specific NADH,$H^+$ oxidase activity is generally between 50 and 100 depending on the preparations. On SDS-PAGE, the protein has an apparent molecular weight of 60 kDa. In fact, it is observed that the NADH,$H^+$ oxidase activity and the production of HGA are visible on leaving DEAE/EMD 650S. On the other hand, on leaving an affinity column, the production of HGA is very difficult to detect; the NADH,$H^+$ oxidase activity remains, however, dependent on 4-HPA being added to the reaction medium. If the hypothesis that the enzyme is monomeric is taken as a basis, the loss of catalytic activity allowing the production of HGA can be explained by supposing that a part of the protein has been damaged (for example: loss of a strongly associated cofactor) during its passage through the Red column. The site catalyzing the oxidation of NADH,$H^+$ would not be affected. It may also be supposed that the enzyme sought is a heterodimer. The loss of catalytic activity would then be explained by the loss of the monomer responsible for the production of HGA. Many heterodimeric flavin monooxygenases have been identified in the literature, all having an aromatic substrate, in varied bacterial species (Adachi et al., 1964; Arunachalam et al., 1992, 1994; Prieto et al., 1993; Prieto & Garcia, 1994; Arunachalam & Massey, 1994; Takizawa et al., 1995; Xun, 1996; Xun & Sandvik, 2000). However, two hypotheses exist to explain the function of these heterodimeric enzymes:

(1) Arunachalam et al. (1992, 1994) proposed that the 4-hydroxyphenylacetate 3-hydroxylase of *P. putida* consists of a 65 kDa homodimeric flavoprotein and also a 38.5 kDa coupling protein. The flavoprotein alone is capable of oxidizing NADH,$H^+$ independently of the presence of 4-HPA. This oxidation of NADH,$H^+$ makes it possible to renew the $NAD^+$ "pool", but produces $H_2O_2$ in stoichiometric proportions. If the coupling protein is added, the protein complex becomes capable of hydroxylating 4-HPA to 3,4-dihydroxyphenylacetic acid. Thus, the oxidation of NADH,$H^+$ is not wasted and allows the synthesis of a metabolite. The coupling protein alone has no enzyme activity.

(2) Prieto et al. (1993, 1994) and Xun & Sandvik (2000) suggest that the 4-HPA 3-hydroxylase of *E. coli* W (ATCC 11105) is considered to be a new member of the two-component flavin-diffusible monooxygenases (TC-FDM). The two components would be, firstly, 4-hydroxyphenylacetate 3-hydroxylase, a 59 kDa monomeric enzyme encoded by the HpaB gene and, secondly, a 19 kDa monomeric flavin: NADH oxidoreductase encoded by the HpaC gene. In this case, FAD is reduced at the expense of NADH,$H.^+$ by the flavin: NADH,$H^+$ oxidoreductase. The $FADH_2$ is then used by the oxygenase to allow oxidation of the substrate using molecular oxygen.

The enzyme that we purified strongly oxidizes, NADH,$H^+$ but produces very little homogentisate. In addition, the oxidation of NADH,$H^+$ is dependent on 4-HPA being added. This suggests that we have an enzyme of the type of that described by Prieto et al. We therefore consider that the purified enzyme is the 4-HPA 1-hydroxylase (HPAH) sought. It is possible that, subsequently, it will be necessary to identify a coupling protein in order to optimize the enzyme activity. The biochemical approach can therefore be continued with the purified protein.

II.2.3—Production of the Internal Peptides and of the N-Terminal Sequence

The purified protein was sent to the Pasteur Institute to be microsequenced. Thus, the N-terminal sequence SHPAISLQAL RGSGADIQSI HIPYER (SEQ ID NO: 35) and six internal peptides named, respectively, peptides No. 11C, 12D, 20A, 22B, 23 and 24, as a function of the order in which they leave the column: ATDFITPK (SEQ ID NO: 36), LGVGQPMVDK (SEQ ID NO: 37), VVFAGDSAHG VSPFX (SEQ ID NO: 38), VTALEPQAEG AL (SEQ ID NO: 39), IDFQLGWDAD PEEEK (SEQ ID NO: 40), LSVPATLHGS ALNTPDTDTF (SEQ ID NO: 41), were thus obtained. The amino acid (methionine or valine) normally corresponding to the initiation codon of the gene (ATG or GTG) is not found on the N-terminal sequence. Homology analyses in the protein bases using the BLASTP algorithm do not make it possible to identify homologous proteins. On the basis of the protein sequences obtained, the corresponding degenerate oligonucleotides were synthesized. These oligonucleotides were used in PCR reactions in order to identify a portion of the gene encoding the purified and partially sequenced HPAH protein.

II.2.4—Production of the PCR Fragment

PCR amplification of a portion (536 bp) of the gene encoding the 4-HPA 1-hydroxylase was obtained using the degenerate primers Hy4R: TCYTCNGGRT CNGCRTCCCA (SEQ ID NO: 42) and Hy5F: GGNGTNGGNC ARCCNATGGT (SEQ ID NO: 43) which encode, respectively, peptides 23 and 12D. These primers have a hybridization temperature of 55.4° C. and exhibit a degeneracy of 128 and 512 respectively. The amplified sequence is cloned into the vector pGEMT-easy and is then sequenced. Analysis of the sequence obtained makes it possible to find, besides the sequences encoding the peptides Hy4R and Hy5F, the nucleic acid sequence encoding internal peptide 22B. The latter element makes it possible to confirm that we have indeed amplified a portion of the gene encoding the purified HPAH protein. At this stage, homology searches in the protein bases, using the BLASTX algorithm, bring up some weak homologies with hydroxylases, oxidases and monooxygenases. Using the 536 bp PCR-amplified sequence, we will be able to screen a *P. acidovorans* cosmid library in order to search for the cosmid containing the complete gene.

II.2.5—Screening of the *P. acidovorans* Cosmid Library

Screening of the cosmid library, using as probe the sequence obtained above, made it possible to identify 4 groups of cosmids considered to be different on the basis of their restriction and hybridization profiles after transfer by the Southern technique. Cosmids No. 1, 2 and 6 form the first group, cosmids No. 3, 7 and 9 form the second, while cosmids No. 5 and 8 form the third. The final group is represented by cosmid No. 4. The hybridization results suggest, in addition, that the hpaH gene sought is present as a single copy in the genome of *Pseudomonas acidovorans*. We identified cosmids comprising at least a portion of the gene encoding the purified HPAH protein. In the meantime, we observed that *P. putida* was incapable of growing on 4-HPA but could grow using HGA as the only carbon source. This therefore gives us an excellent screen for functional complementation; we will thus be able to define which of these cosmids comprises the functional gene encoding the 4-HPA 1-hydroxylase activity.

II.2.6—Functional Complementation with the Cosmids

The nine cosmids previously identified are introduced into *P. putida* by electroporation. The clones obtained are then subcultured on M63 medium containing 4-HPA as the only carbon source. After 7-8 days, only the bacteria containing cosmid No. 8 succeeded in growing; that is to say, only cosmid. No. 8 contains all the expressible information allowing conversion of 4-HPA to HGA which can be used by *P. putida*. The cosmid is named Ccos8. The transformation with all the cosmids was repeated. It was always cosmid 8 which allowed complementation after a certain period of time (6-10 days). In order to be able to move forward in our approach of determining the minimum DNA fragment expressing the 4-HPA 1-hydroxylase activity, it is necessary to subclone Ccos8. The subclone of interest is selected using the functional complementation screen.

II.2.7—Subcloning by Functional Complementation

Digestion of the cosmid with Not I makes it possible to obtain 6 DNA fragments of between 1.7 and 10 kb in size. These fragments were subcloned into pBBR1MCS-Gm-Not-U. Five subclones of Ccos8 were obtained. Restriction analysis showed that the 4 and 10 kb fragments were not subcloned. On the other hand, we observed that the 5 kb band initially observed was in fact a double band of 5.1 and 5.2 kb. These clones were passed, by triparenteral conjugation, from *E. coli* to *P. putida*. After 5 days, only *P. Putida* containing the subclone corresponding to the 5.2 kb band of the cosmid Ccos8 grew on M63 containing 4-HPA as the only carbon source. We had therefore just, identified the minimum fragment comprising the 4-HPA 1-hydroxylase activity. The clones corresponding to the 5.2 kb are named 5 kbC. To confirm the result of the functional complementation, we caused the plasmid p5kbC to be eliminated using the strategy of incompatible origins of replication and forcing the elimination of the plasmid p5kbC, by selection pressure from the antibiotics used. We observed that *P. putida* lost the ability to grow on 4-HPA as the only carbon source when it lost the plasmid p5kbC. We concluded therefrom that the 4-HPA 1-hydroxylase enzyme activity is clearly carried by the plasmid p5kbC. We could therefore have the 5.2 kb insert sequenced, which should allow us to identify the functional hpaH gene.

II.2.8—Analysis of the 5.2 kb Sequence

The 5.2 kb insert of the plasmid p5kbC was sequenced. A nucleic acid homology search (BLASTN) thus made it possible to identify three portions in the insert. The first portion between bases No. 1 and 1465 is completely homologous to a portion of the plasmid Birmingham IncP-alpha. It is therefore probably, a sequence derived from pLAFR5. A second nucleic acid portion between bases No. 1466 and 1695 exhibits its complete homology with a portion of the cloning plasmid M13 mp 8/pUC8. This sequence is therefore also part of pLAFR-5; specifically, the multiple cloning site of pLAFR-5 originates from pUC8 (Keen et al., 1988). Thus, the Eco RI and Sma I sites (FIG. 7) at respective positions 1689 and 1695 are probably the cloning sites of pLAFR-5. The third portion, between bases 1696 and 5264 (i.e. 3568 bp), does not exhibit any strong homologies. This portion of DNA originates from the *P. acidovorans* genome. When the 5.2 kb sequence is analyzed using the BLASTX algorithm, probable proteins are identified (FIG. 7). Thus, the protein encoded by gene 1 exhibits weak homologies with beta-lactamases, dehydrases and cyclases. The purified protein is encoded by gene 2 since the sequences encoding the internal peptides previously obtained are found; it is therefore probably the 4-HPA 1-hydroxylase. The protein alignments show that this protein exhibits some homologies with oxygenases and hydroxylases. The protein potentially encoded by gene 3 exhibits no homologies with the databases. Finally, gene 4 probably encodes an operon regulator.

A finer analysis of hpaH gene will now be made. According to the N-terminal protein sequence obtained, the ATG initiation codon of the 4-HPA 1-hydroxylase protein is in fact 78 bp downstream of a GTG initiator codon in phase with the ATG. The Shine-Dalgarno sequence AGGA, allowing ribosome binding, is found upstream of the initiator ATG but not upstream of the GTG initiator codon, which confirms that the coding region begins at the ATG initiator codon. The portion between the GTG and ATG codons probably does not therefore correspond to a preprotein. Thus defined, the hpaH gene is 1737 bp long and ends with the TGA stop codon. The gene consists of 70.9% of GC bases.

Now that we have defined with precision the limits of the hpaH gene, the product of its translation: the HPAH protein, will be analyzed.

II.2.9—Analysis of the HPAH Protein

The hpaH sequence is translated using the universal codon system. A 563 amino acid protein is thus obtained, which represents a molecular weight of 62.2 kDa. The protein homology searches (BLASTP) show that the HPAH exhibits approximately 15 to 25% identity essentially with proteins of Gram-positive organisms, encoding enzyme activities apparently very different from that sought. Thus, a *Streptomyces argillaceus* oxygenase, *E. coli* 3-(3-hydroxyphenyl)propionate hydroxylase (EC 1.14.13.-), *Sphingomonas* sp. 2,4-dihydroxybenzoate monooxygenase, the enzyme catalyzing the 6-hydroxylation of tetracycline in *Streptomyces aureofaciens*, and a potential *Streptomyces fradiae* oxygenase are found. In fact, the HPAH exhibits homologies with the proteins of the phenol monooxygenase (pheA) family and those of the 2,4-dichlorophenol hydroxylase (tfdB) family. The alignment corresponding to the abovementioned proteins is performed using the ClustalW algorithm (FIG. 8). It makes it possible to demonstrate very conserved boxes. Three units of interaction with FAD are noted, inter alia. The first (GXGXXG) (SEQ ID NO: 44) corresponds to the β-α-β structural unit which allows interaction of the ADP component of FAD with the protein. The second unit, (A/C)DG, is involved in the binding of FAD, while the third unit, G(R) VXX(A)GD(A)XH (SEQ ID NO: 45), allows interaction with the flavin component of FAD. Although the enzyme uses NADH,$H^+$, the corresponding binding site (GDH) is not identified. This absence of NADH,$H^+$-binding site is a characteristic often observed in other FAD monooxygenases. Finally, a unit (DXXXLXWKLX XXXXXXXXXX LLXXYXXER) (SEQ ID NO: 46) is observed which is also found in other hydroxylases (Ferrandez et al., 1997), but the meaning of which is not understood. Although the 3-(3-hydroxyphenyl) propionate hydroxylase of *E. coli* catalyzes a hydroxylation reaction on a substrate structurally close to 4-HPA, the information acquired with this bioinformatic analyses does not make it possible to be sure that we have indeed identified the 4-HPA 1-hydroxylase. The only way to do this is to express the hpaH gene and to study its enzyme activity.

II.2.10—Identity of the Proteins Involved in the 4-HPA 1-hydroxylase Activity

II.2.10.1—Expression of the hpaH Gene Encoding the 4-HPA 1-hydroxylase Activity

In order to confirm that the hpaH gene encodes the 4-HPA 1-hydroxylase activity, it is necessary to express the gene. To do this, a two-step cloning strategy is used, making it possible to eliminate genes No. 1 and 3 and to place the hpaH gene under the control of the lac promoter of the original vector pBBR1MCS-Gm-Not-U. The plasmid obtained is named pBBR1MCS FT12Δ1. A crude extract is produced from a culture, on rich medium, of *P. putida* transformed with this plasmid. The search for activity by spectrophotometry (at 340 and 292 nm) shows that the clone definitely has the NADH,$H^+$ oxidase activity induced by adding 4-HPA, but does not have the ability to synthesize homogentisate from the 4-HPA. On the other hand, the appearance of a molecule Z having a very close retention time (tr=1.2 minutes versus 1.4 minutes) but a UV spectrum very different from that of HGA. We put forward the hypothesis that HPAH oxidizes NADH,$H^+$ so as to reduce its cofactor FAD. The reoxidation of FAD takes place to the detriment of 4-HPA since it is the addition of 4-HPA which initiates the reaction. The 4-HPA is therefore converted to metabolite Z. The UV spectrum of this metabolite suggests that the ring is no longer aromatic but may, however, be unsaturated. A structural hypothesis for metabolite Z is presented in FIG. 2. This experiment shows that the lac promoter is functional in *P. putida* in the absence of IPTG inducer, which suggests that the lacI repressor is naturally absent in *P. putida*. We also demonstrate that the protein initially purified (HPAH) is really a 4-HPA-dependent NADH,$H^+$ oxidase which converts 4-HPA to metabolite Z. The HPAH does not produce HGA. It is therefore necessary to identify the partner protein(s) of this NADH,$H^+$ oxidase dependent on 4-HPA, the addition of which makes it possible to restore the 4-HPA 1-hydroxylase activity.

II.2.10.2—Identification of the HPAC Protein by Gel Filtration

We have seen that the 4-HPA 1-hydroxylase activity disappeared during the purification of the HPAH on a Red affinity column. We therefore put forward the hypothesis that the partner protein(s) of the 4-HPA-dependent NADH,$H^+$ oxidase were not retained by the Red 120 agarose affinity resin and are therefore recovered in the flow-through. We therefore decided to purify the flow-through and to search for the protein(s) which, when added to the HPAH, made it possible to restore the 4-HPA 1-hydroxylase activity. To do this, the flow-through is concentrated by ultrafiltration (10K Macrosep™) and then loaded onto an S75 gel filtration column. A flow rate of 1 $mL.min^{-1}$ is applied and the 1 mL fractions are collected. Enzyme reactions are then carried out, mixing together 50 μL of each fraction and 10 μL of HPAH purified beforehand on a Red column, under normal reaction conditions. The stopped reactions are then analyzed by HPLC. It is observed that fractions 90 to 108, when added to HPAH protein, make it possible to produce more metabolite Z. The production of metabolite Z is detected in these same fractions in the absence of introduction of HPAH. Moreover, on the acrylamide gel corresponding to these fractions, we observe a protein of molecular weight equivalent to HPAH. We concluded that the flow-through still contained a little HPAH protein. When fractions 109 to 143 are added to the HPAH protein, the production of HGA is observed. The greater the production of HGA, the weaker the production of metabolite Z. The maximum production of homogentisate is obtained for fractions 116 to 128. Loading the fractions between 95 and 145 onto acrylamide gel shows that a protein is highly enriched in fractions 109 to 143, i.e. the chromatographic profile of this protein coincides with the production profile of HGA. We decided to name this protein HPAC. The HPAC protein is excised from the gel and then microsequenced at the N-terminal. The sequence obtained, MTTKTFA (SEQ ID NO: 47), shows that this protein is encoded by gene 1 (FIG. 7), which we henceforth named hpac. This experiment shows that the 4-HPA 1-hydroxylase activity involves two proteins, HPAH and HPAC. However, we have not defined the nature of the interaction between these two proteins: (1) are HPAH and HPAC both enzymes, or else (2) does HPAH have an enzyme activity which is modifiable as a function of the interaction with HPAC.

II.2.10.3—Nature of the Interactions Between HPAH and HPAC

The preceding experiment demonstrates that the HPAH and HPAC proteins are necessary to reconstitute the 4-HPA 1-hydroxylase activity. Two hypotheses to explain the respective role of these proteins are put forward. In this paragraph, we present the results which suggest that HPAC is an enzyme in its own right. Fractions 100, 101 and 102 from the gel filtration are pooled. They contain the HPAH, i.e. the NADH, $H^+$ oxidase activity which makes it possible to produce metabolite Z from 4-HPA. Moreover, fractions 123, 124 and 125 from the gel filtration are pooled. They contain the HPAC. Various enzyme reactions are carried out using the HPAH and/or the HPAC. These reactions are carried out in two steps. A first reaction is carried out with the HPAH (respectively HPAC), and it is stopped after 30 minutes by heat treatment (100° C., 10 min). The HPAC (respectively HPAH) is then added and the reaction is pursued for 30 minutes. The reaction is finally stopped by adding perchloric acid. Reactions are also carried out by replacing one of the enzymes with water. Finally, equivalent experiments are carried out by filtering the reactions through 10 kD Nanosep™ (Pall Filtron) instead of boiling them.

Table No. 1 summarizes the results obtained

| Experiment No. | Enzyme No. 1 | Enzyme No. 2 | Metabolite observed |
|---|---|---|---|
| | HPAH, HPAC | / | HGA |
| A | HPAH | $H_20$ | metabolite Z |
| B | HPAH | HPAC | HGA |
| C | $H_2O$ | HPAC | / |
| D | HPAC | $H_20$ | / |
| E | HPAC | HPAH | metabolite Z |
| F | $H_2O$ | HPAH | metabolite Z |

We observe that the only way to produce the HGA is to have the two proteins HPAH and HPAC simultaneously or successively in this order. When the HPAH is alone, or when the HPAC is introduced before the HPAH, only metabolite Z is detectable. Finally, the HPAC protein has no enzyme activity on 4-HPA. These results suggest that metabolite Z is a reaction intermediate. The HPAH would convert 4-HPA to metabolite Z, this reaction allowing the oxidation of NADH, $H^+$. Metabolite Z would then be converted to HGA by the HPAC. Physical interactions between the two proteins do not appear to be necessary since the HPAH protein can be denatured or removed by filtration before adding the HPAC. We have shown, in vitro, that the 4-HPA 1-hydroxylase activity depends on the HPAC and HPAH protein. However, the HPAC protein is not pure on exiting on gel filtration, it is only enriched. It therefore remains possible that, in reality, it is another protein contained in this enriched extract which converts metabolite Z to HGA. In order to eliminate the doubts, we decided to clone the two genes (hpaC and hpaH) on the same vector; in this case, we should produce the 4-HPA 1-hydroxylase activity and therefore be able to make *P. putida* grow on minimum medium containing 4-HPA as the only carbon source.

II.2.10.4—Functional Complementation of *P. putida* with hpaH and hpaC

The plasmid pL1lac2 (FIG. 9) is a vector pBBR1MCS-$Gm^R$ containing the hpaC gene under the control of the *P. fluorescens* HPPD promoter and, in the opposite direction, the hpaH gene under the control of a lac promoter. The plasmid is introduced into *P. putida* by electroporation. The bacteria are then plated out on minimum medium containing or not containing 4-HPA as the only carbon source. After 5 days, the colonies are visible only on dishes containing 4-HPA as the only carbon source. After 8 days, the colonies are a good size. The plasmid DNA extracted from these colonies confirms the presence of the whole plasmid pL1lac2. Moreover, *P. putida* is incapable of growing on 4-HPA when the bacterium is transformed with the vector pBBR1MCS-$GM^R$ containing either the hpac gene or the hpaH gene. The functional complementation obtained in this experiment confirms that the hpaC and hpaH genes are necessary and sufficient to initiate the 4-HPA 1-hydroxylase activity sought.

Example III

Construction of the Various Cytosolic Expression Cassettes

III.1-HPAC

The HPAC gene was isolated from *Pseudomonas acidovorans* by PCR on a plasmid derived (p5kbC) from a genomic DNA cosmid library, using the following oligonucleotides:

```
Start ORF1 (AflIII):
GCAGGATGCA CATGTCCACC AAGAC (SEQ ID NO: 48)

ORF1 Fin (HindIII):
CGGACGCAAG CTTGCATCAG CCTTC (SEQ ID NO: 49)
```

The reaction was carried out according to standard conditions. The amplified fragment, 993 bp in size, was subcloned into the plasmid pGEMTeasy (Promega) according to the supplier's protocol. The plasmid pOZ150 thus obtained was sequenced. The cassette obtained by EcoRI+SpeI digestion was cloned into the plasmid pBluescriptII-KS+ opened with the same enzymes, to give the plasmid, pEPA13. The CsVMV promoter is isolated from the plasmid pCH27, derived from the plasmid pUC19 containing the expression cassette for a herbicide tolerance gene under the control of CSVMV. For this, a standard PCR was carried out on a thermocycler with Pfu polymerase generating blunt ends; 1 cycle of 5 min at 95° C., 30 cycles [95° C. 30 sec, 57° C. 30 sec, 72° C. 1 min], 72° C. 3 min. The primers used are: N-CsVMV: GCCCTCGAGG TCGACGGTAT TGATCAGCTT CC (SEQ ID NO: 50) introducing the XhoI and BclI sites C-CsVMV: CGCTCTAGAA TTCAGATCTA CAAAC (SEQ ID NO: 51) (EcoRI)

The 565 bp fragment generated is digested with XhoI+EcoRI before being inserted into the plasmid pEPA13 digested beforehand with XhoI+EcoRI; the plasmid pEPA14 is obtained. The Nos terminator is isolated from the plasmid pRD11, derived from pBlueScript II-SK(−) in which the Nos terminator is cloned, by HindIII+NotI digestion. The 292 bp fragment obtained is cloned into the plasmid pEPA14 opened with the same enzymes, giving pEPA15.

pEPA15 cassette=CsVMV promoter-hpa C-Nos terminator (FIG. 10; SEQ ID No. 19).

III.2. HPAH

The HPAH gene was isolated from *Pseudomonas acidovorans* by PCR on a plasmid derived (p5kbC) from genomic DNA cosmid library, using the following oligonucleotides:

```
Start ORF2 (AflIII):
CAGAGGACGA ACAACATGTC CCACC       (SEQ ID NO: 52)

ORF2 Fin3 (HindIII):
CTGTGGATGA AGCTTAAGAG GTTCAGGC    (SEQ ID NO: 53)
```

The reaction was carried out according to standard conditions. The amplified fragment, 1729 bp in size, was subcloned blunt-ended into the plasmid pBlueScript II SK digested with EcoRV. The plasmid pEPA16 thus obtained was sequenced. The CaMV 35S promoter is isolated from the plasmid pCH14, derived from the plasmid pBI 121 containing the GUS expression cassette: CaMV 35S promoter-GUS-Nos terminator. For this, a standard PCR was carried out on a thermocycler with Pfu polymerase generating blunt ends; 1 cycle of 5 min at 95° C. 30 cycles [95° C. 30 sec, 63° C. 30 sec, 72° C. 1 min], 72° C. 3 min. The primers used are:

```
N-CaMV:
                                          (SEQ ID NO: 54)
GCATGCCTCG AGCCCACAGA TGG introducing the XhoI
site

C-CaMV:
                                          (SEQ ID NO: 55)
CCACCCGGGG ATCCTCTAGA G introducing the BamHI
site.
```

The 839 bp fragment generated is digested with XhoI+BamHI before being inserted into the plasmid pEPA16 digested beforehand with XhoI+BclI: the plasmid pEPA17 is thus obtained. The Nos terminator is isolated from the plasmid pRD11 by PCR, under the same conditions as previously, for 1 cycle of 5 min at 95° C., 30 cycles [95° C. 30 sec, 57° C. 30 sec, 72° C. 1 min], 72° C. 3 min, with the following primers:

```
N-Nos:
                                          (SEQ ID NO: 56)
CAAGCTTATC GATACCGTCG ACG introducing HindIII

C-Nos:
                                          (SEQ ID NO: 57)
GSSTTGCGGC CGCAATTCCC GACCTAGGA ACATAG
introducing-NotI an AvrII.
```

The 305 bp fragment obtained is digested with NotI+HindIII before being cloned into the plasmid pEPA17 opened with the same enzymes, giving pEPA18.

pEPA18 cassette=CaMV 35S promoter-hpaH-Nos terminator (FIG. 11; SEQ ID No. 17).

III.3 HPPO

The HPPO gene was isolated from *Arthrobacter globiformis* by PCR on the cosmid 2A derived from a genomic DNA cosmid library, using the following oligonucleotides:

```
N-term-HPPO-ScaI:
                                          (SEQ ID NO: 58)
GAATTCAGTA CTTCACTTAC AGTGTCCGGC introducing the
EcoRI and ScaI restriction sites;

C-term-HPPO-AsuII-XhoI:
                                          (SEQ ID NO: 59)
GAATTCTCGA GTTCGAACAA ACTGAGTAGC AGCTCA
introducing the EcoRI, XhoI and AsuII sites.
```

The reaction was carried out according to standard conditions. The 1800 bp fragment obtained is cloned into the vector pGEMT-easy (Promega) according to the supplier's protocol. The plasmid pOZ151 thus obtained was sequenced. The cassette obtained by digestion with SphI+XhoI was cloned into the plasmid pBBR1-MCS (Gm) opened with the same enzymes, to give the plasmid pEPA20. The histone simple promoter is isolated from the plasmid pCH9, derived from the plasmid pUC19 containing the expression cassette for EPSPS: histone simple promoter-intron2-OTP-EPSPS-histone terminator. For this, a standard PCR was carried out with Pfu polymerase generating blunt ends; 1 cycle of 5 min at 95° C., 5 cycles [95° C. 30 sec, 45° C. 30 sec, 72° C. 1 min], 30 cycles [95° C. 30 sec, 65° C. 30 sec, 72° C. 1 min], 72° C. 3 min. The primers used are:

```
N-SH:
                                               (SEQ ID NO: 60)
GCTTGCATGC CTAGGTCGAG GAGAAATATG introducing the

SphI and AvrII sites

C-SH:
                                               (SEQ ID NO: 61)
CATGAGGGGT TCGAAATCGA TAAGC
```

The 970 bp fragment generated is digested with SphI before being inserted into the plasmid pEPA20 digested beforehand with SphI+ScaI; in the plasmid pEPA21 obtained, the initiating ATG of the HPPO gene is recreated behind the simple histone promoter. The histone terminator is isolated from the same plasmid pCH9 by PCR, under the same conditions as previously, for 1 cycle of 5 min at 95° C., 35 cycles [95° C. 30 sec, 55° C. 30 sec, 72° C. 1 min], 72° C. 3 min, with the following primers:

```
N-Hister:
                                               (SEQ ID NO: 62)
CTAGACCTAG GGGATCCCCC GATC introducing AvrII

C-Hister:
                                               (SEQ ID NO: 63)
CCCACTAGTG TTTAAATGAT CAGTCAGGCC GAAT introducing

SpeI and BclI.
```

introducing SpeI and BclI.

The 726 bp fragment obtained is digested with SpeI+AvrII before being cloned into the plasmid pEPA21 opened with SpeI, giving pEPA22.

pEPA22 cassette=histone simple promoter-hppO-histone terminator (FIG. 12; SEQ ID No. 15).

III.4. Association of the Genes

The cassette containing the HPAC gene is extracted from pEPA15 by NotI digestion and cloned into pEPA18 (NotI+Bsp120I) so as to form pEPA19 (FIG. 13; SEQ ID No. 21). The latter is digested with AvrII so as to clone the extracted cassette into the AvrII+SpeI sites of pEPA22. The plasmid containing the three constructs is pEPA23 (FIG. 14; SEQ ID No. 22).

III.5. Binary Vector

In order to transform the plants with *Agrobactetium*, the three constructs can be extracted with BclI in order to be introduced into a binary vector of *Agrobacteria*.

Abbreviations:

3,4-DHPA 3,4-dihydroxyphenylacetic acid
4-HPA 4-hydroxyphenylacetic acid
DNA deoxyribonucleic acid
APcI Atmospheric Pressure chemical Ionization
RNA ribonucleic acid
mRNA messenger ribonucleic acid
ETB ethidium bromide
BLAST Basic Local Alignment Search Tool
BSA bovine serum albumin
$C.^{100}$ carbenicillin (100 ?g/mL)
CRLD Centre de Recherche La Dargoire [La Dargoire Centre for Research]
Da Dalton
DKN isoxaflutole diketonitrile
DMSO dimethyl sulfoxide
dATP 2'-deoxyadenosine 5'-triphosphate
dCTP 2'-deoxycytidine 5'-triphosphate
dGTP 2'-deoxyguanosine 5'-triphosphate
dNTP 2'-deoxynucleotide 5'-triphosphate
dTTP 2'-deoxythymidine 5'-triphosphate
DTE dithioerithritol DTT 1,4-dithiothreitol
EDTA ethylenediaminetetraacetic acid
FAD flavin adenine dinucleotide
FPLC fast protein liquid chromatography
$Gm^{20}$ gentamycin (20 ?g/mL)
HGA homogentisic acid
HPLC high performance liquid chromatography
HPP hydroxyphenylpyruvic acid
HPPD hydroxyphenylpyruvic acid dioxygenase
HPPO hydroxypherlylpyruvate oxidase
IFT isoxaflutole IPTG isopropyl-?-thiogalactopyranoside
$Kn^{50}$ kanamycin (50 ?g/mL)
kb kilo bases
Km Michaelis Menten constant
L-DOPA 3,4-dihydroxyphenylalanine
LB Luria Bertani medium
min minutes
mJ millijoules
MNDD manganese dependent dioxygenase
MndD gene encoding MNDD
$NAD^+$ (H, $H^+$) nicotinamide adenine dinucleotide (oxidized form/reduced form)
GMO genetically modified organism
OTP optimized transit peptide
bp base pairs
pBBR1MCS-Gm plasmid pBBR1MCS resistant to gentamycin
PCR polymerase chain reaction
ppm parts per million; $mg.L^{-1}$
PVDF polyvinylidene difluoride
qs quantity sufficient for
Q.r. respiratory coefficient
$Rif.^{100}$ rifampicin (100 ?g/mL)
NMR nuclear magnetic resonance
SDS sodium dodecyl sulfate
sec second
TBE trisborate EDTA
TEV tobacco etch virus
TEA trifluoroacetic acid
TrEMBL translated EMBL bank
Tris tris(hydroxymethyl)aminomethane
U.V. ultraviolet
vs versus
X-gal 5-bromo-4-chloro-3-?-D-galactopyranoside

REFERENCES

Abe, H.; Uchiyama M.; Sato, R. (1974) Isolation of phenylacetic acid and its p-hydroxyderivative as auxin-like substances from *Undaria pinnatifida. Agric. Biol. Chem.* 38: 897-898

Adachi, K.; Takeda, Y.; Senoh, S.; Kita, H. (1964) Metabolism of p-hydroxyphenylacetic acid in *Pseudomonas ovalis. Biochem. Biophys. Acta* 93: 483-493

Appert, C.; Logemann, E.; Hahlbrock, K.; Schmid, J.; Amrhein, N.; (1994) Structural and catalytic properties of the four phenylalanine ammonia-lyase isoenzymes from parsley (*Petroselinum crispum* Nym.); *Eur. J. Biochem.;* 225:491-499

Arunachalam, U.; Massey, V.; Vaidyanathan, C. S. (1992) p-hydroxyphenyl-acetate 3-hydroxylase. *J. Biol. Chem.* 267:25848-25855

Arunachalam, U.; Massey, V. (1994) Studies on the oxidative half-reaction of p-hydroxyphenylacetate 3-hydroxylase. *J. Biol. Chem.* 269: 11795-11801

Arunachalam, U.; Massey, V.; Miller, S. L (1994) Mechanism of p-hydroxyphenylacetate 3-hydroxylase. *J. Biol. Chem.* 269: 150-155

Aubert, S. (1994) Effet multiples du glycrol sur le mtabolisme de la cellule vgtale non chlorophylienne [Multiple effect of glycerol on the metabolism of the non-chlorophyll-containing plant cell]. Thesis. University Joseph Fourier—Grenoble—France Aubert S.; Gout, E.; Bligny, R.; Marty-Mazars, D.; Barrieu, F.; Alabouvette, J; Marty, F.; Douce, R. (1996a) Ultrastructural and biochemical characterization of autophagy in higher plant cells subjected to carbon deprivation: control by the supply of mitochondria with respiratory substrates. *J. Cell Biol.* 133: 1251-1263

Aubert, S.; Alban, C.; Bligny, R.; Douce, R. (1996b) Induction of beta-methylcrotonyl-coenzyme A carboxylase in higher plant cells during carbohydrate starvation: evidence for a role of MCCase in leucine metabolism. *FEBS Lett.* 383: 175-180

Aubert, S.; Bligny, R.; Douce, R. (1996c). NMR studies of metabolism in cell suspensions and tissue cultures, in "Nuclear Magnetic Resonance in Plant Physiology" (Y. Shachar-Hill and P. Pfeffer, Eds.), pp. 109-154, American Society of Plant Physiologists, Rockville, USA.

Aubert, S.; Bligny, R.; Day, D. A.; Whelan, J.; Douce, R. 1997. Induction of alternative oxidase synthesis by herbicides inhibiting branched-chain amino acid synthesis. *Plant J.* 11:649-657

Aubert, S.; Curien, G.; Bligny, R.; Gout, E.; Douce, R. (1998) Transport, compartimentation and metabolism of homoserine in higher plant cells. Carbon-13 and phosphorus-31-nuclear magnetic resonance studies. *Plant Physiol.* 116: 547-557

Aubert, S.; Pallett, K. (2000) Combined use of $^{13}$C- and $^{19}$F-NMR to analyse the mode of action and the metabolism of the fluoride herbicide isoxaflutole. *Plant Physiol. Biochem.,* 38: 517-523

Ausubel, F. M.; Brent, R.; Kingston, R. E.; Moore, D. D.; Seidman, J. G.; Smith, J. A.; Struhl, K. (1995) Current protocols in molecular biology (volume 1-4). Wiley ed., Massachusetts General Hospital & Harward Medical School.

Bate, N. J.; Orr, J.; Ni, W.; Meromi, A.; Nadler-Hassar, T.; Doerner, P. W.; Dixon, R. A.; Lamb, C. J.; Elkind, Y. (1994) Quantitative relationship between phenylalanine ammonia-lyase levels and phenylpropanoid accumulation in transgenic tobacco identifies a rate-determining step in natural product synthesis. *Proc. Natl. Acad. Sci. USA* 91: 7608-12

Battersby, A. R.; Chrystal, E. J.; Staunton, J. (1980) Studies of enzyme-mediated reactions. Part 12. Stereochemical course of the decarboxylation of (2S)-tyrosine to tyramine by microbial, mammalian and plant systems. *J. Chem. Soc.* 1: 31-42

Bickel, H.; Palme, L.; Schultz, G. (1978) Incorporation of shikmate and other precursors into aromatic amino acids and prenylquinones of isolated spinach chloroplasts. *Phytochemisty.* 17: 119-124

Bickel, E; Buchholz, G.; Schultz, G. (1979) On the compartimentation of the biosynthesis of aromatic amino acids and prenylquinones in higher plants. In Advances in the biochemist and physiology of plant lipids, Appelqvist, L. A. Liljenberg, C., eds. Elsevier, Amsterdam pp 369-375

Biswas, I.; Gruss, A.; Ehrlich, S. D.; Maguin, E. (1993) High-efficiency gene inactivation and replacement system for Gram-positive bacteria. *J. Bacteriol.* 175: 3628-3535

Blakley, E. R. (1977) The catabolism of L-tyrosine by an *Arthrobacter* sp., *Can. J. Microbiol.* 23:1128-1139

Bligny, R.; Leguay, J. J. (1987) Techniques of cell cultures. *Meth. Enzymol.* 148: 3-16

Boehringer Mannheim (1995) The DIG system user's guide for filter hybridization

Boldt, Y. R.; Sadowsky, M. J.; Ellis, L. B. M.; Que, L.; Wackett, L. P. (1995) A Manganese-dependent Dioxygenase from *Arthrobacter globiformis* CM-2 belongs to the major extradiol dioxygenase family. *J. Bacteriol.* 177: 1225-1232

Borresen, T; Klausen, N. K.; Larsen, L. M.; Sorensen, H. (1989) Purification and characterisation of tyrosine decarboxylase and aromatic-L-amino-acid decarboxylase. *Biochem. Biophys. Acta* 993:108-115

Bradford, M. M. (1976) A rapid and sensitive method for the quantification of microgram quantities of protein utilizing the principle of protein-dye binding. *Anal. Biochem.* 72: 248-254

Brouquisse, R.; James, F.; Pradet, A.; Raymond, P. (1992) Asparagine metabolism and nitrogen distribution during protein degradation in sugar-starved maize root tips. *Planta.* 188: 384-395

Callis, J. (1995) regulation of proteine degradation. *Plant Cell.* 7: 845-857

Campos-Garcia J., Najera R., Camarena L., Soberon-Chavez G. (2000) The *Pseudomonas aeruginosa* motR gene involved in regulation of bacterial motility. *FEMS Microbiol Lett.* 184:57-62

Chan, M. T.; Chao, Y. C.; Yu, S. M. (1994) Novel gene expression system for plant cells based on induction of alpha-amylase promoter by carbohydrate starvation. *J. Biol. Chem.* 269:17635-17641

Chang, A. K.; Duggleby, R. G. (1997) Expression, purification and characterization of *Arabidopsis thaliana* acetohydroxyacid synthase. *Biochem. J.* 327: 161-169

Chevalier, C.; Bourgeois, E.; Just, D.; Raymond, P.; (1996) Metabolic regulation of asparagine synthetase gene expression in maize (*Zea mays* L.) root tips. *Plant J.* 9: 1-11

Chua, N. H. (1980) electrophoretic analysis of chloroplast proteins. *Methods Enzymol.* 69: 434-446

Coligan, J. E.; Dunn, B. M.; Ploegh, H. L.; Speicher, D. W.; Wingfield, P. T. Current protocols in protein science. Wiley ed.

Coligan, J. E. (1997) Chapter 11: Chemical analysis in Current Protocols in Protein Science. Coligan, J. E.; Dunn, B. M.; Ploegh, H. L.; Speicher, D. W.; Wingfield, P. T. (eds.) Wiley. Vol. 1.

David, C.; Daro, A.; Szalai, E.; Atarhouch, T.; Mergeay, M. (1996) Formation of polymeric pigments in the presence of bacteria and comparison with chemical oxidative coupling-II. Catabolism of tyrosine and hydroxyphenylacetic acid by *Alcaligenes eutrophus* CB34 and mutants. *Eur. Polym. J.,* 32: 669-679

De Lorenzo V., Herero M., Jakubzik U., Timmis K. N. (1990) Mini-Tn5 trasposon drivatives for insertion mutagenesis, promoter probing, and chromosomal insertion of cloned DNA in gram-negative eubacteria. *J Bacteriol* 172: 6568-6572

D'Souza L M, Willson R C, Fox G E (2000) Expression of RNAs in *Pseudomonas putida Curr Microbiol.* 40: 91-95

Despeghel, J. P.; Delrot, S. (1983) Energetics of amino acids uptake by *Vicia faba* leaf tissue. Plant Physiol. 71: 1-6

Dey & Harborne (1997) Plant Biochemistry, page 389, PA P. M. Dey & J. B. Harborne, Academic Press Fedi S., Brazil D., Dowling D. N., O'Gara F. (1996) Construction of a modified mini-Tn5 lacZY non-antibiotic marker cassette: ecological evaluation of a lacZY marked *Pseudomonas* strain in the sugarbeet rhizospherm *FEMS Microbiol Lett.* 135: 251-257

Feretti, L.; Sgaramella, V. (1981) Specific and reversible inhibition of the blunt end joining activity of the T4 DNA ligase. *Nucleic Acid Res.* 9:3695-3705

Ferrandez, A.; Garcia, J. L.; Diaz, E. (1997) Genetic characterization and expression in heterologous hosts of the 3-(3-hydroxyphenyl)-propionate catabolic pathway of *Escherichia coli* K12. *J. Bacteriol.* 179: 2573-2581

Filleur, S.; Daniel-Vedele, F. (1999) Expression analysis of a high affinity nitrate transporter isolated from *Arabidopsis thaliana* by differential display. *Planta* 207: 461-469

Flodin, C.; Whitfield, F. B. (1999) 4-hydroxybenzoic acid: a likely precursor of 2,4,6-tribromophenol in *Ulva lactuca. Phytochemistry.* 51:249-255

Flugge, U.-I. (1998) Metabolite transporters in plastids. *Curr. Opinion Plant Biotech.,* 1: 201-206

Folch, J.; Lees, M.; Sloane-Stanley, G. H. (1957) A simple method for the isolation and purification of lipids from animal tissues. *J Biol Chem* 226:497-509

Frommer, W. B.; Kwart, M.; Hirner, B.; Fischer, W. N.; Hummel, S.; Ninnemann, O. (1994) Transporters for nitrogenous compounds in plants. *Plant Mol. Biol.* 26: 1651-1670

Gaines, C. G.; Byng, G. S.; Whitaker, R. J.; Jensen, R. A. (1982) L-tyrosine regulation and biosynthesis via argenate dehydrogenase in suspension-cultured cells of *Nicotiana silvestri* speg. et comes. *Planta,* 156: 233-240

Galan, B.; Diaz, E.; Prieto, M. A. (2000) Functional analysis of the small component of the 4-hydroxyphenylacetate 3-monooxygenase of *Escherichia coli* W: a prototype of a new flavin NAD(P)H reductase subfamily. *J. Bacteriol.* 182 627-636

Garcia, I.; Rodgers, M.; Lenne, C.; Rolland, A.; Sailland, A.; Matringe, M. (1997) Subcellular localisation and purification of a p-hydroxyphenylpyruvate dioxygenase from cultured carrot cells and characterisation of the corresponding cDNA. *Biochem. J.;* 325: 761

Garcia, I.; Rodgers, M.; Ppin, R.; Ksieh, T.-F., Matringe, M. (1999) Characterization and subcellular compartmentation of recombinant 4-hydroxyphenylpyravate dioxygenase from *Arabidopsis* in transgenic tobacco. *Plant Physiol.* 119: 1507-1516

Gazzarini, S.; Lejay, L.; Gojon, A; Ninnemann, O.; Frommer, W. B.; von Wiren, N. (1999) Three functional transporters for constitutive, diurnally regulated and starvation-induced uptake of ammonium into *Arabidopsis* roots. *Plant Cell.* 11: 937-948

Genix, P.; Bligny, R.; Martin, J. B.; Douce, R. (1990) Transient accumulation of asparagine in sycamore cells after a long period of sucrose starvation. *Plant Physiol.* 94: 717-722

Georgalaki, M. D.; Sarantinopoulos, P.; Ferreira, E. S.; De Vuyst, L.; Kalantzopoulos, G.; Tsakalidou, E. (2000) Biochemical properties of *Streptococcus macedonicus* strains isolated from Greek Kasseri cheese. *J. Appl. Microbiol.* 88: 817-825

Goodchild, J. A.; Givan, C. V. (1990) Influence of ammonium and external pH on the amino and organic acid content of suspension culture cells of *Acer pseudoplatanus* L. *Physiol. plant* 78: 29-37

Goodwin & Mercer (1988) Introduction to plant biochemistry, 2nd edition. Pergamon Press p. 356

Gout, E.; Bligny, R.; Genix, P.; Tissut, M.; Douce, R. (1992). Effect of glyphosate on plant cell metabolism. $^{31}$P and $^{13}$C NMR studies. Biochimie. 74: 875-882

Greenberg, D. M. ( ) Metabolic pathways. Amino acids and tetrapyrroles, 3$^{rd}$ edition, Academic Press, vol. III: p. 148

Gross, D. (1975) Growth regulating substances of plant origin. *Phytochemistry.* 14: 2105-2112

Grunstein, M.; Hogness, D. S. (1975) Colony hybridization: a method for the isolation of cloned DNAs that contain a specific gene. *Proc. Natl. Acad. Sci. U.S.A.* 72: 3961-3965

Hahlbrock, K.; Scheel, D.; (1989) Physiology and molecular biology of phenylpropanoid metabolism. *Ann Rev. Plant Physiol. Plant Mol. Biol.;* 40: 347-369

Hareland, W. A.; Crawford, R. L.; Chapman, P. J.; Dagley, S. (1975) Metabolic function and properties of 4-hydroxyphenylacetic acid 1-hydroxylase from *Pseudomonas acidovorans. J. Bacteriol.,* 121: 272-285

Hess, J. L. (1993) Vitamine E, .alpha.-Tocophrols. In Antioxidans in Higher Plants Edited by Alscher, R.; Hess, J.; Boca Raton: CRC: p.: 111-134

Hill, C. M.; Duggleby, R. G. (1998) Mutagenesis of *Escherichia coli* acetohydroxyacid synthase isoenzyme II and characterization of three herbicide-insensitive forms. *Biochem. J.* 335: 653-661

Homeyer, U.; Litek, K.; Huchzermeyer, B.; Schultz, G. (1989) Uptake of phenylalanine into isolated barley vacuoles is driven by both tonoplast adenosine triphosphatase and pyrophosphatase. *Plant Physiol.* 89: 1388-1393

Jones, D.; Keddie, R. M. (1991) The genus *Arthrobacter*. In: The procaryotes (Balows, A; Truper, H. G.; Dworkin, M; Harder, W.; Schleifer, K. H., eds.) 2nd eds., Springer-Verlag, New-York Journet E. P., Bligny R., Douce R. (1986) Biochemical changes during sucrose deprivation in higher plant cells. *J. Biol. Chem.* 261: 3193-3199

Junge, K; Gosink, J. J.; Hoppe, H.-G.; Staley, J. T. (1998) *Arthrobacter, Brachybacterium* and *Planococcus* isolates identified from antarctic sea ice brine. Description of *Planococcus mcmeekinii*, sp. nov. *System. Appl. Appl. Microbiol.,* 21: 306-314

Kaiser, G.; Martinoia, E.; Wiemken, A. (1982) Rapid appearance of photosynthetic products in the vacuoles isolated from barley mesophyll protoplasts by a new fast method. *Z. Pflanzenphysiol.* 107: 103-113

Keen, N. T., Tamai, S., Kobayashi, D., Trollinger, D., (1988), Improved broad-host-range plasmids for DNA cloning in gram-negative bacteria, *Gene,* 70, 191-197

Kindl, H. (1969) Biosynthesis and metabolism of hydroxyphenylacetic acids in higher plants. *Eur. J. Biochem.* 7:340-347

Koch, C.; Schumann, P.; Stackebrandt, E. (1995) Reclassification of *Micrococcus* agilis (Ali-Cohen 1889) to the genus *Arthrobacter* as *Arthrobacter agilis* comb. nov. and emendation of the genus *Arthrobacter. Int. J. Syst. Bacteriol.* 45: 837-839

Kovach M E, Phillips R W, Elzer P H, Roop R M 2nd, Peterson K M (1994) pBBR1MCS: a broad-host-range cloning vector. *Biotechniques* 16: 800-802

Kovach M E, Elzer P H, Hill D S, Robertson G T, Farris M A, Roop R M 2nd, Peterson K M (1995) Four new derivatives of the broad-host-range cloning vector pBBR1MCS, carrying different antibiotic-resistance cassettes. *Gene* 166: 175-176

Kruk, J.; Strzalka, K. (1998) Identification of plastoquinone-C in spinach and maple leaves by revere-phase high-performance liquid chromatography. *Phytochemistry* 49: 2267-2271

Laemmli, U. K. (1970) Cleavage of structural proteins during the assembly of the head of bacteriophage T4. *Nature.* 227: 680-683

Lamport, D. T. A.; Northcote, D. H. (1960) Hydroxyproline in primary cell walls of higher plants. *Nature:* 188: 665-666

Laursen, R. A. (1971) Solid-phase Edman degradation. An automatic peptide sequencer. *Eur. J. Biochem.* 20: 89-102.

Li, Z.-C; Bush, D. R. (1990).DELTA.pH-dependent amino acid transport into plasma membrane vesicles isolated from sugar beet leaves. I. Evidence for carrier-mediated, electrogenic flux through multiple transport systems. *Plant Physiol.* 94: 268-277

Li, Z.-C; Bush, D. R. (1991).DELTA.pH-dependent amino acid transport into plasma membrane vesicles isolated from sugar beet (*Beta vulgaris* L.) leaves. II. Evidence for multiple aliphatic, neutral amino acid symports. *Plant Physiol.* 96: 1338-1344

Liu, D.-L.; Xu, S.-X; Wang, W.-F. (1998) a novel lignan glucoside from *Forsythia suspensa* Vahl. *J. Chin. Pharmaceut. Sci.* 7: 49-51

Löffelhardt, W. (1977) The biosynthesis of phenylacetic acids in blue-green alga *Anacystis nidulans*: evidence for the involvement of a thylakoid-bound L-amino acid oxidase. *Z. Naturforsch.* 32: 345-350

Luscombe, B. M.; Palett, K. E.; Loubierre, P.; Millet, J.-C.; Melgarejo, J.; Vrabel, T. E. (1995) RPA 201772 a novel herbicide for broad leaf and grass weeds control in maize and sugar cane, *Proc. Brighton Crop Prot. Conf. Weeds,* 1: 35

Luscombe, B. M.; Pallett, K. E.; (1996) Isoxaflutole for weed control in maize, *Pesticide Outlook*; December, 29

Lutterbach, R.; Stockigt, J. (1994) in vivo investigation of plant cell metabolism by men of natural-abundance $^{13}$C-NMR spectroscopy. *Helv. Chim. Acta,* 77: 2153-2161

Lutterbach, R.; Stockigt, J.; (1995), Dynamics of the biosynthesis of methylrsubin in plant cells employing in vivo $^{13}$C-NMR without labelling. *Phytochemistry,* 40: 801-806

MacLaighlin, P. J.; Weihrauch, J. L. (1979) Vitamine E content of foods. *J. Am. Diet. Assoc.* 75: 647-665

Maniatis, T.; Fritsch, E. F.; Sambrook, J. (1982) Molecular cloning-A laboratory manual eds Cold Spring Harbor Laboratory Martin, M.; Gibello, A.; Fernandez, J.; Ferrer, E.; Garrido-Pertierra, A. (1991) Catabolism of 3- and 4-hydroxyphenylacetic acid by *Klebsiella pneumoniae. J. Gen. Microbiol.* 132: 621-628.

Mayer, M. P.; Beyer, P.; Kleinig, H. (1990) Quinone compounds are able to replace molecular oxygen as terminal electron acceptor in phytoen desaturation in chromoplasts of *Narcissus pseudonarcissus L. Eur. J. Biochem.* 191: 359-363

Mayer, M. P.; Nievelstein, V.; Beyer, P. (1992) Purification and characterization of a NADPH dependent oxidoreductase from chromoplasts of *Narcissus pseudonarcissus*: a redox-mediator possibly involved in carotene desaturation. *Plant Physiol. Biochem.* 30: 389-398

Mazelis, M. (1980) Amino acid metabolism In "the biochemistry of plants" (Stumpf, P K, Conn, E E; eds.), vol. 5: amino acids and derivatives. Academic press, London, N.Y., pp: 1-55

Michal, G.-ed.-(1999) Biochemical Pathways, An atlas of biochemistry and molecular biology, Wiley & Spektrum eds., p. 60

Miflin, B. J.; Lea, P. J. (1982) Ammonium assimilation and amino acid metabolism. In A. B. Boulter, B. Parthiers, eds, Encyclopedia of Plant Physiology, Vol. 14, Nucleic Acids and Proteins in Plants 1. Springer Verlag, Berlin PP: 5-64

Moreno-Arribas, V.; Lonvaud-Funel, A. (1999) Tyrosine decarboxylase activity of *Lactobacillus brevis* IOEB 9809 isolated from wine and *L. brevis* ATCC 367. FEMS Microbiology Letters. 180: 55-60

Moreno-Arribas, V.; Torlois, S.; Joyeux, A.; Bertrand, A.; Lonvaud-Funel, A. (2000) Isolation, properties and behaviour of tyramine-producing lactic acid bacteria from wine. *J. Appl. Microbiol.* 88: 584593

Morot-Gaudry, J. F. (1997) Assimilation de l'azote chez les plantes. Aspects physiologique, biochimique et molculaire. INRA Editions.

Mouillon, J. M.; Aubert, S.; Bourguignon, J.; Gout, E.; Douce, R.; Rebeill, F. (1999) Glycine and serine catabolism in non-photosynthetic higher plant cells: their role in C1 metabolism *Plant J.* 20: 197-205

Murashige, T.; Skoog (1962) A revised medium for rapid growth and bio assays with tobacco tissue cultures. *Physiol. Plant.* 15: 473

Negrel, J.; Javelle, F.; (1995); Induction of phenylpropanoid and tyramine metabolism in pectinase or pronase elicited cell suspension cultures of tobacco (*Nicotiana tabacum*); *Physiologia Plantarum,* 95: 569-574

Nester, E. W.; Montoya, A. L. (1976) An enzyme common to histidine and aromatic amino acid biosynthesis in *Bacillus subtilis. J. Bacteriol.* 126: 699-705

Norris, S. R.; Barette, T. R.; DellaPenna, D. (1995) Genetic dissection of carotenoid synthesis in *Arabidopsis* defines plastoquinone as an essential component of phytoene desaturation *Plant Cell* 7: 2139-2149

Pallett, K. E.; Little, J. P.; Sheekey, M.; Veerasekaran, P. (1998) The mode of action of Isoxaflutole. I. Physiological effects, metabolism and selectivity. *Pestic. Biochem Physiol.* 62: 113-124

Prieto, M. A.; Perez-Randa, A.; Garcia, J. L. (1993) Characterization of an *Escherichia coli* aromatic hydroxylase with a broad substrate range. *J. Bacteriol.* 175: 2162-Prieto, M. A.; Garcia, J. L.; (1994) Molecular characterization of 4-hydroxyphenylacetate 3-hydroxylase of *Escherichia coli. J. Biol. Chem.* 269: 22823-22829

Prieto, M. A.; Diaz, E.; Garcia, J. L. (1996) Molecular characterization of the 4-hydroxyphenylacetate catabolic pathway of *Escherichia coli* W: engineering a mobile aromatic degradative cluster. *J. Bacteriol.* 178: 111-120

Prieto M. A., Kellerhals M. B., Bozzato G. B., Radnovic D., Witholt B., Kessler B. (1999) Engineering of stable reombinant bacteria for production of chiral medium-chain-length poly-3-hydroxyakanoates. *Appl. Environ Microbiol.* 65: 3265-3271

Roberts, J. K. M. (2000) NMR adventures in the metabolic labyrinth within plants. *Trends Plant Sci.* 5: 30-34

Roby, C.; Martin, J. B.; Bligay, R.; Douce, R. (1987) Biochemical changes during sucrose deprivation in higher plant cells. Phosphos-31 nuclear resonance magnetic studies. *J. Biol. Chem.* 262: 5000-5007

Sailland, A.; Matringe, M.; Rolland, A.; Pallett, K. (1995) Gene de l'hydroxy-phnyl pyruvate dioxygnase et obtention de plantes contenant ce gne rsistantes aux herbicides [Hydroxyphenylpyruvate dioxygenase gene and production of herbicide-resistant plants containing this gene]. WO 96/385567

Sailland, A., Derose, R. (1999) Method for enzymatic preparation of homogentisate. WO9934008 A 19990708

Sambrok; Fritsch; Maniatis. Molecular cloning. A laboratory manual, 2$^{nd}$ edition Schroeder, C.; Sommer, J.; Humpfer, E.; Stockigt, J. (1997) Inverse correlated $^{1}$H-$^{13}$C in vivo NMR as a probe to follow the metabolism of unlabelled vanillin by plant cell cultures. *Tetrahedron,* 53: 927-934

Schoenle, E. J.; Adams, L. D.; Sammons, D. W. (1984) Insulin-induced rapid decrease of a major protein in fat cell plasma membranes. *J. Biol. Chem.* 259: 12112-12116

Shachar-Hill, Y.; Pfeffer, P. E.; Germann, M. W. (1996) Following plant metabolism in vivo and in extracts with heteronuclear two-dimensional nuclear magnetic resonance spectroscopy. *Analytic. Biochem.,* 243: 110-118

Singer, M.; Berg, P. (1992) Genes & Genomes. Ed. VIGOT, Paris

Sparnins, V. L.; Dagley, S. (1975) Alternative routes of aromatic catabolism in *Pseudomonas acidovorans* and *Pseudomonas putida*: Gallic acid as a substrate and inhibitor of dioxygenases. *J. Bacteriol.* 124: 1374-1381

Stafford, H. A.; (1994) Anthocyanins and betalains: evolution of the mutually exclusive pathways. *Plant Sci;* 101: 91-98

Suemori, A.; Nakajima, K.; Kurane, R.; Nakamura, Y. (1995) L-Phenylalanine and L-Tyrosine degradative pathways in *Rhodococcus erythropolis. Report Nat. Inst. Biosci. Hum. Tech.* 3: 33-36

Suemori, A.; Nakajima, K.; Kurane, R.; Nakamura, Y. (1996) Purification and characterization of o-hydroxyphenylacetate 5-hydroxylase, m-hydroxyphenylacetate 6-hydroxylase and p-hydroxyphenylacetate 1-hydroxylase from *Rhodococcus erythropolis. Journal of Fermentation and Bioengineering,* 81: 133-137

Swiatek, L.; Grabias, B.; Kalemba, D. (1998) Phenolic acids in certain medicinal plants of the genus *Artemisia. Pharm. Pharmacol. Lett.* 4:158-160

Swiatek, L. (1977) kwasy fenolowe I Glukozydy irydoidowe w niektorych krajowych gatunkach leczniczych z rodzaju *Plantago. Herba Polonica* XXIII (3): 201-209

Takizawa, N.; Yokoyama, H.; Yanagihara, K.; Hatta, T.; Kiyohara, H. (1995) A locus of *Pseudomonas pickettii* DTP0602. had, that encodes 2,4,6-trichlorophenol 4-dechlorinase with hydroxylase activity, and hydroxylation of various chlorophenols by the enzyme. *J. Ferment. Bioeng.* 80: 318-326

Trieu-Cuot, P.; Carlier, C.; Poyart-Salmeron, C.; Courvalin, P. (1991) An integrative vector exploiting the transposition properties of Tn545 for insertional mutagenesis and cloning of genes from Gram-positive bacteria. *Gene* 106: 21-27

Tseng, T. C.; Tsai, T. H.; Lue, M. Y.; Lee, H. T. (1995) Identification of sucrose-regulated genes in cultured rice cells using mRNA differential display. *Gene.* 161: 179-1782

Vertes, A.; Asai, Y.; Inui, N; Kobayashi, M; Kurusu, Y.; Yukawa, H., (1994) Transposon mutagenesis of Coryneform bacteria, *Mol. Gen Genet.,* 245, 397-405

Vierstra, R. D. (1993) Protein degradation in plants. *Ann. Rev. Plant Physiol. Plant Mol. Biol.* 44: 385-410

Viviani; F.; Little, J.; Pallett, K. E. (1998) Mode of action of Isoxaflutole-2-Characterisation of the inhibition of the carrot 4-hydroxyphenylpyuvate dioxygenase by the diketonitrile derivative of isoxaflutole; *Pestic. Biochem. Physiol.* 62: 125-134

Whistance, G. R.; Threlfall, D. R. (1970) Biosynthesis of phytoquinones. Homogentisic acid: a precursor of plastoquinones, tocopherols and alpha-tocopherolquinone in higher plants, green algae and blue-green algae. *Biochem J.* 117: 593-600

Xun, L. Y. (1996) Purification and characterization of chlorophenol 4-monooxygenase from *Burkholderia cepacia* AC1100. *J. Bacteriol.* 178: 2645-2649

Xun, L. & Sandvik, E. R. (2000) Characterization of 4-hydroxyphenylacetate 3-hydroxylase (HpaB) of *Escherichia coli* as a reduced Flavin Adenine Dinucleotide-utilizing monooxygenase. *Appl Env. Microbiol.* 66: 481-486

The invention claimed is:

1. A method for making plants tolerant to a herbicide, characterized in that at least one enzyme making it possible to bypass the metabolic pathway inhibited by said herbicide is expressed in said plants, wherein said at least one enzyme includes HPAH and HPAC, and wherein said HPAH is encoded by a polynucleotide selected from the group consisting of the coding sequences of SEQ ID No. 7 and SEQ ID No. 17, and polynucleotides capable of selectively hybridizing to said coding sequence of SEQ ID No. 7 or SEQ ID No. 17 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS, and said HPAC is encoded by a polynucleotide selected from the group consisting of the coding sequences of SEQ ID No. 9, SEQ ID No. 11, SEQ ID No. 13 and SEQ ID No. 19, and polynucleotides capable of selectively hybridizing to said coding sequence of SEQ ID No. 9, SEQ ID No. 11, SEQ ID No. 13 or SEQ ID No. 19 under the prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS.

2. The method as claimed in claim 1, characterized in that the herbicide is an HPPD inhibitor.

3. The method as claimed in claim 2, characterized in that an HPP oxidase is additionally expressed in the plant.

4. An isolated polynucleotide, selected from the group consisting of a) a polynucleotide that encodes an HPAH selected from the group consisting of the coding sequences of SEQ ID No. 7 and SEQ ID No. 17, and polynucleotides capable of selectively hybridizing to said coding sequence of SEQ ID No. 7 or SEQ ID No. 17 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS, and b) a polynucleotide that encodes an HPAC selected from the group consisting of the coding sequences of SEQ ID No. 9, SEQ ID No. 11, SEQ ID No. 13 and SEQ ID No. 19, and polynucleotides capable of selectively hybridizing to said coding sequence of SEQ ID No. 9, SEQ ID No. 11, SEQ ID No. 13 or SEQ ID No. 19 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS.

5. The polynucleotide of claim 4, wherein said polynucleotide is selected from the group consisting of a polynucleotide that encodes an HPAH selected from the group consisting of the coding sequences of SEQ ID No. 7 and SEQ ID No. 17, and polynucleotides capable of selectively hybridizing to said coding sequence of SEQ ID No. 7 or SEQ ID No. 17 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS.

6. The polynucleotide of claim 4, wherein said polynucleotide is selected from the group consisting of a polynucleotide that encodes an HPAC selected from the group consisting of the coding sequences of SEQ ID No. 9, SEQ ID No. 11, SEQ ID No. 13 and SEQ ID No. 19, and polynucleotides capable of selectively hybridizing to said coding sequence of SEQ ID No. 9, SEQ ID No. 11, SEQ ID No. 13 or SEQ ID No. 19 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS.

7. An expression cassette comprising a polynucleotide as claimed in claim 4.

8. A cloning or expression vector, characterized in that it comprises at least one expression cassette as claimed in claim 7.

9. A transformed plant cell, characterized in that it comprises at least one expression cassette as claimed in claim 7.

10. The transformed plant cell of claim 9, wherein said at least one expression cassette comprises an expression cassette comprising a polynucleotide that encodes an HPAH selected from the group consisting of the coding sequences of SEQ ID No. 7 and SEQ ID No. 17, and polynucleotides capable of selectively hybridizing in to said coding sequence of SEQ ID No. 7 or SEQ ID No. 17 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS, and an expression cassette comprising a polynucleotide that encodes an HPAC selected from the group consisting of the coding sequences of SEQ ID No. 9, SEQ ID No. 11, SEQ ID No. 13 and SEQ ID No. 19, and polynucleotides capable of selectively hybridizing to said coding sequence of SEQ ID No. 9, SEQ ID No. 11, SEQ ID No. 13 or SEQ ID No. 19 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS.

11. A transformed plant, characterized in that it comprises at least one expression cassette as claimed in claim 7.

12. A seed of the transformed plant as claimed in claim 11.

13. A method of transforming plants, comprising introducing at least one expression cassette as claimed in claim 5 into the genome of a plant.

14. The transformed plant of claim 11, wherein said at least one expression cassette comprises an expression cassette comprising a polynucleotide that encodes an HPAH selected from the group consisting of the coding sequences of SEQ ID No. 7 and SEQ ID No. 17, and polynucleotides capable of selectively hybridizing to said coding sequence of SEQ ID No. 7 or SEQ ID No. 17 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS, and an expression cassette comprising a polynucleotide that encodes an HPAC selected from the group consisting of the coding sequences of SEQ ID No. 9, SEQ ID No. 11, SEQ ID No. 13 and SEQ ID No. 19, and polynucleotides capable of selectively hybridizing to said coding sequence of SEQ ID No. 9, SEQ ID No. 11, SEQ ID No. 13 or SEQ ID No. 19 under the following conditions: prehybridization for four hours at 68° C. in a solution of 5×SSC, 6% Denhardt's, and 0.5% SDS; hybridization for sixteen hours at 68° C.; and washes at 65° C. in 2×SSC, 0.1% SDS.

15. A seed of the transformed plant as claimed in claim 14.

16. A method for selective weeding of crop plants, comprising applying an HPPD-inhibiting herbicide to transformed plants as claimed in claim 14.

17. The method as claimed in claim 16, characterized in that the herbicide is applied in pre-emergence and/or in post-emergence.

18. A method of weed killing in an area of a field comprising transformed plants as claimed in claim 14 or seeds of transformed plants as claimed in claim 14, comprising applying in said area of the field, a dose, which is toxic for said weeds, of an HPPD-inhibiting herbicide, without however substantially affecting said seeds or said transformed plants.

19. A method of growing transformed plants, wherein said transformed plants comprise an expression cassette comprising a polynucleotide encoding a polypeptide having HPAH activity and an expression cassette comprising a polynucleotide encoding a polypeptide having HPAC activity, characterized in that it comprises sowing the seeds as claimed in claim 15 in an area of a field suitable for growing said plants, applying to said area of said field a dose, which is toxic for the weeds, of a herbicide having HPPD as the target, in the event of weeds being present, without substantially affecting said seeds or said transformed plants, then harvesting the plants grown when they reach the desired maturity and, optionally, separating the seeds from the harvested plants.

* * * * *